United States Patent
Witt et al.

(10) Patent No.: US 11,839,422 B2
(45) Date of Patent: *Dec. 12, 2023

(54) ELECTROSURGICAL INSTRUMENT WITH FLUID DIVERTER

(71) Applicant: Cilag GmbH International, Zug (CH)

(72) Inventors: David A. Witt, Maineville, OH (US); Frederick E. Shelton, IV, Hillsboro, OH (US); David C. Yates, Morrow, OH (US); Chad P. Boudreaux, Cincinnati, OH (US); Eric M. Roberson, Lebanon, OH (US); Kevin L. Houser, Springboro, OH (US); Geoffrey S. Strobl, Williamsburg, OH (US)

(73) Assignee: Cilag GmbH International, Zug (CH)

( * ) Notice: Subject to any disclaimer, the term of this patent is extended or adjusted under 35 U.S.C. 154(b) by 578 days.

This patent is subject to a terminal disclaimer.

(21) Appl. No.: 16/997,136

(22) Filed: Aug. 19, 2020

(65) Prior Publication Data

US 2020/0375651 A1    Dec. 3, 2020

Related U.S. Application Data

(63) Continuation of application No. 15/274,559, filed on Sep. 23, 2016, now Pat. No. 10,751,117.

(51) Int. Cl.
*A61B 18/14* (2006.01)
*A61B 18/00* (2006.01)
*A61M 25/00* (2006.01)

(52) U.S. Cl.
CPC ............ *A61B 18/148* (2013.01); *A61B 18/14* (2013.01); *A61B 2018/0016* (2013.01);
(Continued)

(58) Field of Classification Search
CPC .................. A61B 18/18; A61B 18/148; A61B 2018/0016; A61B 2218/002; A61B 2218/007; A61B 2018/00196
See application file for complete search history.

(56) References Cited

U.S. PATENT DOCUMENTS

| 2,366,274 A | 1/1945 | Luth et al. |
| 2,458,152 A | 1/1949 | Eakins |

(Continued)

FOREIGN PATENT DOCUMENTS

| CN | 1634601 A | 7/2005 |
| CN | 1922563 A | 2/2007 |

(Continued)

OTHER PUBLICATIONS

Erbe Electrosurgery VIOR 200 S, (2012), p. 7, 12 pages accessed Mar. 31, 2014 at http://www.erbe-med.com/erbe/media/Marketing materialien/85140170 ERBE EN VIO 200 S D027541.

(Continued)

*Primary Examiner* — Daniel W Fowler
*Assistant Examiner* — Annie L Shoulders

(57) ABSTRACT

An end effector of an electrosurgical device may include a discharge port in communication with a first fluid path, an aspiration port in communication with a second fluid path, a first and second electrode, and a diverter in mechanical communication with the two electrodes. The diverter may receive, on its surface, a fluid emitted by the discharge port, and maintain a contact of the fluid with the first and second electrodes. The diverter may be further configured to prevent an aspiration, by the aspiration port, of the fluid on its surface. An electrosurgical device may include a source port in communication with a first fluid path, an evacuation port in communication with a second fluid path, a first and second electrode, and a housing. The device may include a (Continued)

shaft extending distally from the housing and the end effector as described above.

18 Claims, 28 Drawing Sheets

(52) U.S. Cl.
CPC ............... *A61B 2018/00035* (2013.01); *A61B 2018/00083* (2013.01); *A61B 2018/00101* (2013.01); *A61B 2018/00196* (2013.01); *A61B 2018/00589* (2013.01); *A61B 2018/00595* (2013.01); *A61B 2018/00922* (2013.01); *A61B 2218/002* (2013.01); *A61B 2218/007* (2013.01); *A61M 2025/0073* (2013.01)

(56) References Cited

U.S. PATENT DOCUMENTS

| | | | |
|---|---|---|---|
| 2,510,693 | A | 6/1950 | Green |
| 2,736,960 | A | 3/1956 | Armstrong |
| 2,849,788 | A | 9/1958 | Creek |
| 2,867,039 | A | 1/1959 | Zach |
| 3,015,961 | A | 1/1962 | Roney |
| 3,043,309 | A | 7/1962 | McCarthy |
| 3,166,971 | A | 1/1965 | Stoecker |
| 3,358,676 | A | 12/1967 | Frei et al. |
| 3,525,912 | A | 8/1970 | Wallin |
| 3,526,219 | A | 9/1970 | Balamuth |
| 3,580,841 | A | 5/1971 | Cadotte et al. |
| 3,614,484 | A | 10/1971 | Shoh |
| 3,636,943 | A | 1/1972 | Balamuth |
| 3,703,651 | A | 11/1972 | Blowers |
| 3,710,399 | A | 1/1973 | Hurst |
| 3,776,238 | A | 12/1973 | Peyman et al. |
| 3,777,760 | A | 12/1973 | Essner |
| 3,805,787 | A | 4/1974 | Banko |
| 3,862,630 | A | 1/1975 | Balamuth |
| 3,900,823 | A | 8/1975 | Sokal et al. |
| 3,906,217 | A | 9/1975 | Lackore |
| 3,918,442 | A | 11/1975 | Nikolaev et al. |
| 3,946,738 | A | 3/1976 | Newton et al. |
| 3,955,859 | A | 5/1976 | Stella et al. |
| 3,956,826 | A | 5/1976 | Perdreaux, Jr. |
| 3,988,535 | A | 10/1976 | Hickman et al. |
| 4,005,714 | A | 2/1977 | Hiltebrandt |
| 4,034,762 | A | 7/1977 | Cosens et al. |
| 4,047,136 | A | 9/1977 | Satto |
| 4,058,126 | A | 11/1977 | Leveen |
| 4,063,561 | A | 12/1977 | McKenna |
| 4,099,192 | A | 7/1978 | Aizawa et al. |
| 4,156,187 | A | 5/1979 | Murry et al. |
| 4,188,927 | A | 2/1980 | Harris |
| 4,200,106 | A | 4/1980 | Douvas et al. |
| 4,203,430 | A | 5/1980 | Takahashi |
| 4,220,154 | A | 9/1980 | Semm |
| 4,237,441 | A | 12/1980 | van Konynenburg et al. |
| 4,278,077 | A | 7/1981 | Mizumoto |
| 4,281,785 | A | 8/1981 | Brooks |
| 4,304,987 | A | 12/1981 | van Konynenburg |
| 4,314,559 | A | 2/1982 | Allen |
| 4,384,584 | A | 5/1983 | Chen |
| 4,445,063 | A | 4/1984 | Smith |
| 4,463,759 | A | 8/1984 | Garito et al. |
| 4,491,132 | A | 1/1985 | Aikins |
| 4,492,231 | A | 1/1985 | Auth |
| 4,535,773 | A | 8/1985 | Yoon |
| 4,545,926 | A | 10/1985 | Fouts, Jr. et al. |
| 4,550,870 | A | 11/1985 | Krumme et al. |
| 4,582,236 | A | 4/1986 | Hirose |
| 4,585,282 | A | 4/1986 | Bosley |
| 4,597,390 | A | 7/1986 | Mulhollan et al. |
| 4,617,927 | A | 10/1986 | Manes |
| 4,633,874 | A | 1/1987 | Chow et al. |
| 4,634,420 | A | 1/1987 | Spinosa et al. |
| 4,640,279 | A | 2/1987 | Beard |
| 4,655,746 | A | 4/1987 | Daniels et al. |
| 4,671,287 | A | 6/1987 | Fiddian-Green |
| 4,708,127 | A | 11/1987 | Abdelghani |
| 4,735,603 | A | 4/1988 | Goodson et al. |
| 4,761,871 | A | 8/1988 | O'Connor et al. |
| 4,777,951 | A | 10/1988 | Cribier et al. |
| 4,797,803 | A | 1/1989 | Carroll |
| 4,798,588 | A | 1/1989 | Aillon |
| 4,802,461 | A | 2/1989 | Cho |
| 4,803,506 | A | 2/1989 | Diehl et al. |
| 4,830,462 | A | 5/1989 | Karny et al. |
| 4,832,683 | A | 5/1989 | Idemoto et al. |
| 4,838,853 | A | 6/1989 | Parisi |
| 4,849,133 | A | 7/1989 | Yoshida et al. |
| 4,850,354 | A | 7/1989 | McGurk-Burleson et al. |
| 4,860,745 | A | 8/1989 | Farin et al. |
| 4,865,159 | A | 9/1989 | Jamison |
| 4,878,493 | A | 11/1989 | Pasternak et al. |
| 4,880,015 | A | 11/1989 | Nierman |
| 4,896,009 | A | 1/1990 | Pawlowski |
| 4,910,389 | A | 3/1990 | Sherman et al. |
| 4,910,633 | A | 3/1990 | Quinn |
| 4,911,148 | A | 3/1990 | Sosnowski et al. |
| 4,919,129 | A | 4/1990 | Weber, Jr. et al. |
| 4,920,978 | A | 5/1990 | Colvin |
| 4,922,902 | A | 5/1990 | Wuchinich et al. |
| 4,936,842 | A | 6/1990 | D'Amelio et al. |
| 4,961,738 | A | 10/1990 | Mackin |
| 4,967,670 | A | 11/1990 | Morishita et al. |
| 4,981,756 | A | 1/1991 | Rhandhawa |
| 5,007,919 | A | 4/1991 | Silva et al. |
| 5,019,075 | A | 5/1991 | Spears et al. |
| 5,020,514 | A | 6/1991 | Heckele |
| 5,026,387 | A | 6/1991 | Thomas |
| 5,061,269 | A | 10/1991 | Muller |
| 5,093,754 | A | 3/1992 | Kawashima |
| 5,099,216 | A | 3/1992 | Pelrine |
| 5,099,840 | A | 3/1992 | Goble et al. |
| 5,104,025 | A | 4/1992 | Main et al. |
| 5,106,538 | A | 4/1992 | Barma et al. |
| 5,108,383 | A | 4/1992 | White |
| 5,112,300 | A | 5/1992 | Ureche |
| 5,123,903 | A | 6/1992 | Quaid et al. |
| 5,150,102 | A | 9/1992 | Takashima |
| 5,150,272 | A | 9/1992 | Danley et al. |
| 5,156,633 | A | 10/1992 | Smith |
| 5,160,334 | A | 11/1992 | Billings et al. |
| 5,162,044 | A | 11/1992 | Gahn et al. |
| 5,167,725 | A | 12/1992 | Clark et al. |
| D332,660 | S | 1/1993 | Rawson et al. |
| 5,176,695 | A | 1/1993 | Dulebohn |
| 5,184,605 | A | 2/1993 | Grzeszykowski |
| 5,188,102 | A | 2/1993 | Idemoto et al. |
| 5,190,541 | A | 3/1993 | Abele et al. |
| 5,196,007 | A | 3/1993 | Ellman et al. |
| 5,205,459 | A | 4/1993 | Brinkerhoff et al. |
| 5,205,817 | A | 4/1993 | Idemoto et al. |
| 5,209,719 | A | 5/1993 | Baruch et al. |
| 5,213,569 | A | 5/1993 | Davis |
| 5,217,460 | A | 6/1993 | Knoepfler |
| 5,221,282 | A | 6/1993 | Wuchinich |
| 5,226,910 | A | 7/1993 | Kajiyama et al. |
| 5,234,428 | A | 8/1993 | Kaufman |
| 5,241,236 | A | 8/1993 | Sasaki et al. |
| 5,253,647 | A | 10/1993 | Takahashi et al. |
| 5,254,130 | A | 10/1993 | Poncet et al. |
| 5,257,988 | A | 11/1993 | L'Esperance, Jr. |
| 5,258,004 | A | 11/1993 | Bales et al. |
| 5,258,006 | A | 11/1993 | Rydell et al. |
| 5,261,922 | A | 11/1993 | Hood |
| 5,263,957 | A | 11/1993 | Davison |
| 5,267,091 | A | 11/1993 | Chen |
| 5,282,800 | A | 2/1994 | Foshee et al. |
| 5,285,945 | A | 2/1994 | Brinkerhoff et al. |
| 5,290,286 | A | 3/1994 | Parins |
| 5,293,863 | A | 3/1994 | Zhu et al. |
| 5,304,115 | A | 4/1994 | Pflueger et al. |

(56) References Cited

U.S. PATENT DOCUMENTS

| | | |
|---|---|---|
| D347,474 S | 5/1994 | Olson |
| 5,309,927 A | 5/1994 | Welch |
| 5,312,023 A | 5/1994 | Green et al. |
| 5,313,306 A | 5/1994 | Kuban et al. |
| 5,318,563 A | 6/1994 | Malis et al. |
| 5,318,564 A | 6/1994 | Eggers |
| 5,318,565 A | 6/1994 | Kuriloff et al. |
| 5,318,570 A | 6/1994 | Hood et al. |
| 5,318,589 A | 6/1994 | Lichtman |
| 5,322,055 A | 6/1994 | Davison et al. |
| 5,324,260 A | 6/1994 | O'Neill et al. |
| 5,324,299 A | 6/1994 | Davison et al. |
| 5,326,013 A | 7/1994 | Green et al. |
| 5,330,471 A | 7/1994 | Eggers |
| 5,330,502 A | 7/1994 | Hassler et al. |
| 5,333,624 A | 8/1994 | Tovey |
| 5,339,723 A | 8/1994 | Huitema |
| 5,342,359 A | 8/1994 | Rydell |
| 5,344,420 A | 9/1994 | Hilal et al. |
| 5,346,502 A | 9/1994 | Estabrook et al. |
| 5,352,219 A | 10/1994 | Reddy |
| 5,359,992 A | 11/1994 | Hori et al. |
| 5,361,583 A | 11/1994 | Huitema |
| 5,366,466 A | 11/1994 | Christian et al. |
| 5,370,640 A | 12/1994 | Kolff |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,389,098 A | 2/1995 | Tsuruta et al. |
| 5,395,033 A | 3/1995 | Byrne et al. |
| 5,395,312 A | 3/1995 | Desai |
| 5,395,331 A | 3/1995 | O'Neill et al. |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,409,483 A | 4/1995 | Campbell et al. |
| D358,887 S | 5/1995 | Feinberg |
| 5,411,481 A | 5/1995 | Allen et al. |
| 5,413,575 A | 5/1995 | Haenggi |
| 5,417,709 A | 5/1995 | Slater |
| 5,419,761 A | 5/1995 | Narayanan et al. |
| 5,421,829 A | 6/1995 | Olichney et al. |
| 5,428,504 A | 6/1995 | Bhatla |
| 5,429,131 A | 7/1995 | Scheinman et al. |
| 5,431,640 A | 7/1995 | Gabriel |
| 5,443,463 A | 8/1995 | Stern et al. |
| 5,445,615 A | 8/1995 | Yoon |
| 5,445,638 A | 8/1995 | Rydell et al. |
| 5,449,370 A | 9/1995 | Vaitekunas |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,472,443 A | 12/1995 | Cordis et al. |
| 5,476,479 A | 12/1995 | Green et al. |
| 5,477,788 A | 12/1995 | Morishita |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,489,256 A | 2/1996 | Adair |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,648 A | 7/1996 | Yoon |
| 5,540,681 A | 7/1996 | Strul et al. |
| 5,542,916 A | 8/1996 | Hirsch et al. |
| 5,542,938 A | 8/1996 | Avellanet et al. |
| 5,558,671 A | 9/1996 | Yates |
| 5,562,609 A | 10/1996 | Brumbach |
| 5,562,610 A | 10/1996 | Brumbach |
| 5,562,657 A | 10/1996 | Griffin |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,601,601 A | 2/1997 | Tal et al. |
| 5,604,531 A | 2/1997 | Iddan et al. |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,307 A | 4/1997 | Donlon et al. |
| 5,618,492 A | 4/1997 | Auten et al. |
| 5,624,452 A | 4/1997 | Yates |
| 5,626,578 A | 5/1997 | Tihon |
| 5,628,760 A | 5/1997 | Knoepfler |
| 5,630,420 A | 5/1997 | Vaitekunas |
| 5,632,432 A | 5/1997 | Schulze et al. |
| D381,077 S | 7/1997 | Hunt |
| 5,643,175 A | 7/1997 | Adair |
| 5,645,065 A | 7/1997 | Shapiro et al. |
| 5,647,871 A | 7/1997 | Levine et al. |
| 5,651,780 A | 7/1997 | Jackson et al. |
| 5,653,677 A | 8/1997 | Okada et al. |
| 5,653,713 A | 8/1997 | Michelson |
| 5,657,697 A | 8/1997 | Murai |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,681,260 A | 10/1997 | Ueda et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,700,243 A | 12/1997 | Narciso, Jr. |
| 5,700,261 A | 12/1997 | Brinkerhoff |
| 5,704,900 A | 1/1998 | Dobrovolny et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,722,326 A | 3/1998 | Post |
| 5,722,426 A | 3/1998 | Kolff |
| 5,732,636 A | 3/1998 | Wang et al. |
| 5,733,074 A | 3/1998 | Stock et al. |
| 5,735,848 A | 4/1998 | Yates et al. |
| 5,738,652 A | 4/1998 | Boyd et al. |
| 5,741,226 A | 4/1998 | Strukel et al. |
| 5,741,305 A | 4/1998 | Vincent et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,776,130 A | 7/1998 | Buysse et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |

(56) References Cited

U.S. PATENT DOCUMENTS

| | | |
|---|---|---|
| 5,800,449 A | 9/1998 | Wales |
| 5,805,140 A | 9/1998 | Rosenberg et al. |
| 5,807,393 A | 9/1998 | Williamson, IV et al. |
| 5,810,718 A | 9/1998 | Akiba et al. |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman et al. |
| 5,828,160 A | 10/1998 | Sugishita |
| 5,836,867 A | 11/1998 | Speier et al. |
| 5,836,909 A | 11/1998 | Cosmescu |
| 5,836,943 A | 11/1998 | Miller, III |
| 5,836,990 A | 11/1998 | Li |
| 5,843,109 A | 12/1998 | Mehta et al. |
| 5,853,412 A | 12/1998 | Mayenberger |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,454 A | 3/1999 | Hones et al. |
| 5,887,018 A | 3/1999 | Bayazitoglu et al. |
| 5,891,142 A | 4/1999 | Eggers et al. |
| 5,893,835 A | 4/1999 | Witt et al. |
| 5,897,569 A | 4/1999 | Kellogg et al. |
| 5,902,239 A | 5/1999 | Buurman |
| 5,904,147 A | 5/1999 | Conlan et al. |
| 5,906,579 A | 5/1999 | Vander Salm et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,298 A | 8/1999 | Koike |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,849 A | 9/1999 | Munro |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,984,938 A | 11/1999 | Yoon |
| 5,989,182 A | 11/1999 | Hori et al. |
| 5,989,274 A | 11/1999 | Davison et al. |
| 5,989,275 A | 11/1999 | Estabrook et al. |
| 5,993,972 A | 11/1999 | Reich et al. |
| 6,003,517 A | 12/1999 | Sheffield et al. |
| 6,007,484 A | 12/1999 | Thompson |
| 6,013,052 A | 1/2000 | Durman et al. |
| 6,014,580 A | 1/2000 | Blume et al. |
| 6,024,741 A | 2/2000 | Williamson, IV et al. |
| 6,024,744 A | 2/2000 | Kese et al. |
| 6,033,375 A | 3/2000 | Brumbach |
| 6,033,399 A | 3/2000 | Gines |
| 6,039,734 A | 3/2000 | Goble |
| 6,050,996 A | 4/2000 | Schmaltz et al. |
| 6,053,172 A | 4/2000 | Hovda et al. |
| 6,063,098 A | 5/2000 | Houser et al. |
| 6,066,132 A | 5/2000 | Chen et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,152 A | 6/2000 | Nardella et al. |
| 6,083,151 A | 7/2000 | Renner et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,093,186 A | 7/2000 | Goble |
| 6,099,483 A | 8/2000 | Palmer et al. |
| 6,099,550 A | 8/2000 | Yoon |
| 6,109,500 A | 8/2000 | Alli et al. |
| 6,113,594 A | 9/2000 | Savage |
| 6,113,598 A | 9/2000 | Baker |
| 6,123,466 A | 9/2000 | Persson et al. |
| H1904 H | 10/2000 | Yates et al. |
| 6,127,757 A | 10/2000 | Swinbanks |
| 6,132,368 A | 10/2000 | Cooper |
| 6,139,320 A | 10/2000 | Hahn |
| 6,144,402 A | 11/2000 | Norsworthy et al. |
| 6,152,902 A | 11/2000 | Christian et al. |
| 6,152,923 A | 11/2000 | Ryan |
| 6,154,198 A | 11/2000 | Rosenberg |
| 6,159,160 A | 12/2000 | Hsei et al. |
| 6,159,175 A | 12/2000 | Strukel et al. |
| 6,162,208 A | 12/2000 | Hipps |
| 6,173,199 B1 | 1/2001 | Gabriel |
| 6,173,715 B1 | 1/2001 | Sinanan et al. |
| 6,174,309 B1 | 1/2001 | Wrublewski et al. |
| 6,176,857 B1 | 1/2001 | Ashley |
| 6,190,386 B1 | 2/2001 | Rydell |
| 6,193,709 B1 | 2/2001 | Miyawaki et al. |
| 6,206,844 B1 | 3/2001 | Reichel et al. |
| 6,206,876 B1 | 3/2001 | Levine et al. |
| 6,206,877 B1 | 3/2001 | Kese et al. |
| 6,210,403 B1 | 4/2001 | Klicek |
| 6,214,023 B1 | 4/2001 | Whipple et al. |
| 6,219,572 B1 | 4/2001 | Young |
| 6,221,007 B1 | 4/2001 | Green |
| 6,228,080 B1 | 5/2001 | Gines |
| 6,228,084 B1 | 5/2001 | Kirwan, Jr. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,248,074 B1 | 6/2001 | Ohno et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,258,086 B1 | 7/2001 | Ashley et al. |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,273,887 B1 | 8/2001 | Yamauchi et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,283,981 B1 | 9/2001 | Beaupre |
| 6,292,700 B1 | 9/2001 | Morrison et al. |
| 6,309,400 B2 | 10/2001 | Beaupre |
| 6,315,789 B1 | 11/2001 | Cragg |
| 6,319,221 B1 | 11/2001 | Savage et al. |
| 6,325,799 B1 | 12/2001 | Goble |
| 6,325,811 B1 | 12/2001 | Messerly |
| 6,328,751 B1 | 12/2001 | Beaupre |
| 6,340,878 B1 | 1/2002 | Oglesbee |
| 6,352,532 B1 | 3/2002 | Kramer et al. |
| 6,364,888 B1 | 4/2002 | Niemeyer et al. |
| 6,371,952 B1 | 4/2002 | Madhani et al. |
| 6,379,320 B1 | 4/2002 | Lafon et al. |
| 6,379,351 B1 | 4/2002 | Thapliyal et al. |
| D457,958 S | 5/2002 | Dycus et al. |
| 6,383,194 B1 | 5/2002 | Pothula |
| 6,387,094 B1 | 5/2002 | Eitenmuller |
| 6,387,109 B1 | 5/2002 | Davison et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |

(56) References Cited

U.S. PATENT DOCUMENTS

| | | |
|---|---|---|
| 6,423,082 B1 | 7/2002 | Houser et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,443,968 B1 | 9/2002 | Holthaus et al. |
| 6,443,969 B1 | 9/2002 | Novak et al. |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,464,703 B2 | 10/2002 | Bartel |
| 6,471,172 B1 | 10/2002 | Lemke et al. |
| 6,475,211 B2 | 11/2002 | Chess et al. |
| 6,475,216 B2 | 11/2002 | Mulier et al. |
| 6,480,796 B2 | 11/2002 | Wiener |
| 6,485,490 B2 | 11/2002 | Wampler et al. |
| 6,491,690 B1 | 12/2002 | Goble et al. |
| 6,491,691 B1 | 12/2002 | Morley et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,520,960 B2 | 2/2003 | Blocher et al. |
| 6,522,909 B1 | 2/2003 | Garibaldi et al. |
| 6,524,316 B1 | 2/2003 | Nicholson et al. |
| 6,531,846 B1 | 3/2003 | Smith |
| 6,533,784 B2 | 3/2003 | Truckai et al. |
| 6,537,196 B1 | 3/2003 | Creighton, IV et al. |
| 6,537,272 B2 | 3/2003 | Christopherson et al. |
| 6,537,291 B2 | 3/2003 | Friedman et al. |
| 6,540,693 B2 | 4/2003 | Burbank et al. |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,037 B2 | 5/2003 | Paton et al. |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,589,239 B2 | 7/2003 | Khandkar et al. |
| 6,594,517 B1 | 7/2003 | Nevo |
| 6,599,321 B2 | 7/2003 | Hyde, Jr. |
| 6,602,252 B2 | 8/2003 | Mollenauer |
| 6,610,060 B2 | 8/2003 | Mulier et al. |
| 6,616,450 B2 | 9/2003 | Mossle et al. |
| 6,616,600 B2 | 9/2003 | Pauker |
| 6,619,529 B2 | 9/2003 | Green et al. |
| 6,620,129 B2 | 9/2003 | Stecker et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,817 B2 | 11/2003 | Schara et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,663,941 B2 | 12/2003 | Brown et al. |
| 6,669,690 B1 | 12/2003 | Okada et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,695,840 B2 | 2/2004 | Schulze |
| 6,696,844 B2 | 2/2004 | Wong et al. |
| 6,716,215 B1 | 4/2004 | David et al. |
| 6,719,684 B2 | 4/2004 | Kim et al. |
| 6,719,765 B2 | 4/2004 | Bonutti |
| 6,722,552 B2 | 4/2004 | Fenton, Jr. |
| 6,723,094 B1 | 4/2004 | Desinger |
| 6,726,686 B2 | 4/2004 | Buysse et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,743,229 B2 | 6/2004 | Buysse et al. |
| 6,746,443 B1 | 6/2004 | Morley et al. |
| 6,752,815 B2 | 6/2004 | Beaupre |
| 6,762,535 B2 | 7/2004 | Take et al. |
| 6,766,202 B2 | 7/2004 | Underwood et al. |
| 6,767,349 B2 | 7/2004 | Ouchi |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,165 B2 | 8/2004 | Jin |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,216 B1 | 9/2004 | Ishikawa |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,806,317 B2 | 10/2004 | Morishita et al. |
| 6,808,491 B2 | 10/2004 | Kortenbach et al. |
| 6,811,842 B1 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,828,712 B2 | 12/2004 | Battaglin et al. |
| 6,832,998 B2 | 12/2004 | Goble |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,869,439 B2 | 3/2005 | White et al. |
| 6,875,220 B2 | 4/2005 | Du et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,632 B2 | 8/2005 | Nita et al. |
| 6,929,644 B2 | 8/2005 | Truckai et al. |
| 6,936,003 B2 | 8/2005 | Iddan |
| D509,589 S | 9/2005 | Wells |
| 6,939,347 B2 | 9/2005 | Thompson |
| 6,945,981 B2 | 9/2005 | Donofrio et al. |
| 6,953,461 B2 | 10/2005 | McClurken et al. |
| D511,145 S | 11/2005 | Donofrio et al. |
| 6,959,852 B2 | 11/2005 | Shelton, IV et al. |
| 6,974,462 B2 | 12/2005 | Sater |
| 6,976,844 B2 | 12/2005 | Hickok et al. |

(56) References Cited

U.S. PATENT DOCUMENTS

| | | |
|---|---|---|
| 6,976,969 B2 | 12/2005 | Messerly |
| 6,977,495 B2 | 12/2005 | Donofrio |
| 6,984,220 B2 | 1/2006 | Wuchinich |
| 6,986,738 B2 | 1/2006 | Glukhovsky et al. |
| 6,986,780 B2 | 1/2006 | Rudnick et al. |
| 6,994,709 B2 | 2/2006 | Iida |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,029,435 B2 | 4/2006 | Nakao |
| 7,039,453 B2 | 5/2006 | Mullick et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,352 B2 | 5/2006 | Shelton, IV et al. |
| 7,044,937 B1 | 5/2006 | Kirwan et al. |
| 7,052,496 B2 | 5/2006 | Yamauchi |
| 7,055,731 B2 | 6/2006 | Shelton, IV et al. |
| 7,056,284 B2 | 6/2006 | Martone et al. |
| 7,063,699 B2 | 6/2006 | Hess et al. |
| 7,066,879 B2 | 6/2006 | Fowler et al. |
| 7,066,936 B2 | 6/2006 | Ryan |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,579 B2 | 8/2006 | Yokoi et al. |
| 7,083,617 B2 | 8/2006 | Kortenbach et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,094,235 B2 | 8/2006 | Francischelli |
| 7,096,560 B2 | 8/2006 | Oddsen, Jr. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,118,570 B2 | 10/2006 | Tetzlaff et al. |
| 7,120,498 B2 | 10/2006 | Imran et al. |
| 7,124,932 B2 | 10/2006 | Isaacson et al. |
| 7,125,409 B2 | 10/2006 | Truckai et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,147,638 B2 | 12/2006 | Chapman et al. |
| 7,147,650 B2 | 12/2006 | Lee |
| 7,153,315 B2 | 12/2006 | Miller |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,163,548 B2 | 1/2007 | Stulen et al. |
| 7,169,104 B2 | 1/2007 | Ueda et al. |
| 7,169,146 B2 | 1/2007 | Truckai et al. |
| 7,169,156 B2 | 1/2007 | Hart |
| 7,170,823 B2 | 1/2007 | Fabricius et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,199,545 B2 | 4/2007 | Oleynikov et al. |
| 7,204,820 B2 | 4/2007 | Akahoshi |
| 7,207,471 B2 | 4/2007 | Heinrich et al. |
| 7,208,005 B2 | 4/2007 | Frecker et al. |
| 7,211,094 B2 | 5/2007 | Gannoe et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,064 B2 | 6/2007 | Hopper et al. |
| 7,235,073 B2 | 6/2007 | Levine et al. |
| 7,241,290 B2 | 7/2007 | Doyle et al. |
| 7,241,294 B2 | 7/2007 | Reschke |
| 7,241,296 B2 | 7/2007 | Buysse et al. |
| 7,246,734 B2 | 7/2007 | Shelton, IV |
| 7,251,531 B2 | 7/2007 | Mosher et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,267,685 B2 | 9/2007 | Butaric et al. |
| 7,270,658 B2 | 9/2007 | Woloszko et al. |
| 7,270,664 B2 | 9/2007 | Johnson et al. |
| 7,273,483 B2 | 9/2007 | Wiener et al. |
| 7,276,065 B2 | 10/2007 | Morley et al. |
| 7,282,048 B2 | 10/2007 | Goble et al. |
| 7,282,773 B2 | 10/2007 | Li et al. |
| 7,287,682 B1 | 10/2007 | Ezzat et al. |
| 7,297,145 B2 | 11/2007 | Woloszko et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,344,533 B2 | 3/2008 | Pearson et al. |
| 7,353,068 B2 | 4/2008 | Tanaka et al. |
| 7,354,440 B2 | 4/2008 | Truckai et al. |
| 7,357,287 B2 | 4/2008 | Shelton, IV et al. |
| 7,360,542 B2 | 4/2008 | Nelson et al. |
| 7,364,577 B2 | 4/2008 | Wham et al. |
| 7,367,973 B2 | 5/2008 | Manzo et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| D576,725 S | 9/2008 | Shumer et al. |
| 7,422,139 B2 | 9/2008 | Shelton, IV et al. |
| 7,422,586 B2 | 9/2008 | Morris et al. |
| 7,422,592 B2 | 9/2008 | Morley et al. |
| 7,429,259 B2 | 9/2008 | Cadeddu et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,249 B2 | 10/2008 | Buysse et al. |
| 7,435,582 B2 | 10/2008 | Zimmermann et al. |
| 7,439,732 B2 | 10/2008 | LaPlaca |
| 7,441,684 B2 | 10/2008 | Shelton, IV et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,448,993 B2 | 11/2008 | Yokoi et al. |
| 7,449,004 B2 | 11/2008 | Yamada et al. |
| 7,450,998 B2 | 11/2008 | Zilberman et al. |
| 7,451,904 B2 | 11/2008 | Shelton, IV |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |

(56) References Cited

U.S. PATENT DOCUMENTS

| | | |
|---|---|---|
| 7,479,148 B2 | 1/2009 | Beaupre |
| 7,479,160 B2 | 1/2009 | Branch et al. |
| 7,487,899 B2 | 2/2009 | Shelton, IV et al. |
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,503,893 B2 | 3/2009 | Kucklick |
| 7,505,812 B1 | 3/2009 | Eggers et al. |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,511,733 B2 | 3/2009 | Takizawa et al. |
| 7,513,025 B2 | 4/2009 | Fischer |
| 7,517,349 B2 | 4/2009 | Truckai et al. |
| 7,520,877 B2 | 4/2009 | Lee, Jr. et al. |
| 7,524,320 B2 | 4/2009 | Tierney et al. |
| 7,534,243 B1 | 5/2009 | Chin et al. |
| D594,983 S | 6/2009 | Price et al. |
| 7,540,872 B2 | 6/2009 | Schechter et al. |
| 7,543,730 B1 | 6/2009 | Marczyk |
| 7,544,200 B2 | 6/2009 | Houser |
| 7,550,216 B2 | 6/2009 | Ofer et al. |
| 7,553,309 B2 | 6/2009 | Buysse et al. |
| 7,559,452 B2 | 7/2009 | Wales et al. |
| 7,566,318 B2 | 7/2009 | Haefner |
| 7,567,012 B2 | 7/2009 | Namikawa |
| 7,582,086 B2 | 9/2009 | Privitera et al. |
| 7,582,087 B2 | 9/2009 | Tetzlaff et al. |
| 7,586,289 B2 | 9/2009 | Andruk et al. |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,599,743 B2 | 10/2009 | Hassler, Jr. et al. |
| 7,601,119 B2 | 10/2009 | Shahinian |
| 7,604,150 B2 | 10/2009 | Boudreaux |
| 7,608,083 B2 | 10/2009 | Lee et al. |
| 7,611,512 B2 | 11/2009 | Ein-Gal |
| 7,617,961 B2 | 11/2009 | Viola |
| 7,621,910 B2 | 11/2009 | Sugi |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,640,447 B2 | 12/2009 | Qiu |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,678,043 B2 | 3/2010 | Gilad |
| 7,678,069 B1 | 3/2010 | Baker et al. |
| 7,678,105 B2 | 3/2010 | McGreevy et al. |
| 7,686,804 B2 | 3/2010 | Johnson et al. |
| 7,691,095 B2 | 4/2010 | Bednarek et al. |
| 7,691,098 B2 | 4/2010 | Wallace et al. |
| 7,691,103 B2 | 4/2010 | Fernandez et al. |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,717,312 B2 | 5/2010 | Beetel |
| 7,717,914 B2 | 5/2010 | Kimura |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,725,214 B2 | 5/2010 | Diolaiti |
| D618,797 S | 6/2010 | Price et al. |
| 7,726,537 B2 | 6/2010 | Olson et al. |
| 7,744,615 B2 | 6/2010 | Couture |
| 7,751,115 B2 | 7/2010 | Song |
| 7,753,904 B2 | 7/2010 | Shelton, IV et al. |
| 7,753,908 B2 | 7/2010 | Swanson |
| 7,753,909 B2 | 7/2010 | Chapman et al. |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,775,972 B2 | 8/2010 | Brock et al. |
| 7,776,036 B2 | 8/2010 | Schechter et al. |
| 7,776,037 B2 | 8/2010 | Odom |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,663 B2 | 8/2010 | Shelton, IV |
| 7,789,283 B2 | 9/2010 | Shah |
| 7,789,878 B2 | 9/2010 | Dumbauld et al. |
| 7,789,883 B2 | 9/2010 | Takashino et al. |
| 7,793,814 B2 | 9/2010 | Racenet et al. |
| 7,799,027 B2 | 9/2010 | Hafner |
| 7,803,156 B2 | 9/2010 | Eder et al. |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| D627,066 S | 11/2010 | Romero |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,837,699 B2 | 11/2010 | Yamada et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,850,688 B2 | 12/2010 | Hafner |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| D631,965 S | 2/2011 | Price et al. |
| 7,877,852 B2 | 2/2011 | Unger et al. |
| 7,877,853 B2 | 2/2011 | Unger et al. |
| 7,879,035 B2 | 2/2011 | Garrison et al. |
| 7,879,070 B2 | 2/2011 | Ortiz et al. |
| 7,887,535 B2 | 2/2011 | Lands et al. |
| 7,892,606 B2 | 2/2011 | Thies et al. |
| 7,896,875 B2 | 3/2011 | Heim et al. |
| 7,896,878 B2 | 3/2011 | Johnson et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,922,953 B2 | 4/2011 | Guerra |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,942,303 B2 | 5/2011 | Shah |
| 7,942,868 B2 | 5/2011 | Cooper |
| 7,947,039 B2 | 5/2011 | Sartor |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |

(56) References Cited

U.S. PATENT DOCUMENTS

| | | |
|---|---|---|
| 7,963,963 B2 | 6/2011 | Francischelli et al. |
| 7,967,602 B2 | 6/2011 | Lindquist |
| 7,976,544 B2 | 7/2011 | McClurken et al. |
| 7,980,443 B2 | 7/2011 | Scheib et al. |
| 7,981,113 B2 | 7/2011 | Truckai et al. |
| 7,988,567 B2 | 8/2011 | Kim et al. |
| 7,997,278 B2 | 8/2011 | Utley et al. |
| 8,020,743 B2 | 9/2011 | Shelton, IV |
| 8,033,173 B2 | 10/2011 | Ehlert et al. |
| 8,038,612 B2 | 10/2011 | Paz |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,056,787 B2 | 11/2011 | Boudreaux et al. |
| 8,057,498 B2 | 11/2011 | Robertson |
| 8,058,771 B2 | 11/2011 | Giordano et al. |
| 8,061,014 B2 | 11/2011 | Smith et al. |
| 8,062,211 B2 | 11/2011 | Duval et al. |
| 8,066,167 B2 | 11/2011 | Measamer et al. |
| 8,070,036 B1 | 12/2011 | Knodel |
| 8,070,748 B2 | 12/2011 | Hixson et al. |
| 8,075,555 B2 | 12/2011 | Truckai et al. |
| 8,075,558 B2 | 12/2011 | Truckai et al. |
| 8,092,475 B2 | 1/2012 | Cotter et al. |
| 8,100,894 B2 | 1/2012 | Mucko et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,114,119 B2 | 2/2012 | Spivey et al. |
| 8,128,624 B2 | 3/2012 | Couture et al. |
| 8,128,657 B2 | 3/2012 | Shiono et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,940 B2 | 4/2012 | Johnson et al. |
| 8,177,784 B2 | 5/2012 | Van Wyk et al. |
| 8,177,794 B2 | 5/2012 | Cabrera et al. |
| 8,182,502 B2 | 5/2012 | Stulen et al. |
| 8,186,560 B2 | 5/2012 | Hess et al. |
| 8,187,166 B2 | 5/2012 | Kuth et al. |
| 8,187,267 B2 | 5/2012 | Pappone et al. |
| 8,192,433 B2 | 6/2012 | Johnson et al. |
| 8,197,472 B2 | 6/2012 | Lau et al. |
| 8,197,479 B2 | 6/2012 | Olson et al. |
| 8,197,494 B2 | 6/2012 | Jaggi et al. |
| 8,197,502 B2 | 6/2012 | Smith et al. |
| 8,206,212 B2 | 6/2012 | Iddings et al. |
| 8,221,415 B2 | 7/2012 | Francischelli |
| 8,221,416 B2 | 7/2012 | Townsend |
| 8,226,675 B2 | 7/2012 | Houser et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,244,368 B2 | 8/2012 | Sherman |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,257,352 B2 | 9/2012 | Lawes et al. |
| 8,257,377 B2 | 9/2012 | Wiener et al. |
| 8,262,563 B2 | 9/2012 | Bakos et al. |
| 8,267,300 B2 | 9/2012 | Boudreaux |
| 8,267,854 B2 | 9/2012 | Asada et al. |
| 8,267,935 B2 | 9/2012 | Couture et al. |
| 8,273,085 B2 | 9/2012 | Park et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,228 B2 | 10/2012 | Buysse et al. |
| 8,298,232 B2 | 10/2012 | Unger |
| 8,303,583 B2 | 11/2012 | Hosier et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,322,455 B2 | 12/2012 | Shelton, IV et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,053 B2 | 2/2013 | Orszulak |
| 8,377,059 B2 | 2/2013 | Deville et al. |
| 8,377,085 B2 | 2/2013 | Smith et al. |
| 8,382,754 B2 | 2/2013 | Odom et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,094 B2 | 3/2013 | Edwards et al. |
| 8,394,115 B2 | 3/2013 | Houser et al. |
| 8,397,971 B2 | 3/2013 | Yates et al. |
| 8,398,633 B2 | 3/2013 | Mueller |
| 8,403,926 B2 | 3/2013 | Nobis et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,076 B2 | 4/2013 | Pang et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,911 B2 | 5/2013 | Mueller |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,956 B2 | 6/2013 | McKenna et al. |
| 8,469,981 B2 | 6/2013 | Robertson et al. |
| 8,475,361 B2 | 7/2013 | Barlow et al. |
| 8,475,453 B2 | 7/2013 | Marczyk et al. |

(56) References Cited

U.S. PATENT DOCUMENTS

| | | |
|---|---|---|
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,625 B2 | 7/2013 | Horner |
| 8,496,682 B2 | 7/2013 | Guerra et al. |
| 8,512,336 B2 | 8/2013 | Couture |
| 8,512,364 B2 | 8/2013 | Kowalski et al. |
| 8,512,365 B2 | 8/2013 | Wiener et al. |
| 8,523,889 B2 | 9/2013 | Stulen et al. |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,542,501 B2 | 9/2013 | Kyono |
| 8,553,430 B2 | 10/2013 | Melanson et al. |
| 8,562,516 B2 | 10/2013 | Saadat et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,187 B2 | 11/2013 | Marion |
| 8,574,231 B2 | 11/2013 | Boudreaux et al. |
| 8,579,176 B2 | 11/2013 | Smith et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| D695,407 S | 12/2013 | Price et al. |
| 8,596,513 B2 | 12/2013 | Olson et al. |
| 8,597,182 B2 | 12/2013 | Stein et al. |
| 8,597,297 B2 | 12/2013 | Couture et al. |
| 8,608,044 B2 | 12/2013 | Hueil et al. |
| 8,613,383 B2 | 12/2013 | Beckman et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,632,539 B2 | 1/2014 | Twomey et al. |
| 8,636,648 B2 | 1/2014 | Gazdzinski |
| 8,636,736 B2 | 1/2014 | Yates et al. |
| 8,636,761 B2 | 1/2014 | Cunningham et al. |
| 8,638,428 B2 | 1/2014 | Brown |
| 8,640,788 B2 | 2/2014 | Dachs, II et al. |
| 8,641,712 B2 | 2/2014 | Couture |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,155 B2 | 2/2014 | Houser et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,668,691 B2 | 3/2014 | Heard |
| RE44,834 E | 4/2014 | Dumbauld et al. |
| 8,684,253 B2 | 4/2014 | Giordano et al. |
| 8,685,020 B2 | 4/2014 | Weizman et al. |
| 8,685,056 B2 | 4/2014 | Evans et al. |
| 8,696,662 B2 | 4/2014 | Eder et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,708,213 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,745,840 B2 | 6/2014 | Hempstead et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,770,459 B2 | 7/2014 | Racenet et al. |
| 8,784,418 B2 | 7/2014 | Romero |
| 8,789,740 B2 | 7/2014 | Baxter, III et al. |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,752 B2 | 8/2014 | Fortier et al. |
| 8,807,414 B2 | 8/2014 | Ross et al. |
| 8,808,319 B2 | 8/2014 | Houser et al. |
| 8,814,856 B2 | 8/2014 | Elmouelhi et al. |
| 8,814,865 B2 | 8/2014 | Reschke |
| 8,814,870 B2 | 8/2014 | Paraschiv et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,488 B2 | 9/2014 | Farritor et al. |
| 8,834,518 B2 | 9/2014 | Faller et al. |
| 8,845,630 B2 | 9/2014 | Mehta et al. |
| 8,851,354 B2 | 10/2014 | Swensgard et al. |
| 8,852,184 B2 | 10/2014 | Kucklick |
| 8,864,757 B2 | 10/2014 | Klimovitch et al. |
| 8,864,761 B2 | 10/2014 | Johnson et al. |
| 8,870,867 B2 | 10/2014 | Walberg et al. |
| 8,876,858 B2 | 11/2014 | Braun |
| 8,882,766 B2 | 11/2014 | Couture et al. |
| 8,882,791 B2 | 11/2014 | Stulen |
| 8,887,373 B2 | 11/2014 | Brandt et al. |
| 8,888,776 B2 | 11/2014 | Dietz et al. |
| 8,888,783 B2 | 11/2014 | Young |
| 8,888,809 B2 | 11/2014 | Davison et al. |
| 8,906,012 B2 | 12/2014 | Conley et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,414 B2 | 12/2014 | Stone et al. |
| 8,926,607 B2 | 1/2015 | Norvell et al. |
| 8,926,608 B2 | 1/2015 | Bacher et al. |
| 8,929,888 B2 | 1/2015 | Rao et al. |
| 8,931,682 B2 | 1/2015 | Timm et al. |
| 8,939,287 B2 | 1/2015 | Markovitch |
| 8,939,974 B2 | 1/2015 | Boudreaux et al. |
| 8,939,975 B2 | 1/2015 | Twomey et al. |
| 8,944,997 B2 | 2/2015 | Fernandez et al. |
| 8,945,125 B2 | 2/2015 | Schechter et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,332 B2 | 3/2015 | Farritor et al. |
| 8,974,453 B2 | 3/2015 | Wang |
| 8,978,845 B2 | 3/2015 | Kim |
| 8,979,838 B2 | 3/2015 | Woloszko et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,989,855 B2 | 3/2015 | Murphy et al. |
| 8,992,422 B2 | 3/2015 | Spivey et al. |
| 8,992,520 B2 | 3/2015 | Van Wyk et al. |
| 8,992,526 B2 | 3/2015 | Brodbeck et al. |

(56) References Cited

U.S. PATENT DOCUMENTS

| | | |
|---|---|---|
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,372 B2 | 4/2015 | Artale et al. |
| 9,023,035 B2 | 5/2015 | Allen, IV et al. |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,983 B2 | 5/2015 | Takashino et al. |
| 9,039,695 B2 | 5/2015 | Giordano et al. |
| 9,039,705 B2 | 5/2015 | Takashino |
| 9,039,731 B2 | 5/2015 | Joseph |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,113 B2 | 6/2015 | Bloom et al. |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,078,664 B2 | 7/2015 | Palmer et al. |
| 9,089,327 B2 | 7/2015 | Worrell et al. |
| 9,089,360 B2 | 7/2015 | Messerly et al. |
| 9,094,006 B2 | 7/2015 | Gravati et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,672 B2 | 8/2015 | Tetzlaff et al. |
| 9,113,889 B2 | 8/2015 | Reschke |
| 9,113,900 B2 | 8/2015 | Buysse et al. |
| 9,119,630 B2 | 9/2015 | Townsend et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,138,289 B2 | 9/2015 | Conley et al. |
| 9,149,324 B2 | 10/2015 | Huang et al. |
| 9,149,325 B2 | 10/2015 | Worrell et al. |
| 9,155,585 B2 | 10/2015 | Bales, Jr. et al. |
| 9,161,803 B2 | 10/2015 | Yates et al. |
| 9,168,054 B2 | 10/2015 | Turner et al. |
| 9,168,082 B2 | 10/2015 | Evans et al. |
| 9,168,085 B2 | 10/2015 | Juzkiw et al. |
| 9,168,089 B2 | 10/2015 | Buysse et al. |
| 9,179,912 B2 | 11/2015 | Yates et al. |
| 9,186,204 B2 | 11/2015 | Nishimura et al. |
| 9,187,758 B2 | 11/2015 | Cai et al. |
| 9,192,380 B2 | 11/2015 | Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,716 B2 | 12/2015 | Masuda et al. |
| 9,204,879 B2 | 12/2015 | Shelton, IV |
| 9,204,919 B2 | 12/2015 | Brandt et al. |
| 9,216,050 B2 | 12/2015 | Condie et al. |
| 9,220,559 B2 | 12/2015 | Worrell et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,571 B2 | 2/2016 | Twomey et al. |
| 9,265,926 B2 | 2/2016 | Strobl et al. |
| 9,271,784 B2 | 3/2016 | Evans et al. |
| 9,274,988 B2 | 3/2016 | Hsu et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,326,788 B2 | 5/2016 | Batross et al. |
| 9,326,812 B2 | 5/2016 | Waaler et al. |
| 9,333,025 B2 | 5/2016 | Monson et al. |
| 9,339,323 B2 | 5/2016 | Eder et al. |
| 9,339,326 B2 | 5/2016 | McCullagh et al. |
| 9,344,042 B2 | 5/2016 | Mao |
| 9,345,481 B2 | 5/2016 | Hall et al. |
| 9,345,900 B2 | 5/2016 | Wu et al. |
| 9,351,754 B2 | 5/2016 | Vakharia et al. |
| 9,358,061 B2 | 6/2016 | Plascencia, Jr. et al. |
| 9,358,065 B2 | 6/2016 | Ladtkow et al. |
| 9,364,225 B2 | 6/2016 | Sniffin et al. |
| 9,364,230 B2 | 6/2016 | Shelton, IV et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,381,060 B2 | 7/2016 | Artale et al. |
| 9,386,983 B2 | 7/2016 | Swensgard et al. |
| 9,393,037 B2 | 7/2016 | Olson et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,456,876 B2 | 10/2016 | Hagn |
| 9,468,490 B2 | 10/2016 | Twomey et al. |
| 9,492,224 B2 | 11/2016 | Boudreaux et al. |
| 9,504,524 B2 | 11/2016 | Behnke, II |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,549,663 B2 | 1/2017 | Larkin |
| 9,554,845 B2 | 1/2017 | Arts |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,585,709 B2 | 3/2017 | Krapohl |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,810 B2 | 4/2017 | Hart et al. |
| 9,627,120 B2 | 4/2017 | Scott et al. |
| 9,629,629 B2 | 4/2017 | Leimbach et al. |
| 9,642,669 B2 | 5/2017 | Takashino et al. |
| 9,649,111 B2 | 5/2017 | Shelton, IV et al. |
| 9,649,144 B2 | 5/2017 | Aluru et al. |
| 9,649,151 B2 | 5/2017 | Goodman et al. |
| 9,662,131 B2 | 5/2017 | Omori et al. |
| 9,668,806 B2 | 6/2017 | Unger et al. |
| 9,687,295 B2 | 6/2017 | Joseph |
| 9,700,339 B2 | 7/2017 | Nield |
| 9,707,005 B2 | 7/2017 | Strobl et al. |
| 9,707,027 B2 | 7/2017 | Ruddenklau et al. |
| 9,707,030 B2 | 7/2017 | Davison et al. |
| 9,713,489 B2 | 7/2017 | Woloszko et al. |
| 9,713,491 B2 | 7/2017 | Roy et al. |
| 9,724,118 B2 | 8/2017 | Schulte et al. |
| 9,724,152 B2 | 8/2017 | Horlle et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,757,128 B2 | 9/2017 | Baber et al. |
| 9,757,142 B2 | 9/2017 | Shimizu |
| 9,757,186 B2 | 9/2017 | Boudreaux et al. |
| 9,775,665 B2 | 10/2017 | Ellman |
| 9,775,669 B2 | 10/2017 | Marczyk et al. |

(56) References Cited

U.S. PATENT DOCUMENTS

| | | |
|---|---|---|
| 9,782,214 B2 | 10/2017 | Houser et al. |
| 9,782,220 B2 | 10/2017 | Mark et al. |
| 9,788,891 B2 | 10/2017 | Christian et al. |
| 9,795,436 B2 | 10/2017 | Yates et al. |
| 9,802,033 B2 | 10/2017 | Hibner et al. |
| 9,808,244 B2 | 11/2017 | Leimbach et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,833,239 B2 | 12/2017 | Yates et al. |
| 9,848,937 B2 | 12/2017 | Trees et al. |
| 9,848,939 B2 | 12/2017 | Mayer et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,877,782 B2 | 1/2018 | Voegele et al. |
| 9,888,954 B2 | 2/2018 | Van Wyk et al. |
| 9,888,958 B2 | 2/2018 | Evans et al. |
| 9,901,359 B2 | 2/2018 | Faller et al. |
| 9,901,390 B2 | 2/2018 | Allen, IV et al. |
| 9,901,754 B2 | 2/2018 | Yamada |
| 9,907,563 B2 | 3/2018 | Germain et al. |
| 9,913,680 B2 | 3/2018 | Voegele et al. |
| 9,918,730 B2 | 3/2018 | Trees et al. |
| 9,918,773 B2 | 3/2018 | Ishikawa et al. |
| 9,931,157 B2 | 4/2018 | Strobl et al. |
| 9,937,001 B2 | 4/2018 | Nakamura |
| 9,943,357 B2 | 4/2018 | Cunningham et al. |
| 9,949,620 B2 | 4/2018 | Duval et al. |
| 9,949,785 B2 | 4/2018 | Price et al. |
| 9,949,788 B2 | 4/2018 | Boudreaux |
| 9,974,539 B2 | 5/2018 | Yates et al. |
| 9,993,289 B2 | 6/2018 | Sobajima et al. |
| 10,010,339 B2 | 7/2018 | Witt et al. |
| 10,016,207 B2 | 7/2018 | Suzuki et al. |
| 10,022,142 B2 | 7/2018 | Aranyi et al. |
| 10,034,707 B2 | 7/2018 | Papaioannou et al. |
| 10,041,822 B2 | 8/2018 | Zemlok |
| 10,052,044 B2 | 8/2018 | Shelton, IV et al. |
| 10,058,376 B2 | 8/2018 | Horner et al. |
| 10,070,916 B2 | 9/2018 | Artale |
| 10,080,606 B2 | 9/2018 | Kappus et al. |
| 10,092,310 B2 | 10/2018 | Boudreaux et al. |
| 10,092,348 B2 | 10/2018 | Boudreaux |
| 10,092,350 B2 | 10/2018 | Rothweiler et al. |
| 10,105,174 B2 | 10/2018 | Krapohl |
| 10,111,699 B2 | 10/2018 | Boudreaux |
| 10,117,702 B2 | 11/2018 | Danziger et al. |
| 10,130,410 B2 | 11/2018 | Strobl et al. |
| 10,130,414 B2 | 11/2018 | Weiler et al. |
| 10,135,242 B2 | 11/2018 | Baber et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,194,911 B2 | 2/2019 | Miller et al. |
| 10,194,972 B2 | 2/2019 | Yates et al. |
| 10,194,976 B2 | 2/2019 | Boudreaux |
| 10,194,977 B2 | 2/2019 | Yang |
| 10,211,586 B2 | 2/2019 | Adams et al. |
| 10,231,776 B2 | 3/2019 | Artale et al. |
| 10,231,777 B2 | 3/2019 | Brandt et al. |
| 10,238,387 B2 | 3/2019 | Yates et al. |
| 10,245,095 B2 | 4/2019 | Boudreaux |
| 10,258,404 B2 | 4/2019 | Wang |
| 10,265,118 B2 | 4/2019 | Gerhardt |
| 10,278,721 B2 | 5/2019 | Dietz et al. |
| 10,307,203 B2 | 6/2019 | Wyatt |
| 10,314,638 B2 | 6/2019 | Gee et al. |
| 10,321,950 B2 | 6/2019 | Yates et al. |
| 10,342,602 B2 | 7/2019 | Strobl et al. |
| 10,413,352 B2 | 9/2019 | Thomas et al. |
| 10,420,601 B2 | 9/2019 | Marion et al. |
| 10,420,607 B2 | 9/2019 | Woloszko et al. |
| 10,426,873 B2 | 10/2019 | Schultz |
| 10,433,900 B2 | 10/2019 | Harris et al. |
| 10,441,345 B2 | 10/2019 | Aldridge et al. |
| 10,463,421 B2 | 11/2019 | Boudreaux et al. |
| 10,478,243 B2 | 11/2019 | Couture et al. |
| 10,485,607 B2 | 11/2019 | Strobl et al. |
| 10,524,852 B1 | 1/2020 | Cagle et al. |
| 10,524,854 B2 | 1/2020 | Woodruff et al. |
| 10,568,682 B2 | 2/2020 | Dycus et al. |
| 10,575,868 B2 | 3/2020 | Hall et al. |
| 10,595,929 B2 | 3/2020 | Boudreaux et al. |
| 10,603,103 B2 | 3/2020 | Thomas et al. |
| 10,603,117 B2 | 3/2020 | Schings et al. |
| 10,639,092 B2 | 5/2020 | Corbett et al. |
| 10,646,269 B2 | 5/2020 | Worrell et al. |
| 10,675,082 B2 | 6/2020 | Shelton, IV et al. |
| 10,702,329 B2 | 7/2020 | Strobl et al. |
| 10,716,614 B2 | 7/2020 | Yates et al. |
| 10,751,109 B2 | 8/2020 | Yates et al. |
| 10,751,110 B2 | 8/2020 | Ding |
| 10,751,117 B2 * | 8/2020 | Witt ................. A61B 18/148 |
| 10,758,294 B2 | 9/2020 | Jones |
| 10,779,876 B2 | 9/2020 | Monson et al. |
| 10,799,284 B2 | 10/2020 | Renner et al. |
| 10,813,640 B2 | 10/2020 | Adams et al. |
| 10,820,938 B2 | 11/2020 | Fischer et al. |
| 10,856,934 B2 | 12/2020 | Trees et al. |
| 10,881,449 B2 | 1/2021 | Boudreaux et al. |
| 10,903,685 B2 | 1/2021 | Yates et al. |
| 10,912,600 B2 | 2/2021 | Kitagawa et al. |
| 10,959,771 B2 | 3/2021 | Boudreaux et al. |
| 10,959,806 B2 | 3/2021 | Hibner et al. |
| 10,966,779 B2 | 4/2021 | Hart et al. |
| 10,987,156 B2 | 4/2021 | Trees et al. |
| 11,013,528 B2 | 5/2021 | Isosaki et al. |
| 11,033,323 B2 | 6/2021 | Witt et al. |
| 11,033,325 B2 | 6/2021 | Yates et al. |
| 11,090,103 B2 | 8/2021 | Ruddenklau et al. |
| 11,266,430 B2 | 3/2022 | Clauda et al. |
| 11,653,920 B2 | 5/2023 | Shelton, IV et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0077550 A1 | 6/2002 | Rabiner et al. |
| 2002/0095175 A1 | 7/2002 | Brock et al. |
| 2002/0107517 A1 | 8/2002 | Witt et al. |
| 2002/0133149 A1 | 9/2002 | Bessette |
| 2002/0156493 A1 | 10/2002 | Houser et al. |
| 2003/0014053 A1 | 1/2003 | Nguyen et al. |
| 2003/0055443 A1 | 3/2003 | Spotnitz |
| 2003/0066938 A1 | 4/2003 | Zimmerman |
| 2003/0109875 A1 | 6/2003 | Tetzlaff et al. |
| 2003/0114731 A1 | 6/2003 | Cadeddu et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144660 A1 | 7/2003 | Mollenauer |
| 2003/0158548 A1 | 8/2003 | Phan et al. |
| 2003/0171747 A1 | 9/2003 | Kanehira et al. |
| 2003/0181910 A1 | 9/2003 | Dycus et al. |
| 2003/0204199 A1 | 10/2003 | Novak et al. |
| 2003/0212332 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0092992 A1 | 5/2004 | Adams et al. |
| 2004/0093039 A1 | 5/2004 | Schumert |
| 2004/0097919 A1 | 5/2004 | Wellman et al. |
| 2004/0097996 A1 | 5/2004 | Rabiner et al. |
| 2004/0102804 A1 | 5/2004 | Chin |
| 2004/0133089 A1 | 7/2004 | Kilcoyne et al. |
| 2004/0138621 A1 | 7/2004 | Jahns et al. |

(56) References Cited

U.S. PATENT DOCUMENTS

| | | |
|---|---|---|
| 2004/0167508 A1 | 8/2004 | Wham et al. |
| 2004/0193150 A1 | 9/2004 | Sharkey et al. |
| 2004/0199193 A1 | 10/2004 | Hayashi et al. |
| 2004/0249367 A1 | 12/2004 | Saadat et al. |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2005/0015125 A1 | 1/2005 | Mioduski et al. |
| 2005/0033278 A1 | 2/2005 | McClurken et al. |
| 2005/0033337 A1 | 2/2005 | Muir et al. |
| 2005/0090817 A1 | 4/2005 | Phan |
| 2005/0096502 A1 | 5/2005 | Khalili |
| 2005/0119640 A1 | 6/2005 | Sverduk et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0192610 A1 | 9/2005 | Houser et al. |
| 2005/0215858 A1 | 9/2005 | Vail |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0272972 A1 | 12/2005 | Iddan |
| 2005/0273139 A1 | 12/2005 | Krauss et al. |
| 2005/0288555 A1 | 12/2005 | Binmoeller |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0106379 A1 | 5/2006 | O'Brien et al. |
| 2006/0159731 A1 | 7/2006 | Shoshan |
| 2006/0190034 A1 | 8/2006 | Nishizawa et al. |
| 2006/0211943 A1 | 9/2006 | Beaupre |
| 2006/0253050 A1 | 11/2006 | Yoshimine et al. |
| 2006/0270916 A1 | 11/2006 | Skwarek et al. |
| 2006/0293656 A1 | 12/2006 | Shadduck et al. |
| 2007/0008744 A1 | 1/2007 | Heo et al. |
| 2007/0010709 A1 | 1/2007 | Reinschke |
| 2007/0016235 A1 | 1/2007 | Tanaka et al. |
| 2007/0016236 A1 | 1/2007 | Beaupre |
| 2007/0020065 A1 | 1/2007 | Kirby |
| 2007/0032701 A1 | 2/2007 | Fowler et al. |
| 2007/0032704 A1 | 2/2007 | Gandini et al. |
| 2007/0032785 A1 | 2/2007 | Diederich et al. |
| 2007/0051766 A1 | 3/2007 | Spencer |
| 2007/0055228 A1 | 3/2007 | Berg et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0106317 A1 | 5/2007 | Shelton et al. |
| 2007/0118115 A1 | 5/2007 | Artale et al. |
| 2007/0123748 A1 | 5/2007 | Meglan |
| 2007/0130771 A1 | 6/2007 | Ehlert et al. |
| 2007/0135686 A1 | 6/2007 | Pruitt et al. |
| 2007/0149881 A1 | 6/2007 | Rabin |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0182842 A1 | 8/2007 | Sonnenschein et al. |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0270651 A1 | 11/2007 | Gilad et al. |
| 2007/0275348 A1 | 11/2007 | Lemon |
| 2007/0276424 A1 | 11/2007 | Mikkaichi et al. |
| 2007/0287933 A1 | 12/2007 | Phan et al. |
| 2008/0015413 A1 | 1/2008 | Barlow et al. |
| 2008/0015575 A1 | 1/2008 | Odom et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0082039 A1 | 4/2008 | Babaev |
| 2008/0082098 A1 | 4/2008 | Tanaka et al. |
| 2008/0103495 A1 | 5/2008 | Mihori et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208231 A1 | 8/2008 | Ota et al. |
| 2008/0214967 A1 | 9/2008 | Aranyi et al. |
| 2008/0228179 A1 | 9/2008 | Eder et al. |
| 2008/0234709 A1 | 9/2008 | Houser |
| 2008/0281200 A1 | 11/2008 | Voic et al. |
| 2008/0281315 A1 | 11/2008 | Gines |
| 2008/0287948 A1 | 11/2008 | Newton et al. |
| 2008/0300588 A1 | 12/2008 | Groth et al. |
| 2008/0312502 A1 | 12/2008 | Swain et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0114701 A1 | 5/2009 | Zemlok et al. |
| 2009/0143678 A1 | 6/2009 | Keast et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0248021 A1 | 10/2009 | McKenna |
| 2009/0254080 A1 | 10/2009 | Honda |
| 2009/0264879 A1 | 10/2009 | Mcclurken et al. |
| 2009/0270771 A1 | 10/2009 | Takahashi |
| 2009/0270853 A1 | 10/2009 | Yachi et al. |
| 2009/0287205 A1 | 11/2009 | Ingle |
| 2010/0022824 A1 | 1/2010 | Cybulski et al. |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0158307 A1 | 6/2010 | Kubota et al. |
| 2010/0187283 A1 | 7/2010 | Crainich et al. |
| 2010/0204802 A1 | 8/2010 | Wilson et al. |
| 2010/0222752 A1 | 9/2010 | Collins, Jr. et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2011/0009857 A1 | 1/2011 | Subramaniam et al. |
| 2011/0028964 A1 | 2/2011 | Edwards |
| 2011/0087224 A1 | 4/2011 | Cadeddu et al. |
| 2011/0118601 A1 | 5/2011 | Barnes et al. |
| 2011/0125151 A1 | 5/2011 | Strauss et al. |
| 2011/0257680 A1 | 10/2011 | Reschke et al. |
| 2011/0270245 A1 | 11/2011 | Horner et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0059374 A1 | 3/2012 | Johnson et al. |
| 2012/0078244 A1 | 3/2012 | Worrell et al. |
| 2012/0080334 A1 | 4/2012 | Shelton, IV et al. |
| 2012/0085358 A1 | 4/2012 | Cadeddu et al. |
| 2012/0109186 A1 | 5/2012 | Parrott et al. |

(56) References Cited

U.S. PATENT DOCUMENTS

| | | |
|---|---|---|
| 2012/0116222 A1 | 5/2012 | Sawada et al. |
| 2012/0116265 A1 | 5/2012 | Houser et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0190753 A1 | 7/2013 | Garrison et al. |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0039493 A1 | 2/2014 | Conley et al. |
| 2014/0131419 A1 | 5/2014 | Bettuchi |
| 2014/0194864 A1 | 7/2014 | Martin et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0263541 A1 | 9/2014 | Leimbach et al. |
| 2014/0263552 A1 | 9/2014 | Hall et al. |
| 2015/0032150 A1 | 1/2015 | Ishida et al. |
| 2015/0080876 A1 | 3/2015 | Worrell et al. |
| 2015/0257819 A1 | 9/2015 | Dycus et al. |
| 2015/0272571 A1 | 10/2015 | Leimbach et al. |
| 2015/0272659 A1 | 10/2015 | Boudreaux et al. |
| 2015/0327918 A1 | 11/2015 | Sobajima et al. |
| 2016/0045248 A1 | 2/2016 | Unger et al. |
| 2016/0051316 A1 | 2/2016 | Boudreaux |
| 2016/0066980 A1 | 3/2016 | Schall et al. |
| 2016/0100747 A1 | 4/2016 | Nitsan et al. |
| 2016/0175029 A1 | 6/2016 | Witt et al. |
| 2016/0270842 A1 | 9/2016 | Strobl et al. |
| 2016/0296270 A1 | 10/2016 | Strobl et al. |
| 2017/0105786 A1 | 4/2017 | Scheib et al. |
| 2017/0105787 A1 | 4/2017 | Witt et al. |
| 2017/0135751 A1 | 5/2017 | Rothweiler et al. |
| 2017/0164972 A1 | 6/2017 | Johnson et al. |
| 2017/0312018 A1 | 11/2017 | Trees et al. |
| 2017/0325878 A1 | 11/2017 | Messerly et al. |
| 2017/0325886 A1 | 11/2017 | Graham et al. |
| 2017/0348043 A1 | 12/2017 | Wang et al. |
| 2018/0125571 A1 | 5/2018 | Witt et al. |
| 2018/0161034 A1 | 6/2018 | Scheib et al. |
| 2018/0235626 A1 | 8/2018 | Shelton, IV et al. |
| 2018/0280075 A1 | 10/2018 | Nott et al. |
| 2019/0000470 A1 | 1/2019 | Yates et al. |
| 2019/0000536 A1 | 1/2019 | Yates et al. |
| 2019/0059980 A1 | 2/2019 | Shelton, IV et al. |
| 2019/0099209 A1 | 4/2019 | Witt et al. |
| 2019/0099212 A1 | 4/2019 | Davison et al. |
| 2019/0099217 A1 | 4/2019 | Witt et al. |
| 2019/0200998 A1 | 7/2019 | Shelton, IV et al. |
| 2019/0314015 A1 | 10/2019 | Shelton, IV et al. |
| 2020/0352636 A1 | 11/2020 | Batchelor et al. |
| 2021/0100605 A1 | 4/2021 | Renner et al. |
| 2021/0196334 A1 | 7/2021 | Sarley et al. |
| 2021/0196346 A1 | 7/2021 | Leuck et al. |
| 2021/0196353 A1 | 7/2021 | Gee et al. |
| 2021/0338309 A1 | 11/2021 | Witt et al. |
| 2022/0167975 A1 | 6/2022 | Shelton, IV et al. |
| 2022/0168038 A1 | 6/2022 | Shelton, IV et al. |
| 2022/0395318 A1 | 12/2022 | Nott et al. |
| 2023/0027481 A1 | 1/2023 | Davison et al. |

FOREIGN PATENT DOCUMENTS

| | | |
|---|---|---|
| CN | 2868227 Y | 2/2007 |
| DE | 4300307 A1 | 7/1994 |
| DE | 29623113 U1 | 10/1997 |
| DE | 20004812 U1 | 9/2000 |
| DE | 10201569 A1 | 7/2003 |
| DE | 102005032371 A1 | 1/2007 |
| EP | 0171967 A2 | 2/1986 |
| EP | 0705571 A1 | 4/1996 |
| EP | 1862133 A1 | 12/2007 |
| EP | 2060238 A1 | 5/2009 |
| EP | 1747761 B1 | 10/2009 |
| EP | 1767164 B1 | 1/2013 |
| EP | 2578172 A2 | 4/2013 |
| ES | 2419159 A2 | 8/2013 |
| GB | 2032221 A | 4/1980 |
| JP | S537994 A | 1/1978 |
| JP | H08229050 A | 9/1996 |
| JP | 2002186627 A | 7/2002 |
| JP | 2009213878 A | 9/2009 |
| JP | 2010057926 A | 3/2010 |
| JP | 2012019846 A | 2/2012 |
| WO | WO-8103272 A1 | 11/1981 |
| WO | WO-9314708 A1 | 8/1993 |
| WO | WO-9800069 A1 | 1/1998 |
| WO | WO-9923960 A1 | 5/1999 |
| WO | WO-0024330 A1 | 5/2000 |
| WO | WO-0128444 A1 | 4/2001 |
| WO | WO-02080794 A1 | 10/2002 |
| WO | WO-2004078051 A2 | 9/2004 |
| WO | WO-2008130793 A1 | 10/2008 |
| WO | WO-2009067649 A2 | 5/2009 |
| WO | WO-2010104755 A1 | 9/2010 |
| WO | WO-2011008672 A2 | 1/2011 |
| WO | WO-2011044343 A2 | 4/2011 |
| WO | WO-2011144911 A1 | 11/2011 |
| WO | WO-2012044606 A2 | 4/2012 |
| WO | WO-2012061638 A1 | 5/2012 |
| WO | WO-2013131823 A1 | 9/2013 |
| WO | WO-2016088017 A1 | 6/2016 |

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

(56) References Cited

OTHER PUBLICATIONS

Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Glaser and Subak-Sharpe, Integrated Circuit Engineering, Addison-Wesley Publishing, Reading, MA (1979). (book—not attached).
Chen et al., "Heat-induced changes in the mechanics of a collagenous tissue: pseudoelastic behavior at 37° C.," Journal of Biomechanics, 31, pp. 211-216 (1998).
Kurt Gieck & Reiner Gieck, *Engineering Formulas* § Z.7 (7th ed. 1997).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . . , accessed Aug. 25, 2009.
Abbott, et al. Proceedings of the 2007 IEEEIRDJ International Conference on Intelligent Robots and Systems. 410-416, 2007.
Cadeddu et al., "Magnetic positioning system for trocarless laparoscopic instruments," American College of Surgeons Poster, 2004.
Cadeddu et al., "Novel magnetically guided intra-abdominal camera to facilitate laparoendoscopic single site surgery: initial human experience," Surgical Endoscopy, SAGES Oral Manuscript, 2009.
Cadeddu et al., "Transabdominal magnetic anchoring system for trocar-less laparoscopic surgery," American Urological Association Poster, 2002.
Cadeddu et al., "Transabdominal magnetic anchoring system for trocar-less laparoscopic surgery," Journal of Urology Abstract, 2002.
Castellvi et al., "Completely transvaginal NOTES cholecystectomy in a porcine model using novel endoscopic instrumentation," Accepted for Poster Presentation, SAGES Annual Meeting, 2009.
Castellvi et al., "Hybrid transgastric NOTES cholecystectomy in a porcine model using a magnetically anchored cautery and novel instrumentation," Submitted for Presentation, ASGE, 2009.
Castellvi et al., "Hybrid transvaginal NOTES sleeve gastrectomy in a porcine model using a magnetically anchored camera and novel instrumentation," Accepted for Poster Presentation, SAGES Annual Meeting, 2009.
Duchene et al., "Magnetic positioning system for trocarless laparoscopic instruments," Engineering and Urology Society Poster, 2004.
Fernandez et al., "Development of a transabdominal anchoring system for trocar-less laparoscopic surgery," ASME Proceedings of/MECE, 2003.
Gedeon et al., "Maximizing coupling strength of magnetically anchored notes instruments: How thick can we go?" Submittedfor Presentation, Poster, SAGES Annual Meeting, 2008.
Gedeon et al., "Maximizing coupling strength of magnetically anchored notes instruments: How thick can we go?" SAGES Annual Meeting Poster, 2008.
Park et al., "Trocar-less Instrumentation for Laparoscopy: Magnetic Positioning of Intra-Abdominal Camera and Retractor", Annals of Surgery, vol. 245, No. 3, pp. 379-384, Mar. 2007.
Peirs et al., "A miniature manipulator for integration in self-propelling endoscope," Sensors and Actuators, 92:343-9, 2001.
Raman et al., "Complete transvaginal NOTES nephrectomy using magnetically anchored instrumentation," Journal of Endourology, 23(3):, 2009.367-371,2009.
Rapaccini et al., "Gastric Wall Thickness in Normal and Neoplastic Subjects: A Prospective Study Performed by Abdominal Ultrasound", Gastrointestinal Radiology, vol. 13, pp. 197-199. 1988.
Scott et al., "A randomized comparison of laparoscopic, flexible endoscopic, and wired and wireless magnetic NOTES cameras on ex-vivo and in-vivo surgical performance," Digestive Disease Week (DDW), American Society for Gastrointestinal Endoscopy (ASGE) Annual Meeting Abstract, 2008.
Scott et al., "Completely transvaginal NOTES cholecystectomy using magnetically anchored instruments," Surg. Endosc., 21:2308-2316, 2007.
Scott et al., "Evaluation of a novel air seal access port for transvaginal notes cholecystectomy," Submitted for Presentation, SAGES Annual Meeting, 2008.
Scott et al., "Magnetically anchored instruments for transgastric endoscopic surgery," Oral Presentation for SAGES Annual Meeting, Emerging Technology Oral Abstract ET005, 2006.
Scott et al., "Optimizing magnetically anchored camera, light source, graspers, and cautery dissector for transvaginal notes cholecystectomy," Submitted for Presentation, SAGES Annual Meeting, 2008.
Scott et al., "Short-term survival outcomes following transvaginal NOTES cholecystectomy using magnetically anchored instruments," Oral Presentation, ASGE Annual Meeting/DDW, 2007.
Scott et al., "Trans gastric, transcolonic, and transvaginal cholecystectomy using magnetically anchored instruments," SAGES Annual Meeting Poster, 2007.
Scott et al., "Transvaginal NOTES cholecystectomy using magnetically anchored instruments," Abstract for Video Submission, ASGE II1h Annual Video Forum, 2007.
Scott et al., "Transvaginal single access 'pure' NOTES sleeve gastrectomy using a deployable magnetically anchored video camera," Digestive Disease Week (DDW), American Society for Gastrointestinal Endoscopy (ASGE) Annual Meeting Poster, 2008.
Swain et al., "Linear stapler formation of ileo-rectal, entero-enteral and gastrojejunal anastomoses during dual and single access 'pure' NOTES procedures: Methods, magnets and stapler modifications," Digestive Disease Week (DDW), American Society for Gastrointestinal Endoscopy (ASGE) Annual Meeting Abstract, 2008.
Swain et al., "Wireless endosurgery for NOTES," Digestive Disease Week (DDW), American Society for Gastrointestinal Endoscopy (ASGE) Annual Meeting Abstract, 2008.
Tang et al., "Live video manipulator for endoscopy and natural orifice transluminal endoscopic surgery (with videos)," Gastrointestinal Endoscopy, 68:559-564, 2008.
Zeltser et al., "Single trocar laparoscopic nephrectomy using magnetic anchoring and guidance system in the porcine model," The Journal of Urology, 178:288-291, 2007.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas ™ Hand Switching Instruments, dated Dec. 2008 (2 pages).
Covidien Brochure, The LigaSure ™ 5 mm Blunt Tip Sealer/Divider Family, dated Apr. 2013 (2 pages).
Covidien Brochure, The LigaSure Precise ™ Instrument, dated Mar. 2011 (2 pages).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Wright, et al., "Time-Temperature Equivalence of Heat-Induced Changes in Cells and Proteins," Feb. 1998. ASME Journal of Biomechanical Engineering, vol. 120, pp. 22-26.

(56) References Cited

OTHER PUBLICATIONS

Douglas, S.C. "Introduction to Adaptive Filter". Digital Signal Processing Handbook. Ed. Vijay K. Madisetti and Douglas B. Williams. Boca Raton: CRC Press LLC, 1999.

Jang, J. et al. "Neuro-fuzzy and Soft Computing." Prentice Hall, 1997, pp. 13-89, 199-293, 335-393, 453-496, 535-549.

Erbe Electrosurgery VIO® 200 S, (2012), p. 7, 12 pages, accessed Mar. 31, 2014 at http://www.erbe-med.com/erbe/media/Marketing materialien/85140170 ERBE EN VIO 200 S D027541.

Leonard I. Malis, M.D., "The Value of Irrigation During Bipolar Coagulation," 1989.

AST Products, Inc., "Principles of Video Contact Angle Analysis," 20 pages, (2006).

Lim et al., "A Review of Mechanism Used in Laparoscopic Surgical Instruments," Mechanism and Machine Theory, vol. 38, pp. 1133-1147, (2003).

F. A. Duck, "Optical Properties of Tissue Including Ultraviolet and Infrared Radiation," pp. 43-71 in Physical Properties of Tissue (1990).

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

Campbell et al, "Thermal Imaging in Surgery," p. 19-3, in Medical Infrared Imaging, N. A. Diakides and J. D. Bronzino, Eds. (2008).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Technology Overview, printed from www.harmonicscalpel.com, Internet site, website accessed on Jun. 13, 2007, (3 pages).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

Hörmann et al., "Reversible and irreversible denaturation of collagen fibers." Biochemistry, 10, pp. 932-937 (1971).

Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

\* cited by examiner

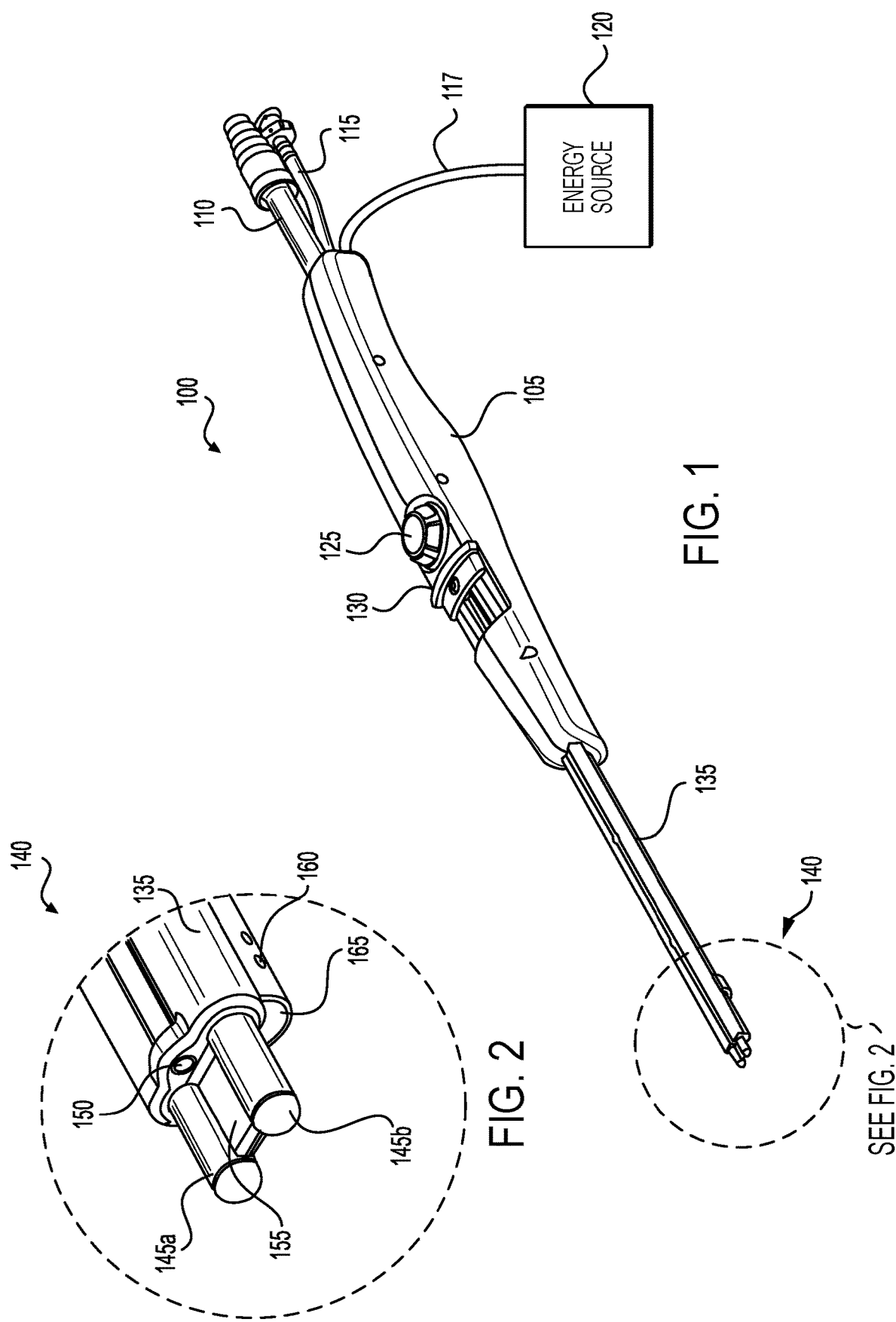

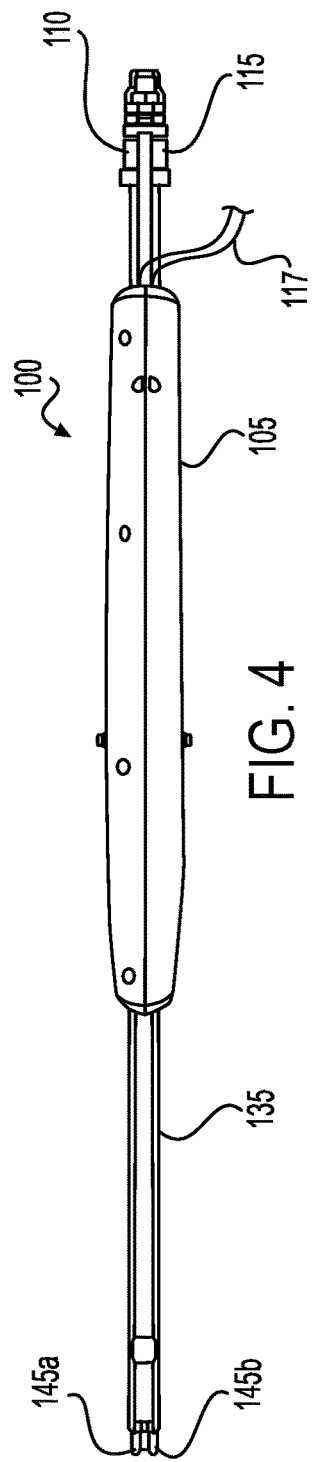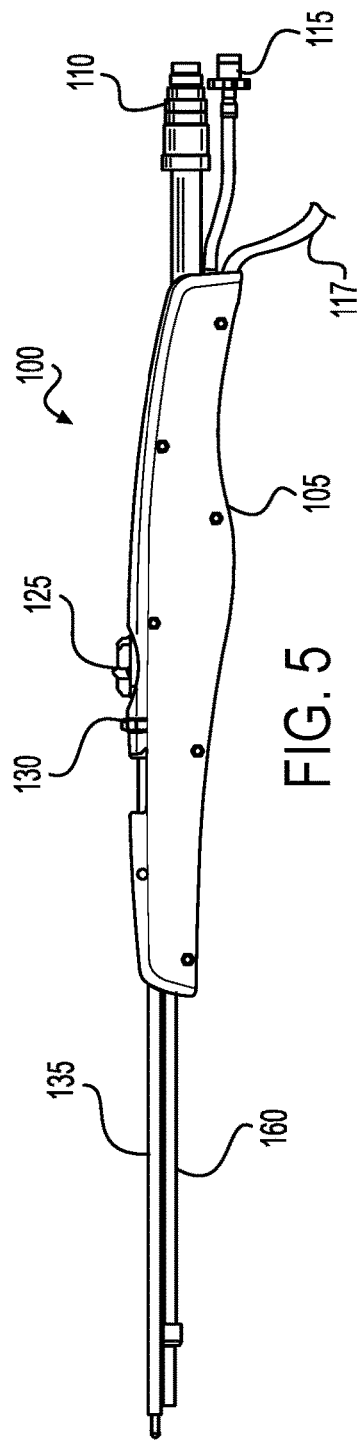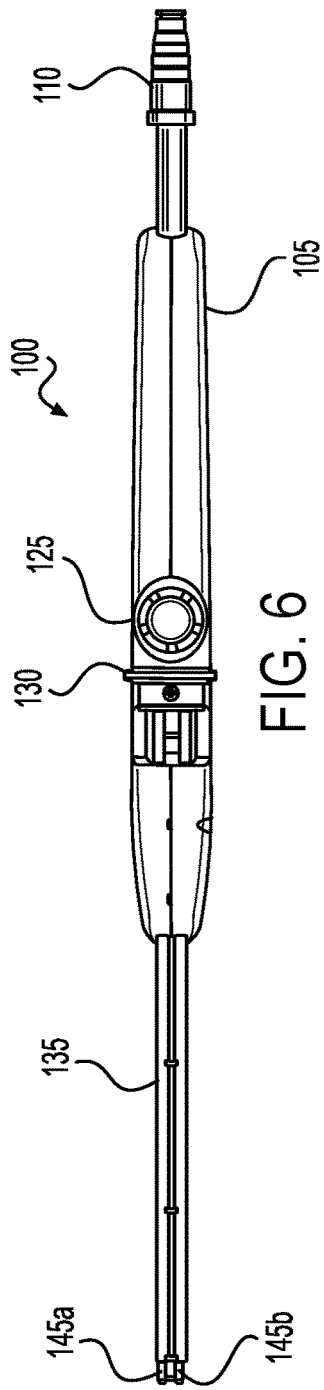

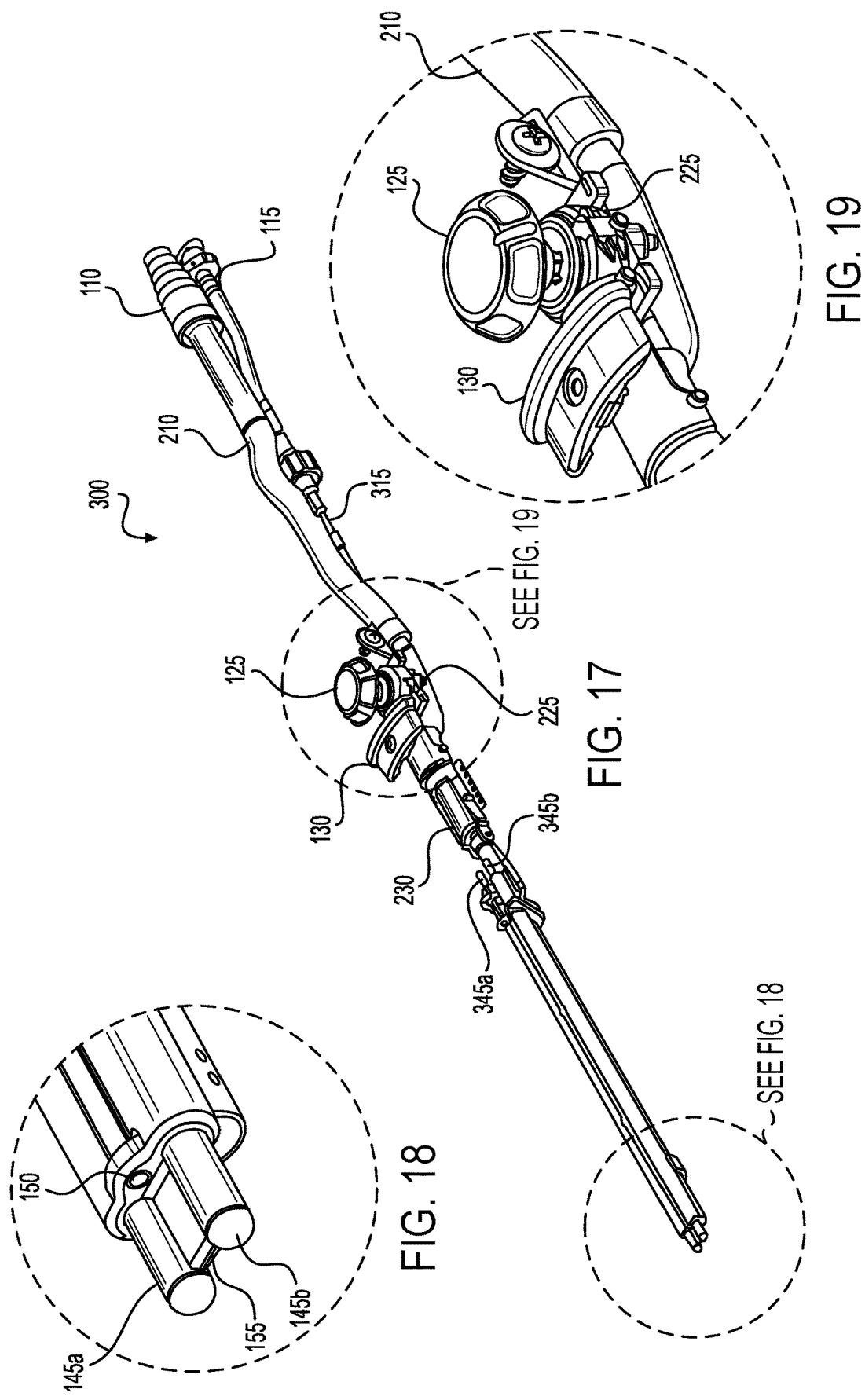

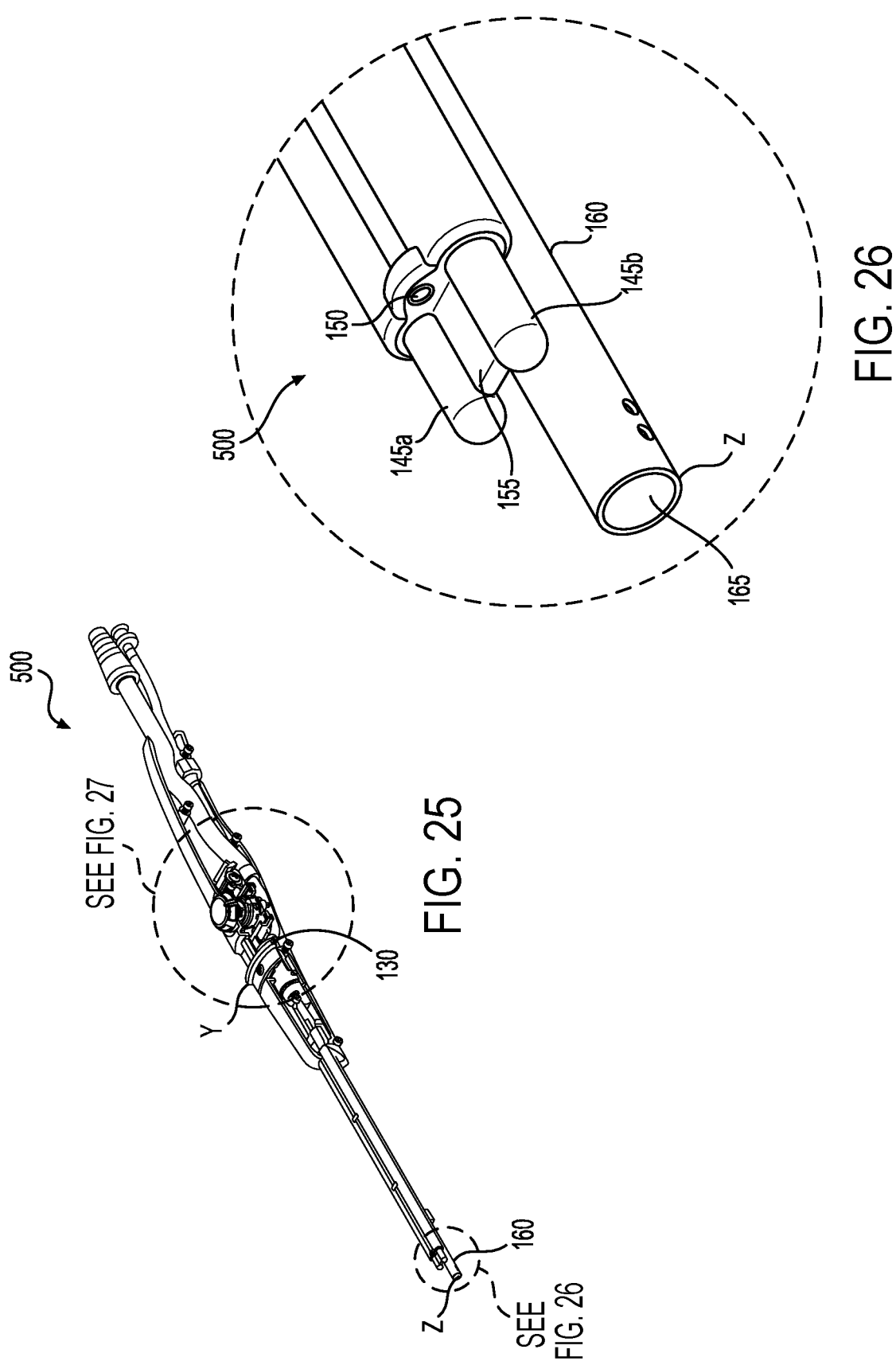

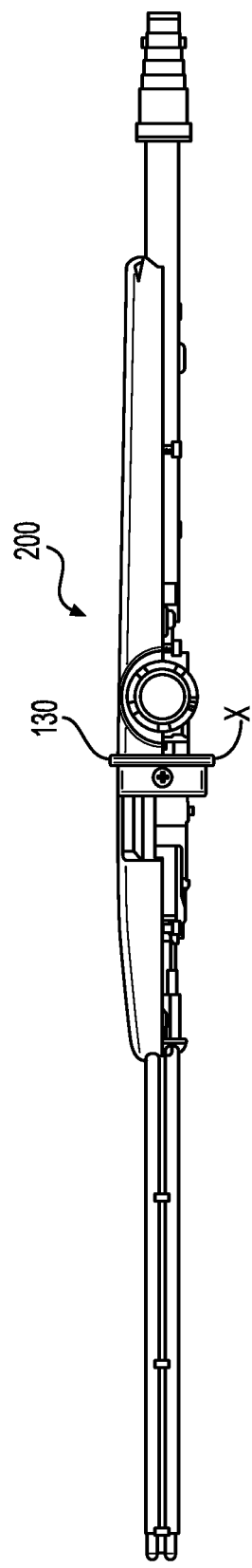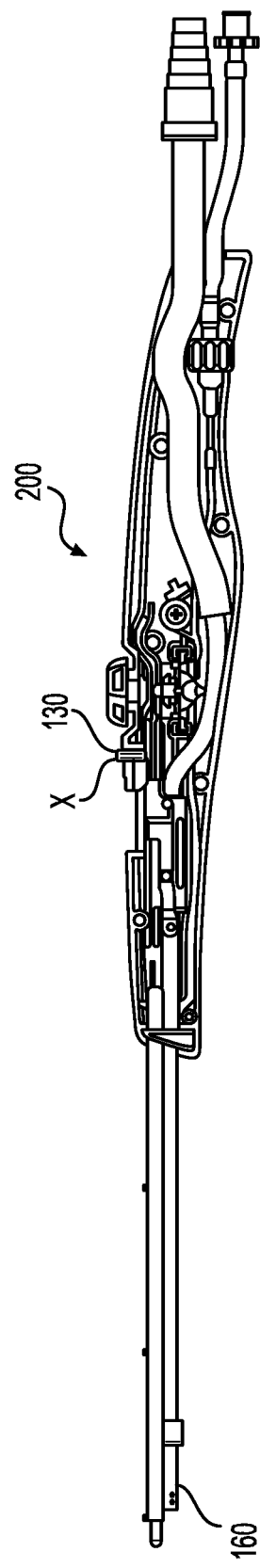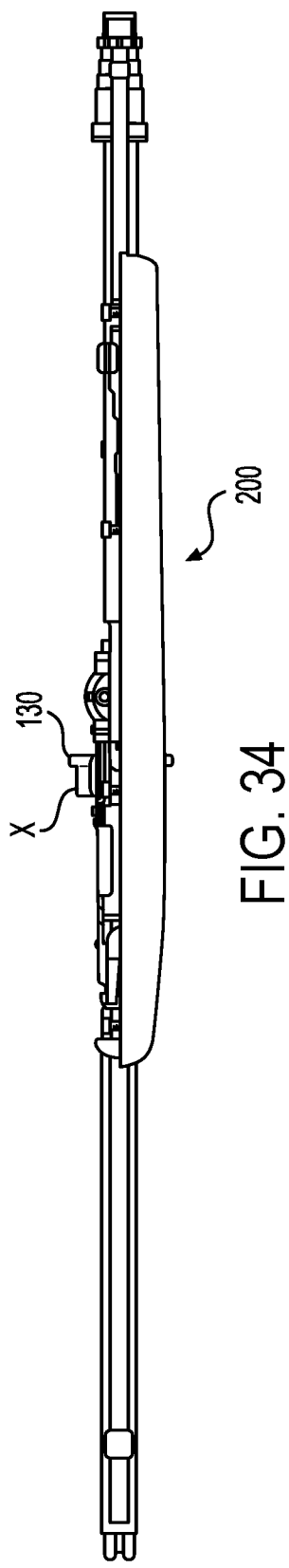

ELECTROSURGICAL INSTRUMENT WITH FLUID DIVERTER

CROSS-REFERENCE TO RELATED APPLICATION

This application is a continuation application claiming priority under 35 U.S.C. § 120 to U.S. patent application Ser. No. 15/274,559, entitled ELECTROSURGICAL INSTRUMENT WITH FLUID DIVERTER, filed Sep. 23, 2016, which issued on Aug. 25, 2020 as U.S. Pat. No. 10,751,117, the entire disclosure of which is hereby incorporated by reference herein.

BACKGROUND

Many internal surgical procedures require the removal of tissue as part of the surgical procedure. The removal of such tissue invariably results in severing multiple blood vessels leading to localized blood loss. Significant blood loss may comprise the patient's health by potentially leading to hypovolemic shock. Even minor blood loss may complicate the surgery by resulting in blood pooling into the surgical site, thereby obscuring the visibility of the tissue from the surgeons and surgical assistants. The problem of blood loss into the surgical site may be especially important in broad area surgeries, such as liver resection, in which multiple blood vessels may be severed during the procedure.

Typically, an electrosurgical cautery device is used to seal the blood vessels, thereby preventing blood loss. Such electrosurgical cautery devices may include bipolar devices that incorporate a pair of electrodes that are powered by RF (radiofrequency) energy to heat and cauterize the tissue and blood vessels. Direct application of the electrodes to the tissue may lead to unwanted effects such as localized tissue charring and fouling of the electrodes by charred tissue matter sticking to them.

A method to reduce charring and fouling may include introducing a saline fluid into the surgical site to irrigate the site. Alternatively, the saline fluid may be heated by the electrodes to form a steam to cauterize the tissue. In this manner, the tissue is not placed in direct contact with the electrodes and electrode fouling is prevented. Although a saline fluid may be used, any electrically conducting fluid (for example, an aqueous mixture containing ionic salts) may be used to promote steam-based cauterization. After the steam cauterizes the tissue by transferring its heat thereto, the steam may condense to water. The resulting water may be used to clear the surgical site of unwanted material such as the remnants of the cauterized tissue. An aspirator may be used to remove the mixture of water and tissue remnants. It may be difficult and inefficient for the surgeon to cauterize and aspirate the tissue especially if separate devices are required. Thus, a device incorporating the cauterization and aspiration functions is desirable.

The incorporation of both a saline source and an evacuation source for aspiration into a bipolar electrosurgical cautery instrument may be problematic. If the aspirator operates continuously, then the saline may not reside in contact with the electrodes long enough to be heated and form steam. If the saline source operates continuously, then excess saline may be delivered to the surgical site and obscure the area from the surgeon. It is possible to have a device with multiple actuators to allow the surgeon to selectively emit a fluid to be vaporized by the electrodes and evacuate the surgical site. However, such multiple actuators may be clumsy to use and lead to hand and finger fatigue during a long surgical procedure.

Therefore, it is desirable to have a device that permits a surgeon to effectively and efficiently provide steam cauterization and tissue mixture aspiration to a surgical site without requiring excessive manipulation of the surgical device.

SUMMARY

In one aspect, an electrosurgical device may include: a proximal fluid source port and a first fluid path in fluid communication with the proximal fluid source port; a proximal fluid evacuation port and a second fluid path in fluid communication with the proximal fluid evacuation port; a first electrode and a second electrode; a housing configured to enclose a first portion of the first fluid path, a first portion of the second fluid path, a first portion of the first electrode, and a first portion of the second electrode; a shaft extending distally from the housing configured to enclose a second portion of the first fluid path, a second portion of the second fluid path, a second portion of the first electrode, and a second portion of the second electrode and an end effector, the end effector comprising: a distal fluid discharge port in fluid communication with the second portion of the first fluid path; a distal fluid aspiration port in fluid communication with the second portion of the second fluid path; a third portion of the first electrode and a third portion of the second electrode; and a diverter comprising a first edge in mechanical communication with the third portion of the first electrode and a second edge in mechanical communication with the third portion of the second electrode, wherein the diverter is configured to receive, on a first surface, a fluid emitted by the distal fluid discharge port, and wherein the distal fluid aspiration port is configured to remove a material from an area proximal to the diverter.

In one aspect of the electrosurgical device, the diverter may be configured to maintain a contact between the fluid, a surface of the third portion of the first electrode, and a surface of the third portion of the second electrode.

In one aspect of the electrosurgical device, the diverter may comprise a plurality of features on the first surface.

In one aspect, the electrosurgical device may include a plurality of features that are configured to direct a fluid flow of the fluid on the first surface of the diverter.

In one aspect, the electrosurgical device may include a plurality of features that comprise a plurality of protrusions.

In one aspect, the electrosurgical device may include a plurality of features that comprise a plurality of recesses.

In one aspect of the electrosurgical device may include a distal fluid discharge port that comprises an aperture comprising a circular opening, a semi-lunar opening, or a slit opening.

In one aspect, the electrosurgical device may include a second portion of the first fluid path, proximal to the distal fluid discharge port, which is configured to impart a turbulent flow to a fluid flowing within the second portion of the first fluid path.

In one aspect, the electrosurgical device may include a second portion of the first fluid path that comprises a first cannula and a second cannula.

In one aspect, the electrosurgical device may include a first cannula that is in mechanical communication with an inner surface of the third portion of the first electrode and the second cannula that is in mechanical communication with an inner surface of the third portion of the second electrode.

In one aspect, the electrosurgical device may include a distal fluid discharge port that comprises a plurality of pores in the first cannula and the second cannula.

In one aspect, an end effector of an electrosurgical device, may include: a distal fluid discharge port in fluid communication with a first fluid path; a distal fluid aspiration port in fluid communication with a second fluid path; a first electrode and a second electrode; and a diverter in mechanical communication with the first electrode and the second electrode, and disposed therebetween, wherein the diverter is configured to receive, on a first surface, a fluid emitted by the distal fluid discharge port, and to maintain a contact of the fluid thereon with a surface of the first electrode and a surface of the second electrode, and wherein the diverter is configured to prevent an aspiration by the distal fluid aspiration port of the fluid on the first surface thereof.

In one aspect, the end effector may include a diverter that comprises an electrically insulating material.

In one aspect, the end effector may include a diverter that comprises a heat resistant material.

In one aspect, the end effector may include a diverter that comprises a plurality of features on the first surface.

In one aspect, the end effector may include a plurality of features that are configured to direct a flow of the fluid on the first surface of the diverter towards the first electrode or the second electrode.

In one aspect, the end effector may include a plurality of features that comprise a plurality of protrusions.

In one aspect, the end effector may include a plurality of features that comprise a plurality of recesses.

In one aspect, the end effector may include a first fluid path that comprises a first cannula and a second cannula.

In one aspect, the end effector may include a first cannula that is in mechanical communication with an inner surface of the first electrode and a second cannula that is in mechanical communication with an inner surface of the second electrode.

In one aspect, the end effector may include a distal fluid discharge port that comprises a plurality of pores in a first cannula and a second cannula and wherein the plurality of pores are configured to source the fluid onto the first surface of the diverter.

In one aspect, an end effector of an electrosurgical device may include: an outlet port in fluid communication with a first fluid path; an inlet port in fluid communication a second fluid path; a first electrode and a second electrode positioned in juxtaposed relationship; and a diverter comprising a first surface configured to receive fluid emitted by the outlet port, wherein the diverter is disposed between the first and second juxtaposed electrodes, and wherein the diverter is disposed between the outlet port and the inlet port to separate the outlet port and the inlet port.

BRIEF DESCRIPTION OF THE FIGURES

The features of the various aspects are set forth with particularity in the appended claims. The various aspects, however, both as to organization and methods of operation, together with advantages thereof, may best be understood by reference to the following description, taken in conjunction with the accompanying drawings as follows:

FIG. 1 illustrates a perspective view of one aspect of an electrosurgical device.

FIG. 2 illustrates an expanded view of one aspect of an end effector of the electrosurgical device depicted in FIG. 1.

FIGS. 4, 5, and 6 illustrate plan views of the bottom, side, and top, respectively, of one aspect of the electrosurgical device depicted in FIG. 1.

FIG. 17 illustrates an additional perspective view of one aspect of the interior components of the electrosurgical device depicted in FIG. 1.

FIG. 18 illustrates an expanded perspective view of one aspect of an end effector of the electrosurgical device depicted in FIG. 17.

FIG. 19 illustrates an expanded perspective view of one aspect of activation controls of the electrosurgical device depicted in FIG. 17.

FIG. 25 illustrates an additional perspective view of one aspect of the interior components of the electrosurgical device depicted in FIG. 9 illustrating a second position of one aspect of a slide switch.

FIG. 26 illustrates an expanded perspective view of one aspect of an end effector of the electrosurgical device depicted in FIG. 25 illustrating an extended position of one aspect of an aspiration tube.

FIGS. 32, 33, and 34 illustrate plan views of the top, side, and bottom, respectively, of one aspect of the electrosurgical device depicted in FIG. 9 illustrating a first position of one aspect of a slide switch.

DETAILED DESCRIPTION

Figure 3:
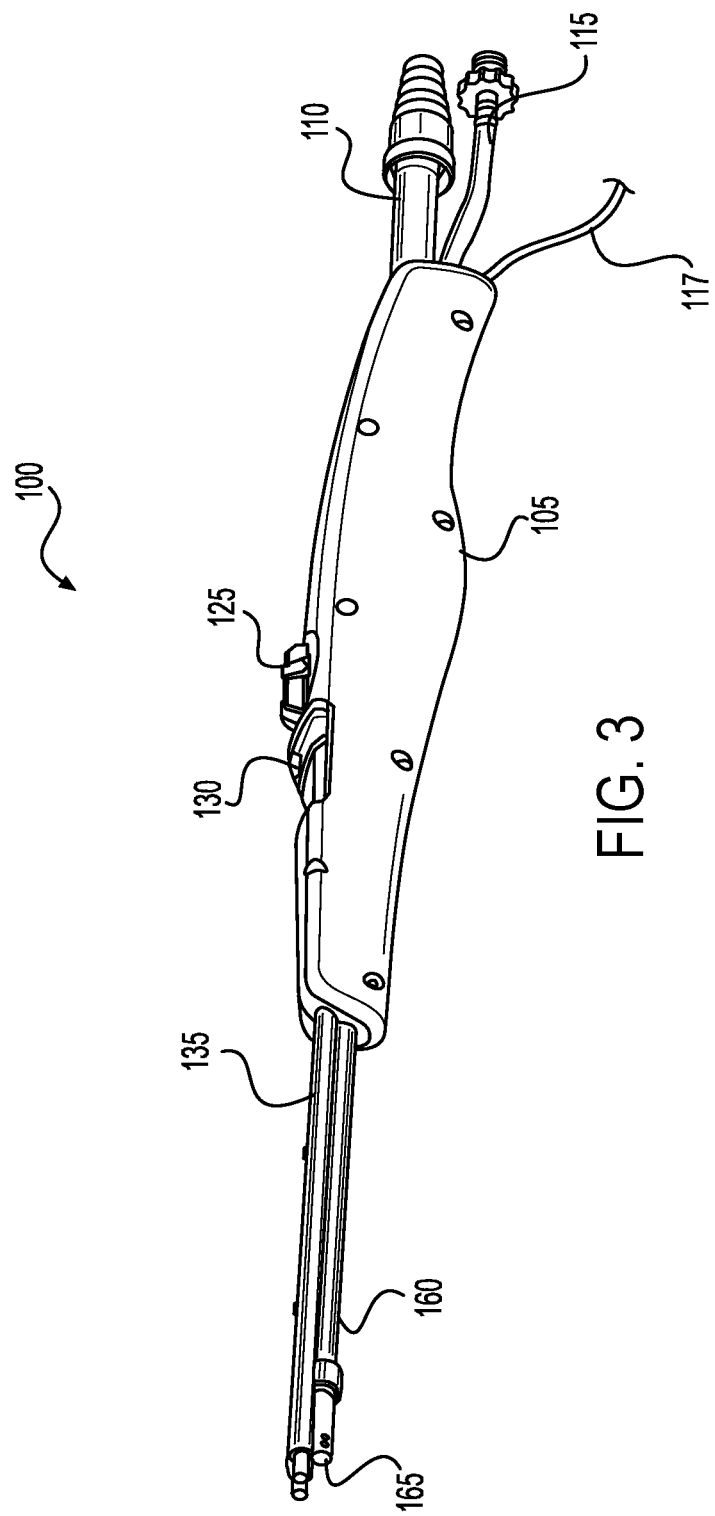
FIG. 3 illustrates a side perspective view of one aspect of the electrosurgical device depicted in FIG. 1.
Figure 8:
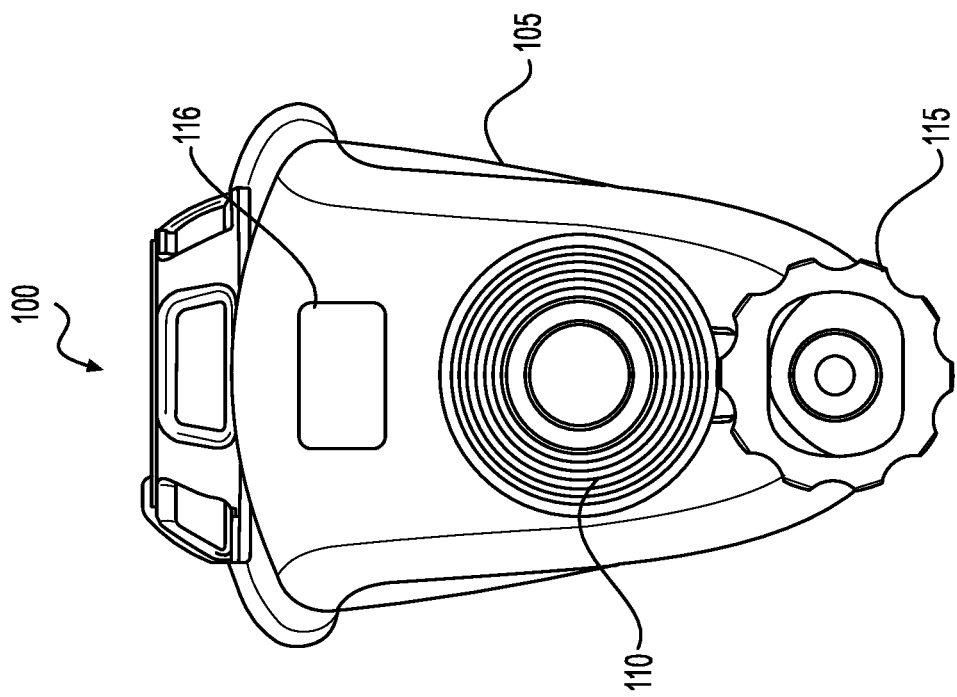
FIG. 8 illustrates a plan rear (proximal) view of one aspect of the electrosurgical device depicted in FIG. 1.
Figure 7:
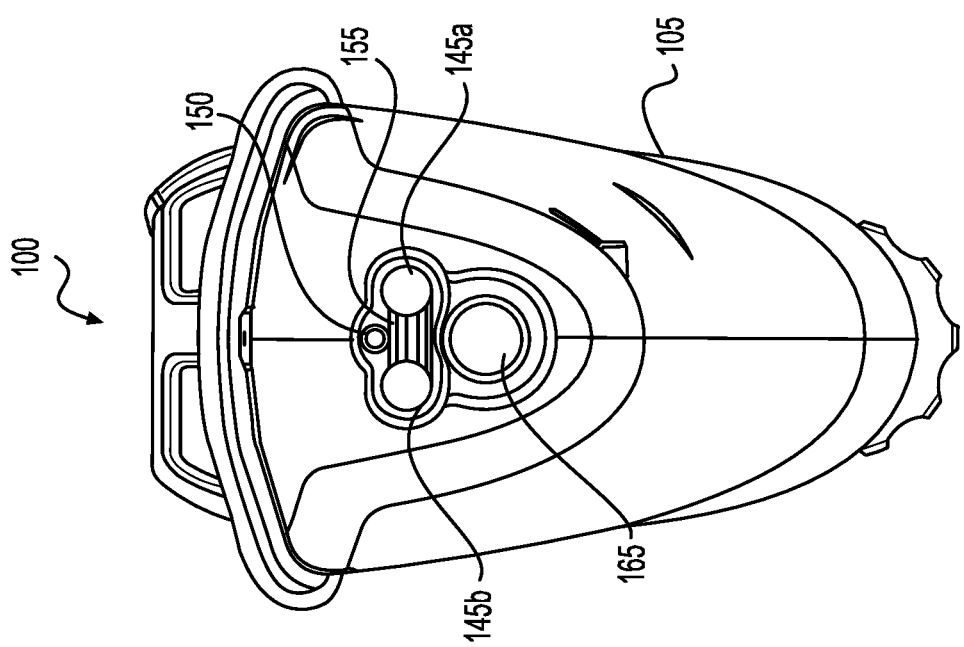
FIG. 7 illustrates a plan front (distal) view of one aspect of the electrosurgical device depicted in FIG. 1.

As disclosed above, an electrosurgical device may incorporate functions to cauterize and aspirate tissues during a broad area surgical procedure. In some electrosurgical devices, energized electrodes may be used to perform the cauterization procedure. However, as also disclosed above, the electrodes of such devices may be susceptible to fouling by the tissue contacted by the electrodes during cauterization. It may be appreciated that cauterization of tissue may be accomplished by exposing the tissue to a heated material other than the electrodes. As also disclosed above, in one non-limiting example, a fluid, such as a saline fluid, may be heated by the electrodes and the heated fluid or steam may then be used to cauterize the tissue. The saline, or other conductive fluid, may be heated by an electrical current flowing between the electrodes. In this manner, the temperature used to cauterize the tissue may be limited by the temperature of the steam (for example, at around 100° C.) thereby reducing the potential of tissue charring. Further, the surrounding tissue may be moistened by the steam, thereby preventing desiccation due to their proximity to a heated device. Additionally, the steam, upon losing heat by contacting the tissue, may condense to water, and the water may then be used to irrigate the surgical site. In this manner, a saline fluid may be used for the dual purposes of cauterization and irrigation, thereby increasing the efficiency of the cauterization procedure.

FIGS. 1-8 depict views of one example of such an electrosurgical device 100. For FIGS. 1-8, common reference numbers refer to common components within the figures.

The electrosurgical device 100 may include a housing 105 with a shaft 135 extending distally from the housing 105. The housing 105 may include, on a proximal end, a proximal fluid source port 115 and a proximal fluid evacuation port 110. In some electrosurgical device systems, the proximal fluid source port 115 may be placed in fluid communication with a source of a fluid, for example saline, buffered saline, Ringer's solution, or other electrically conducting fluids such as aqueous fluids containing ionic salts. The fluid source may operate as a gravity feed source or it may include components to actively pump the fluid into the proximal fluid source port 115. An actively pumping fluid source may include, without limitation, a power supply, a pump, a fluid source, and control electronics to allow a user to actively control the pumping operation of the actively pumping fluid source. In some electrosurgical device systems, the fluid evacuation port 110 may be placed in fluid communication with a vacuum source. The vacuum source may include a power supply, a pump, a storage component to store material removed by the vacuum source, and control electronics to allow a user to actively control the pumping operation of the vacuum source.

In addition, the housing 105 may include a connector 116 to which a cable 117 of an energy source 120 may be attached. The energy source 120 may be configured to supply energy (for example RF or radiofrequency energy) to the electrodes 145*a,b*. The energy source 120 may include a generator configured to supply power to the electrosurgical device 100 through external means, such as through the cable 117. In certain instances, the energy source 120 may include a microcontroller coupled to an external wired generator. The external generator may be powered by AC mains. The electrical and electronic circuit elements associated with the energy source 120 may be supported by a control circuit board assembly, for example. The microcontroller may generally comprise a memory and a microprocessor ("processor") operationally coupled to the memory. The electronic portion of the energy source 120 may be configured to control transmission of energy to electrodes 145*a,b* at the end effector 140 of the electrosurgical device 100. It should be understood that the term processor as used herein includes any suitable microprocessor, microcontroller, or other basic computing device that incorporates the functions of a computer's central processing unit (CPU) on an integrated circuit or at most a few integrated circuits. The processor may be a multipurpose, programmable device that accepts digital data as input, processes it according to instructions stored in its memory, and provides results as output. It is an example of sequential digital logic, as it has internal memory. Processors operate on numbers and symbols represented in the binary numeral system. The energy source 120 may also include input devices to allow a user to program the operation of the energy source 120.

The housing 105 may also include one or more activation devices to permit a user to control the functions of the electrosurgical device 100. In some non-limiting example, the electrosurgical device 100 may include a metering valve 125 that may be activated by a user to control an amount of fluid flowing through the electrosurgical device and provide, at the distal end, an amount of the fluid to the end effector 140. In some non-limiting examples, the metering valve 125 may also permit the user to control an amount of energy supplied by the energy source 120 to the electrodes 145a,b at the end effector 140. As an example, the metering valve 125 may comprise a screw activation pinch valve to regulate the flow of fluid through the electrosurgical device 100. Additionally, the metering valve 125 may have a push-button activation function to permit current to flow from the energy source 120 to the electrodes 145a,b upon depression of the push-button by a user. It may be recognized that in some non-limiting examples, the housing 105 may include a metering valve 125 to allow regulation of fluid flow through the electrosurgical device 100 and a separate energy control device to control the amount of current sourced to the electrodes 145a,b.

The housing 105 may also be attached to a shaft 135 at a distal end of the housing 105. An end effector 140 may be associated with a distal end of the shaft 135. The end effector 140 may include electrodes 145a,b that may be in electrical communication with the energy source 120 and may receive electrical power therefrom. In some non-limiting examples, a first electrode 145a may receive electrical energy of a first polarity (such as a positive polarity) from the energy supply 120 and the second electrode 145b may receive electrical energy of a second and opposing polarity (such as a negative polarity) from the energy supply 120. Alternatively, the first electrode 145a may be connected to a ground terminal of the energy supply 120, and the second electrode 145b may be connected to a varying AC voltage terminal of the energy supply 120. The electrodes 145a,b may extend beyond the distal end of the shaft 135. The extended ends of the electrodes 145a,b be separated by a diverter 155. The diverter 155 may contact the first electrode 145a at a first edge of the diverter 155, and the diverter 155 may contact the second electrode 145b at a second edge of the diverter 155. The diverter 155 may comprise an electrically insulating material and/or a heat resistant material, which may include, without limitation a plastic such as a polycarbonate or a ceramic. The diverter 155 may be deformable or non-deformable. In some non-limiting examples, the housing 105 may include a mechanism to control a shape of a deformable diverter 155.

Figure 11:
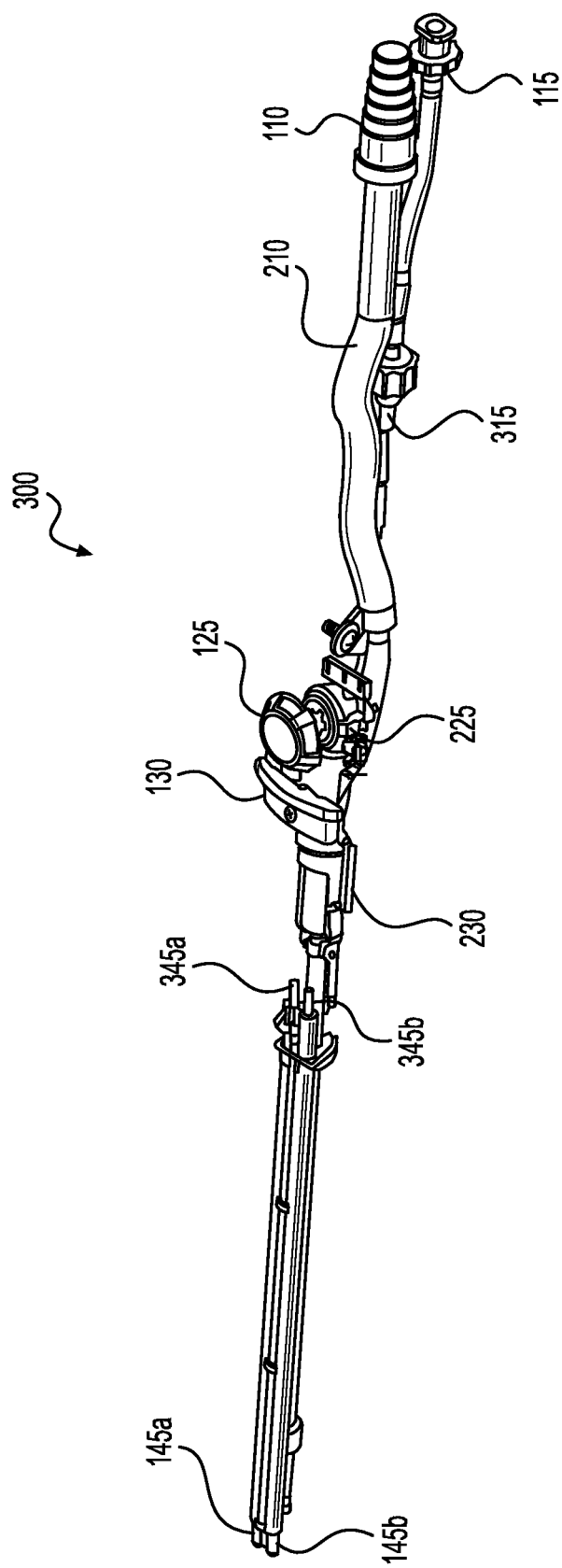
FIG. 11 illustrates a perspective view of one aspect of the interior components of the electrosurgical device depicted in FIG. 1.
Figure 12:
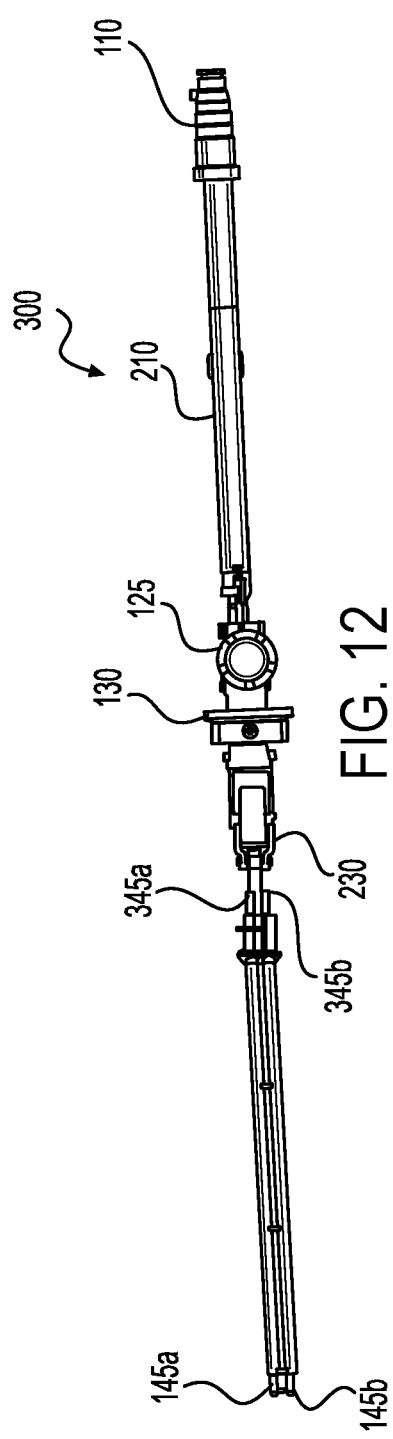
FIGS. 12, 13, and 14 illustrate plan views of the top, side, and bottom, respectively, of one aspect of the interior components of the electrosurgical device depicted in FIG. 11.
Figure 13:
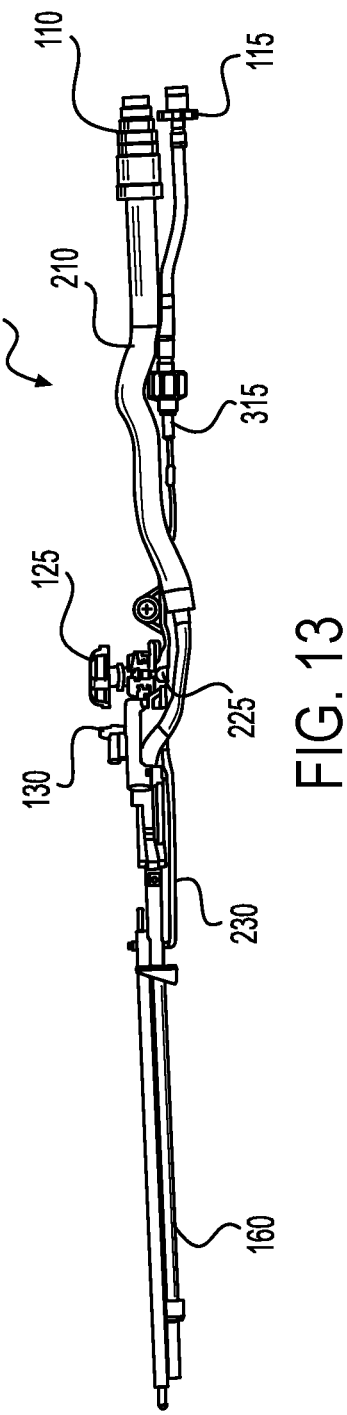
Figure 14:
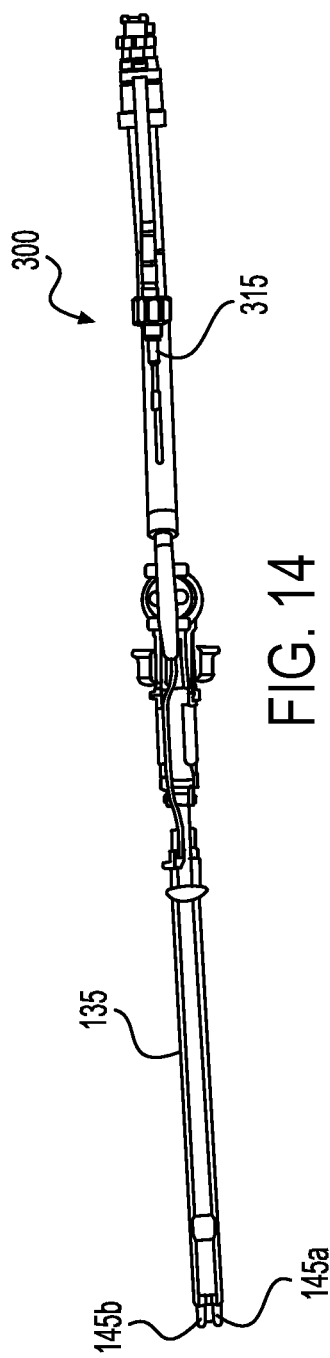
Figure 16:
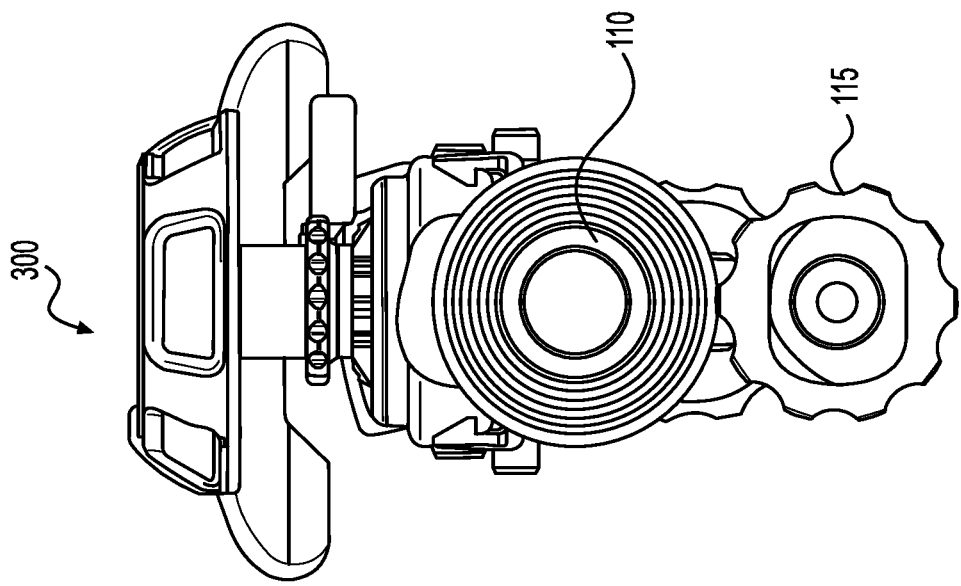
FIG. 16 illustrates a plan rear (proximal) view of one aspect of the interior components of the electrosurgical device depicted in FIG. 11.
Figure 15:
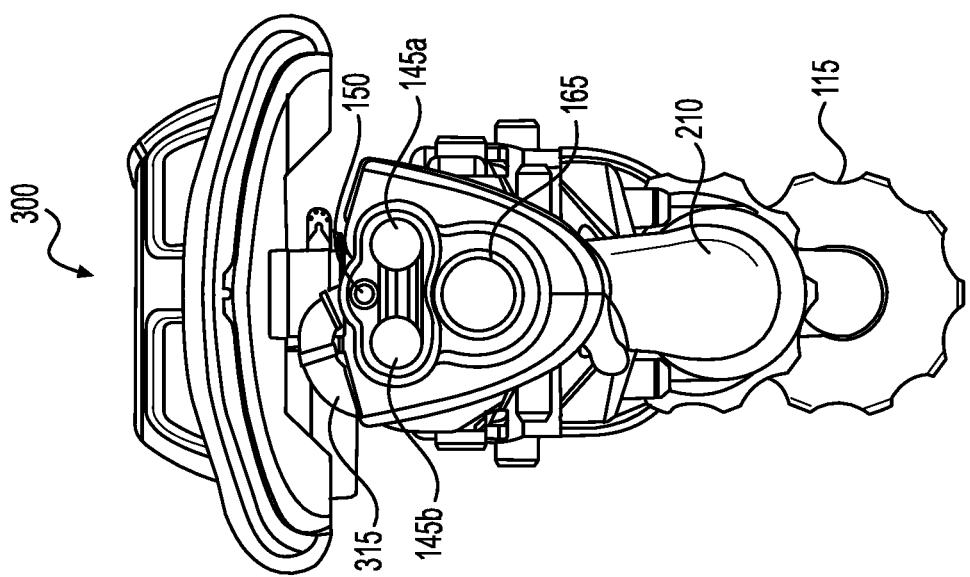
FIG. 15 illustrates a plan front (distal) view of one aspect of the interior components of the electrosurgical device depicted in FIG. 11.
Figure 20:
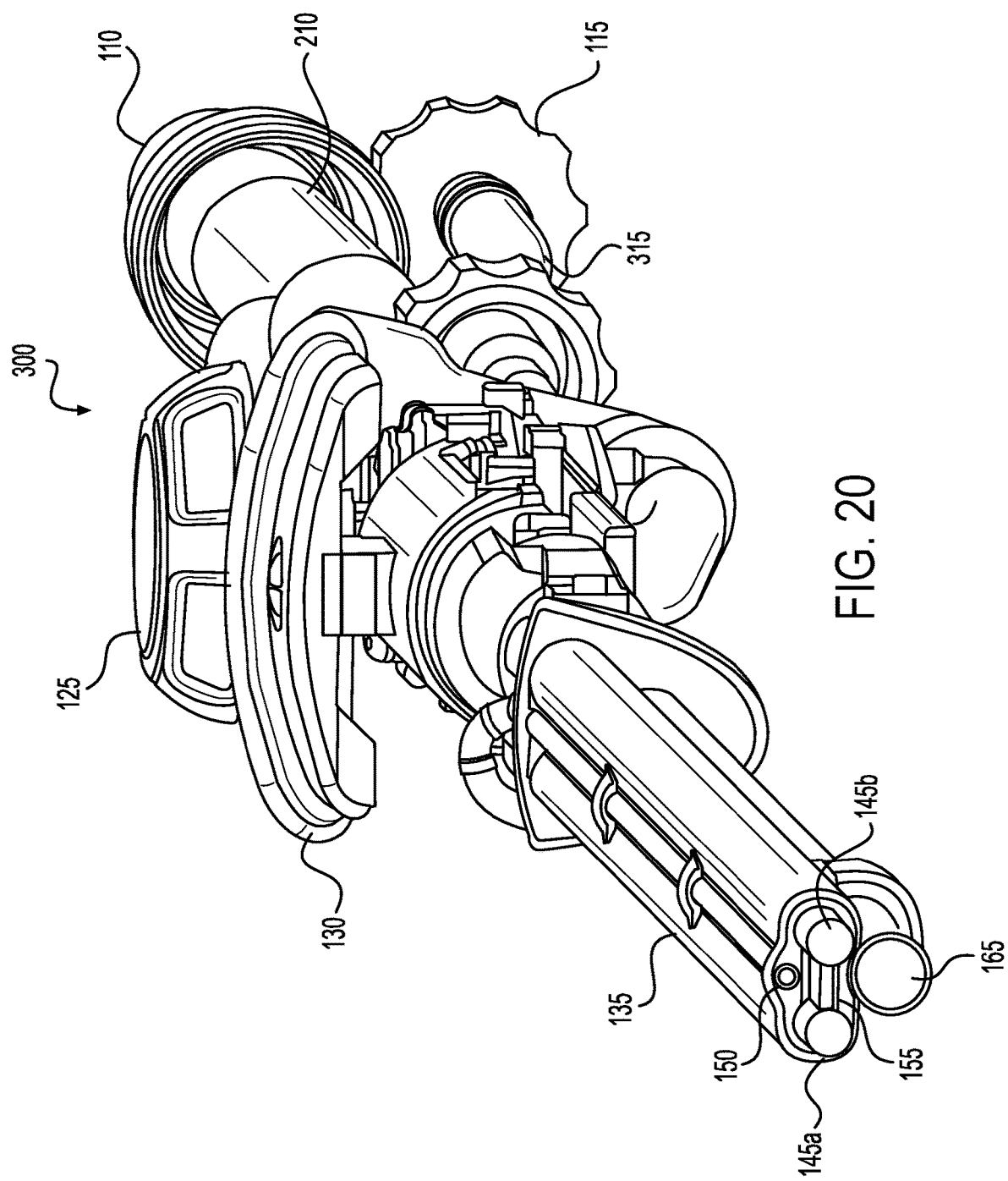
FIG. 20 illustrates a front (distal) perspective view of one aspect of the electrosurgical device depicted in FIG. 17.
Figure 21:
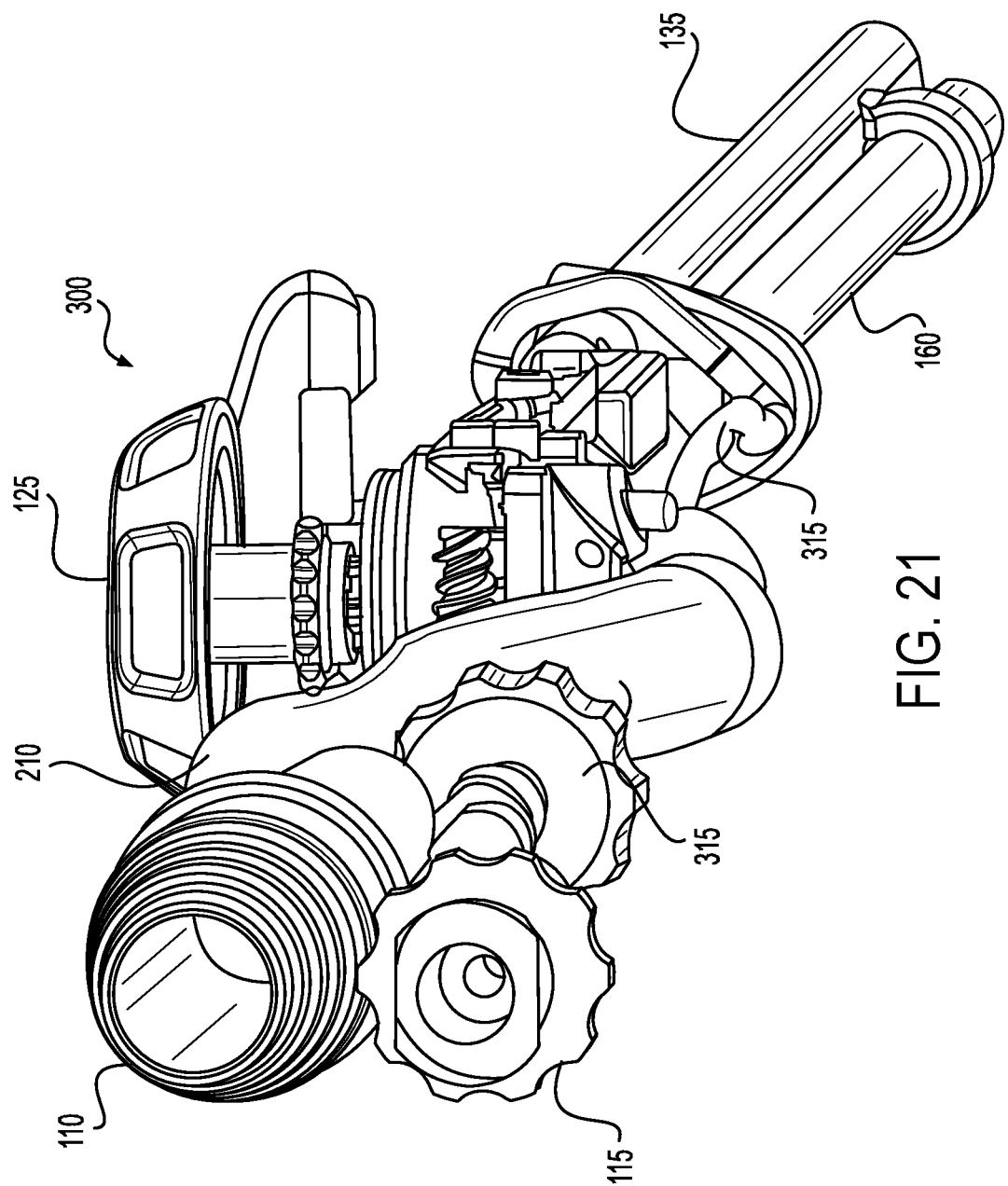
FIG. 21 illustrates a rear (proximal) perspective view of one aspect of the electrosurgical device depicted in FIG. 17.

The end effector 140 may also include a fluid discharge port 150 that may be in fluid communication with the fluid source port 115 through a first fluid path. The first fluid path, such as a source fluid path (see 315 in FIG. 11), may permit the fluid to flow from the fluid source port 115 to the fluid discharge port 150. In some non-limiting examples, the fluid discharge port 150 may be positioned above the diverter 155 so that a fluid emitted by the fluid discharge port 150 may be collected on a top surface of the diverter 155. The end effector may also include a fluid aspiration port 165 that may be in fluid communication with the fluid evacuation port 110 through a second fluid path. The second fluid path, such as an aspirated fluid path (see 210 in FIG. 9), may permit a liquid mixture generated at the surgical site to flow from the fluid aspiration port 165 to the fluid evacuation port 110. The liquid mixture may then be removed from the electrosurgical device 100 by the vacuum source and stored in the storage component for later removal.

In some non-limiting examples, the fluid aspiration port 165 may be formed at the distal end of an aspiration tube 160. The aspiration tube 160 may also form part of the aspirated fluid path 210. The aspiration tube 160 may be located within the shaft 135 or it may be located outside of and beneath the shaft 135. An aspiration tube 160 located outside of the shaft 135 may be in physical communication with an external surface of the shaft 135. In some examples, the aspiration tube 160 may have a fixed location with respect to the shaft 135. In some alternative examples, the aspiration tube 160 may be extendable in a distal direction with respect to the shaft 135. Extension of the extendable aspiration tube 160 may be controlled by means of an aspiration tube control device. As one non-limiting example, the aspiration tube control device may comprise a slide switch 130. The slide switch 130, in a first position (for example, in a proximal position), may cause the aspiration tube 160 to remain in a first or retracted position in which the aspiration port 165 is located essentially below the fluid discharge port 150. However, the slide switch 130 in a second position (for example in a distal position), may cause the aspiration tube 160 to extend in a distal direction to a fully extended position so that the aspiration port 165 is located distal from and beneath the fluid discharge port 150. In one example, the slide switch 130 may preferentially position the aspiration tube 160 in one of two positions, such as the retracted position and the fully extended position. It may be recognized, however, that the slide switch 130 may also permit the aspiration tube 160 to assume any position between the retracted position and the fully extended position. Regardless of the position of the aspiration tube 160 as disclosed above, the aspiration port 165 may be maintained at a location beneath a plane defined by the top surface of the diverter 155. In this manner, the diverter 155 is configured to prevent fluid emitted by the fluid discharge port 150 from directly being removed at the aspiration port 165.

Figure 9:
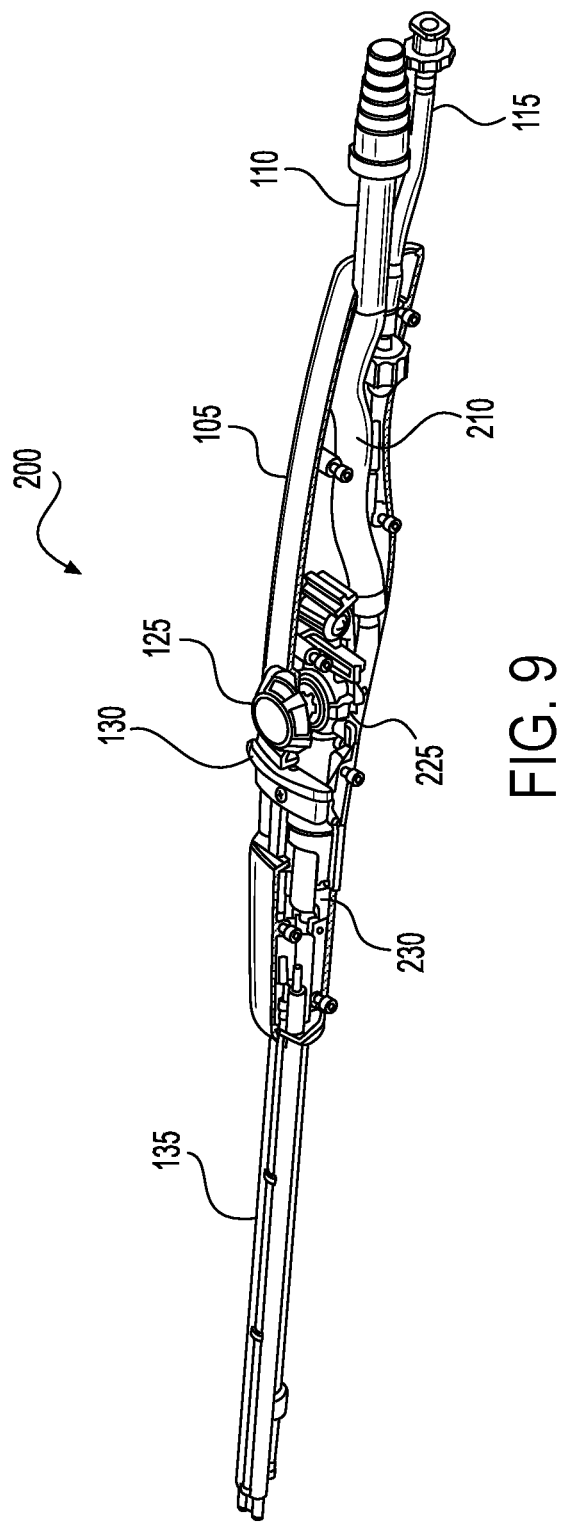
FIG. 9 illustrates a partial sectional perspective view of one aspect of the electrosurgical device depicted in FIG. 1.
Figure 10:
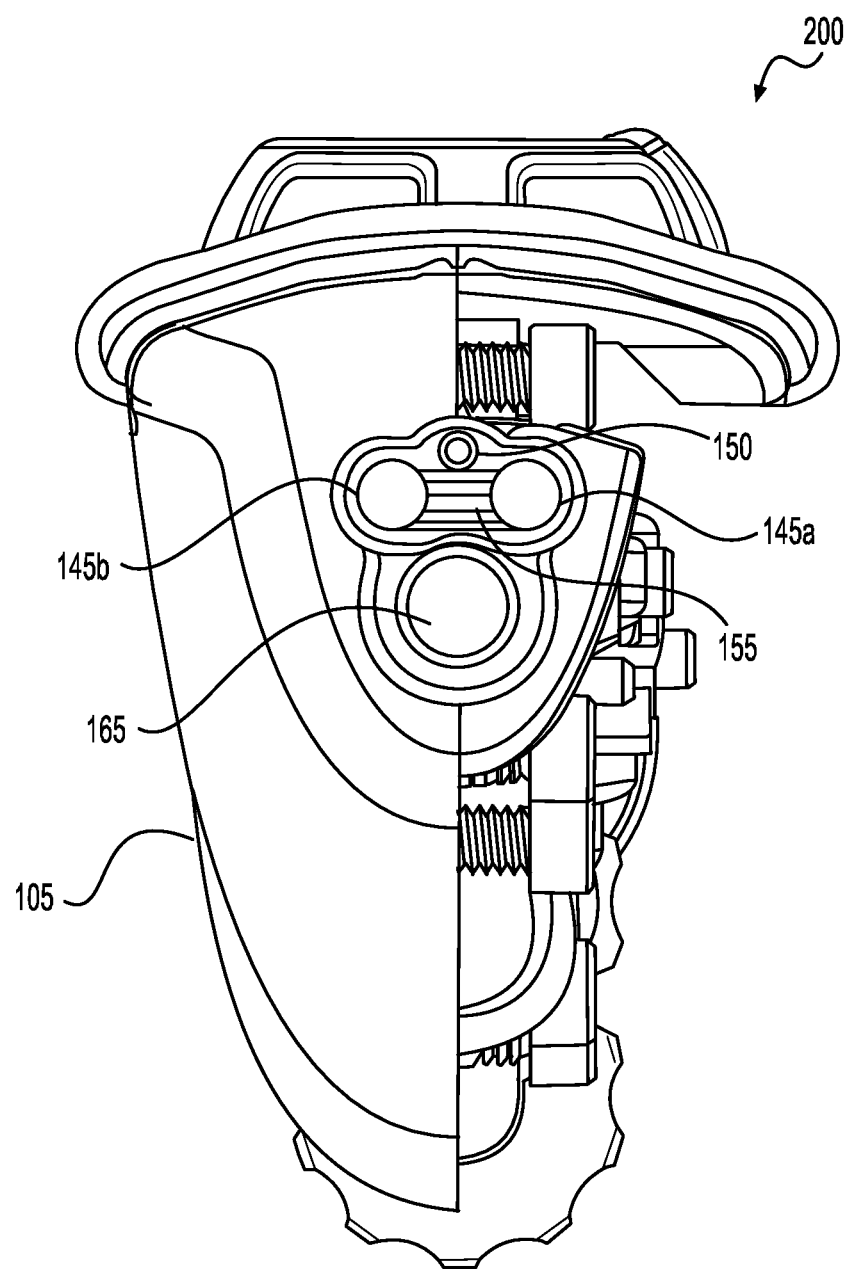
FIG. 10 illustrates a partial sectional plan front (distal) view of one aspect of the electrosurgical device depicted in FIG. 1.

FIGS. 9 and 10 present partial interior views of an electrosurgical device 200. In addition to the components disclosed above with respect to FIGS. 1-8, the electrosurgical device 200 includes an aspirated fluid path 210 that forms a fluid connection between the proximal fluid evacuation port 110 and the distal fluid aspiration port 165. Also illustrated are valve components 225 of the metering valve 125 and control components 230 of the aspiration tube such as, for example, a slide switch 130. Fluid discharge port 150, electrodes 145a,b, fluid aspiration port 165, and a portion of housing 105 are also illustrated in FIGS. 9 and 10.

FIGS. 11-21 present a variety of views of the interior components of electrosurgical device 300. FIG. 18 is a close-up view of the distal end of the electrosurgical device 300 shown in FIG. 17, and FIG. 19 is a close-up view of actuator components of the electrosurgical device 300 shown in FIG. 17 depicting the metering valve 125 and slide switch 130. Additional components depicted in FIGS. 11-21 include the source fluid path 315 that forms a fluid connection between the proximal fluid source port 115 and the distal fluid discharge port 150. In some examples, the valve components 225 of the metering valve 125 are disposed along the length of the source fluid path 315 permitting a user of electrosurgical device 300 to regulate a flow of fluid through the source fluid path 315 from the fluid source port 115 to the fluid discharge port 150. In some examples of the valve components 225, a screw actuator, such as a pinch valve, may be used to compress a portion of the source fluid path 315, thereby restricting a flow of fluid therethrough. It may be recognized that any number of fluid control valves may be used as valve components 225 including, without limitation, a ball valve, a butterfly valve, a choke valve, a needle valve, and a gate valve. It may be understood from FIGS. 11-21 that source fluid path 315 extends from fluid source port 115 through the housing 105 and through shaft 135 to the distal fluid discharge port 150. Similarly, it may be understood from FIGS. 11-22 that aspirated fluid path 210 extends form the proximal fluid evacuation port 110 through the housing 105 and through shaft 135 to the distal fluid aspiration port 165. Additionally, electrodes 145a,b may extend from housing 105 through shaft 135 and extend distally and protrude from the end of shaft 135. Alternatively, electrodes 145a,b may extend only through the shaft 135 and extend distally and protrude from the end of shaft 135. Proximal ends 345a,b of the electrodes 145a,b, may receive connectors to place the electrodes 145a,b in electrical communication with energy source 120. Electrodes 145a,b may receive the electrical energy from the energy source 120 to permit cauterization to the tissue in the surgical site either through direct contact of the tissue with the protruding portion of the electrodes 145a,b, or through heating a fluid contacting electrodes 145a,b.

Figure 22:
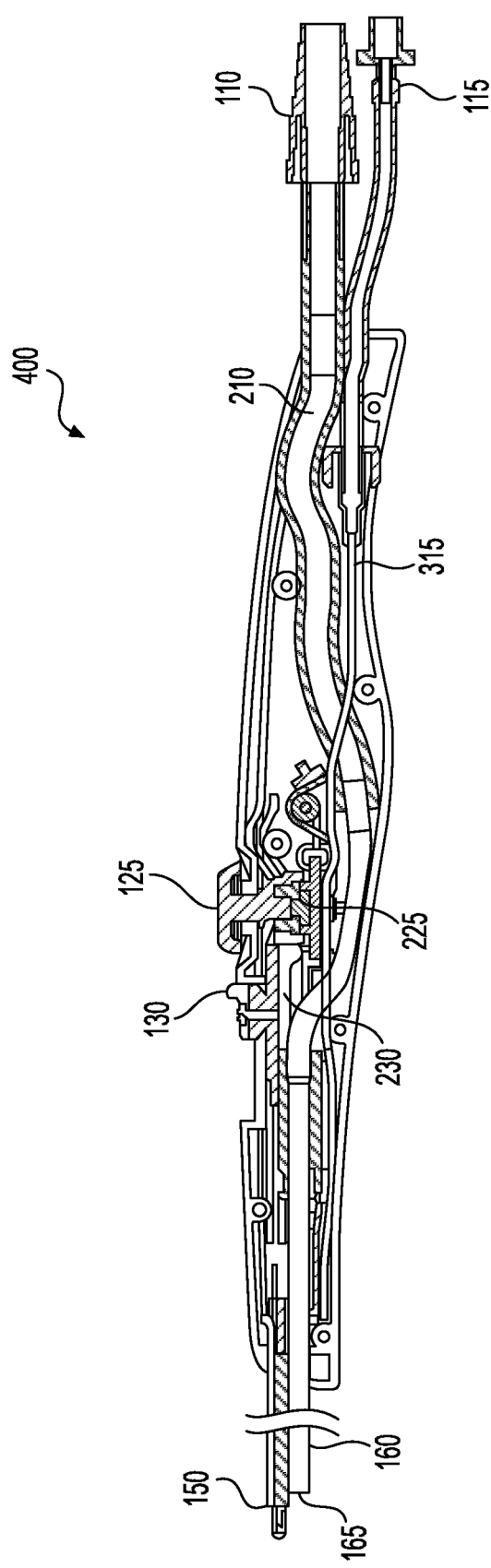
FIG. 22 illustrates a cross-sectional view of one aspect of the electrosurgical device depicted in FIG. 9.

FIG. 22 is a cross-sectional view of electrosurgical device 400. In particular, the cross-sectional view 400 illustrates the two fluid paths through the device. Thus, FIG. 22 illustrates source fluid path 315 in fluid communication with the proximal fluid source port 115 and the distal fluid discharge port 150. Additionally, FIG. 22 illustrates an example of a physical relationship between source fluid path 315 and the valve components 225 of the metering valve 125. FIG. 22 also illustrates an example in which the source fluid path 315 may extend through both the housing 105 and the shaft 135. Further, FIG. 22 illustrates aspirated fluid path 210 in fluid communication with the proximal fluid evacuation port 110 and the distal fluid aspiration port 165. The aspirated fluid path 210 may also include an aspiration tube 160 that may be disposed at a distal end of the aspirated fluid path 210. The distal fluid aspiration port 165 may be formed at a distal end of the aspiration tube 160.

Figure 23:
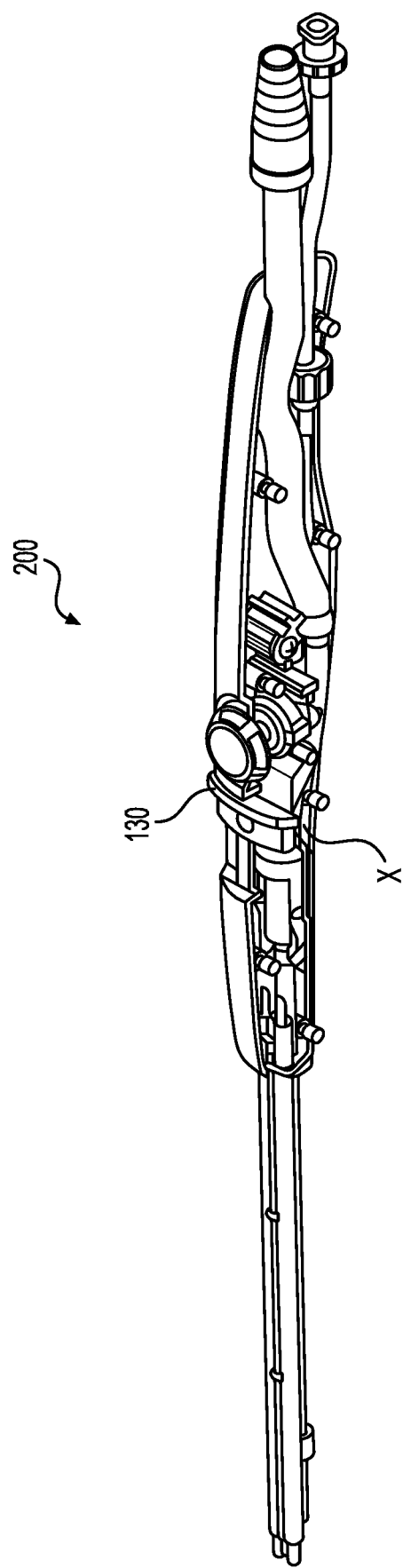
FIG. 23 illustrates partial sectional perspective view of one aspect of the electrosurgical device depicted in FIG. 9 illustrating a first position of one aspect of a slide switch.
Figure 24:
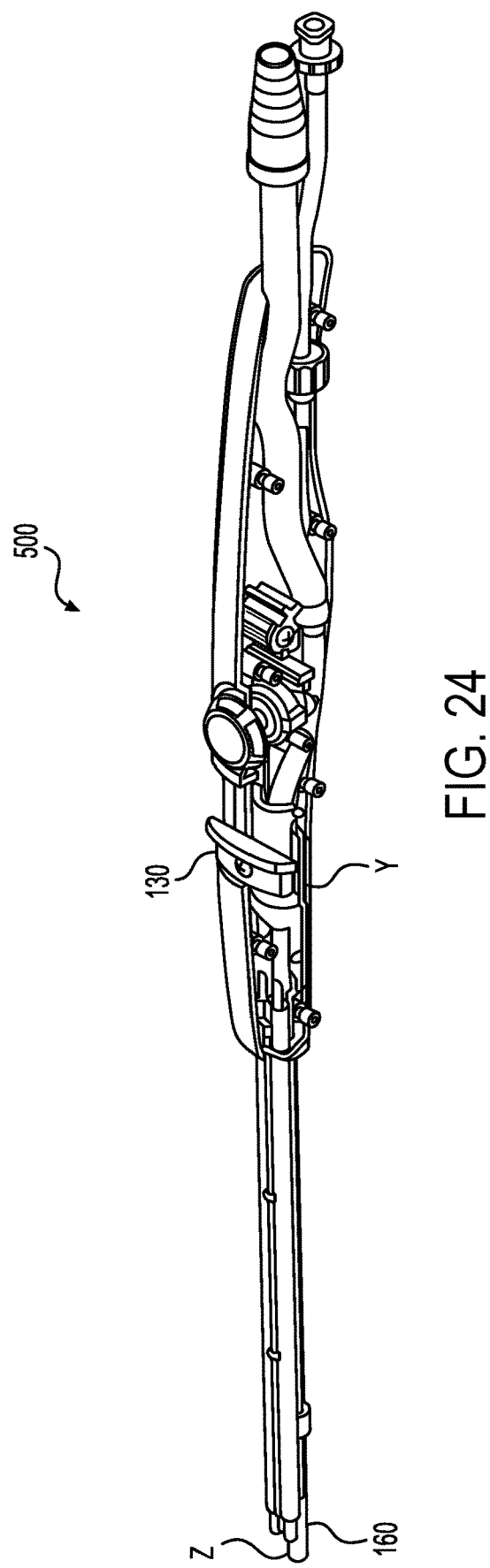
FIG. 24 illustrates partial sectional perspective view of one aspect of the electrosurgical device depicted in FIG. 9 illustrating a second position of one aspect of a slide switch.
Figure 27:
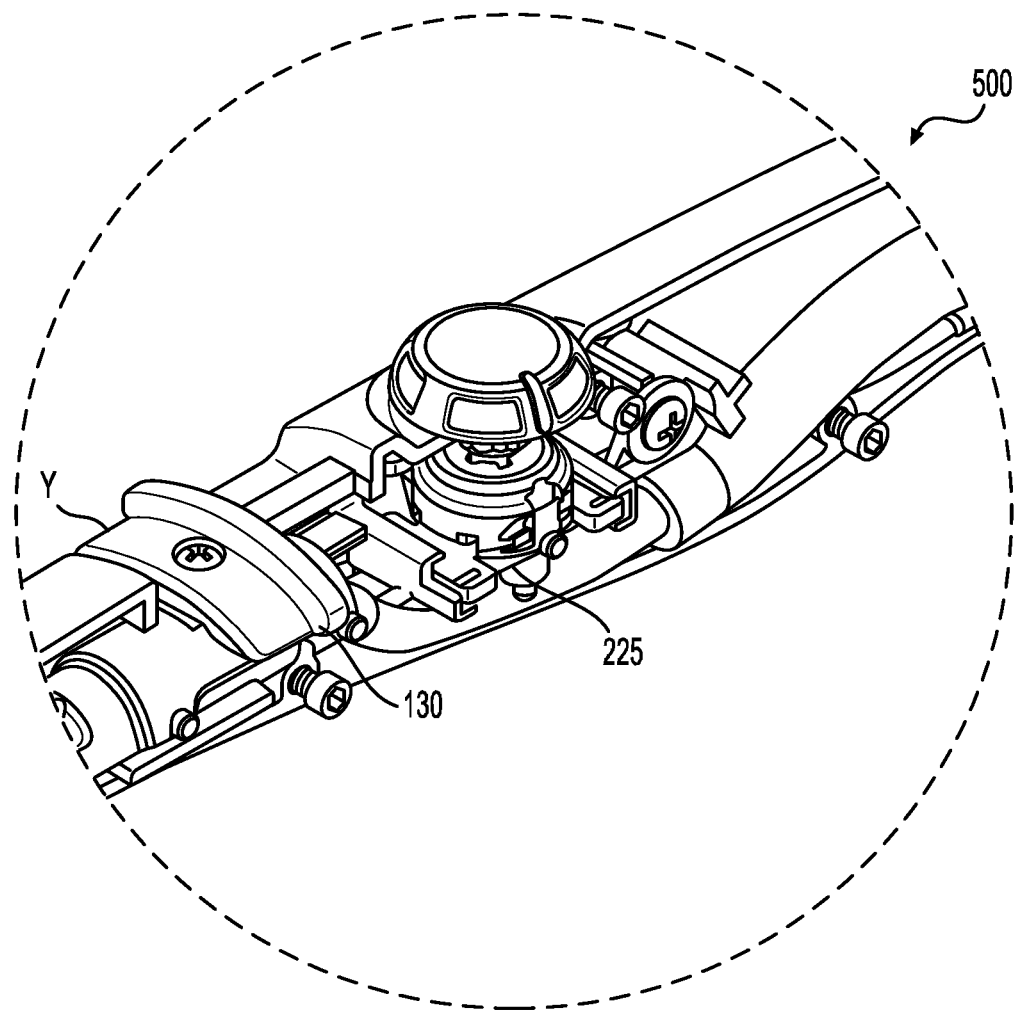
FIG. 27 illustrates an expanded perspective view of one aspect of activation controls of the electrosurgical device depicted in FIG. 25 illustrating a second position of one aspect of a slide switch.
Figure 29:
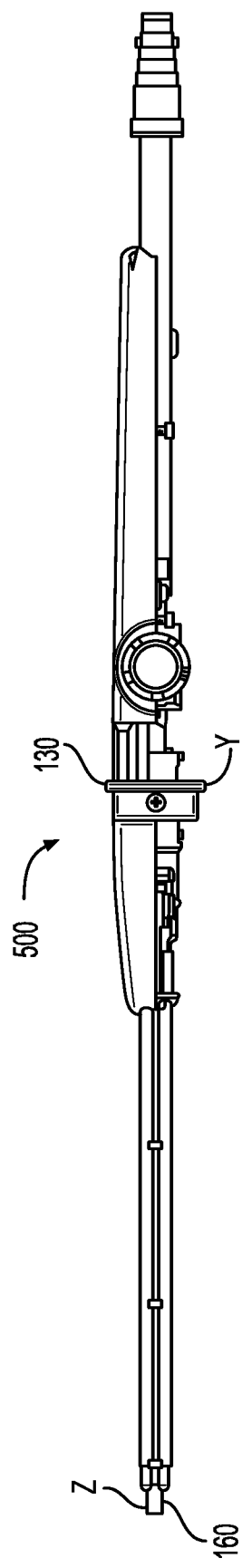
FIGS. 29, 30, and 31 illustrate plan views of the top, side, and bottom, respectively, of one aspect of the electrosurgical device depicted in FIG. 25 illustrating a second position of one aspect of a slide switch.
Figure 30:
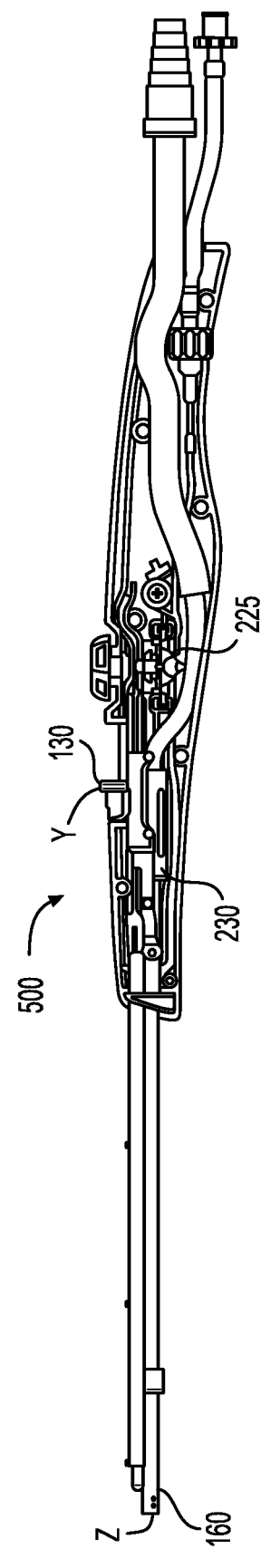
Figure 31:
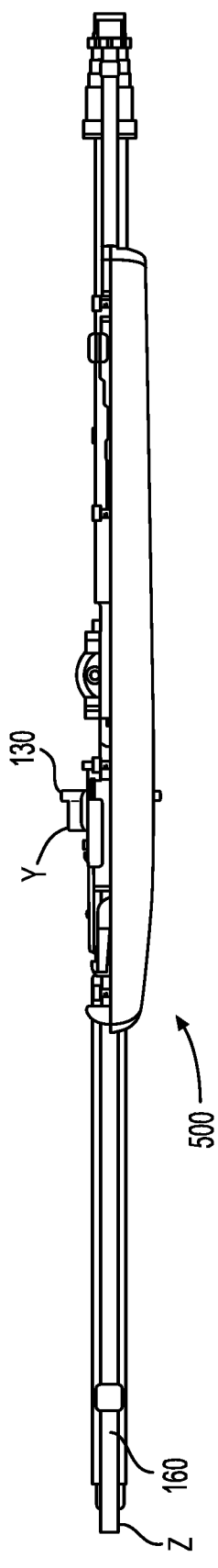

FIGS. 23-27 and 29-34 illustrate partial interior views of an electrosurgical device 200 having an aspiration tube 160 in a proximal or retracted position and an electrosurgical device 500 having an aspiration tube 160 in an distal or extended position Z. FIG. 23 is similar to FIG. 9 and particularly illustrates a first and proximal position X of the slide switch 130 (as a non-limiting example of an aspiration tube control device) along with a proximal or retracted position of aspiration tube 160. FIG. 24 particularly illustrates a second and distal position Y of the slide switch 130 (as a non-limiting example of an aspiration tube control device) in addition to a distal or extended position Z of aspiration tube 160. FIG. 25 illustrates an alternative perspective view of electrosurgical device 500. FIG. 26 is an expanded perspective view of the distal end of the electrosurgical device 500 shown in FIG. 25, particularly illustrating the distal end of aspiration tube 160 in the extended position Z. FIG. 27 is an expanded perspective view of actuator components of the electrosurgical device 500 shown in FIG. 25, particularly illustrating the second or distal position X of the slide switch 130. FIGS. 29, 30, and 31 present plan views of the top, side, and bottom, respectively, of electrosurgical device 500. FIGS. 29-31 may be compared with FIGS. 32, 33, and 34 which present plan views of the top, side, and bottom, respectively, of electrosurgical device 200. FIGS. 29-31 illustrate the distal positions Y and Z of slide switch 130 and aspiration tube 160, respectively. FIGS. 32-34 illustrate the proximal position X of slide switch 130 and the proximal or retracted position of aspiration tube 160.

Figure 28:
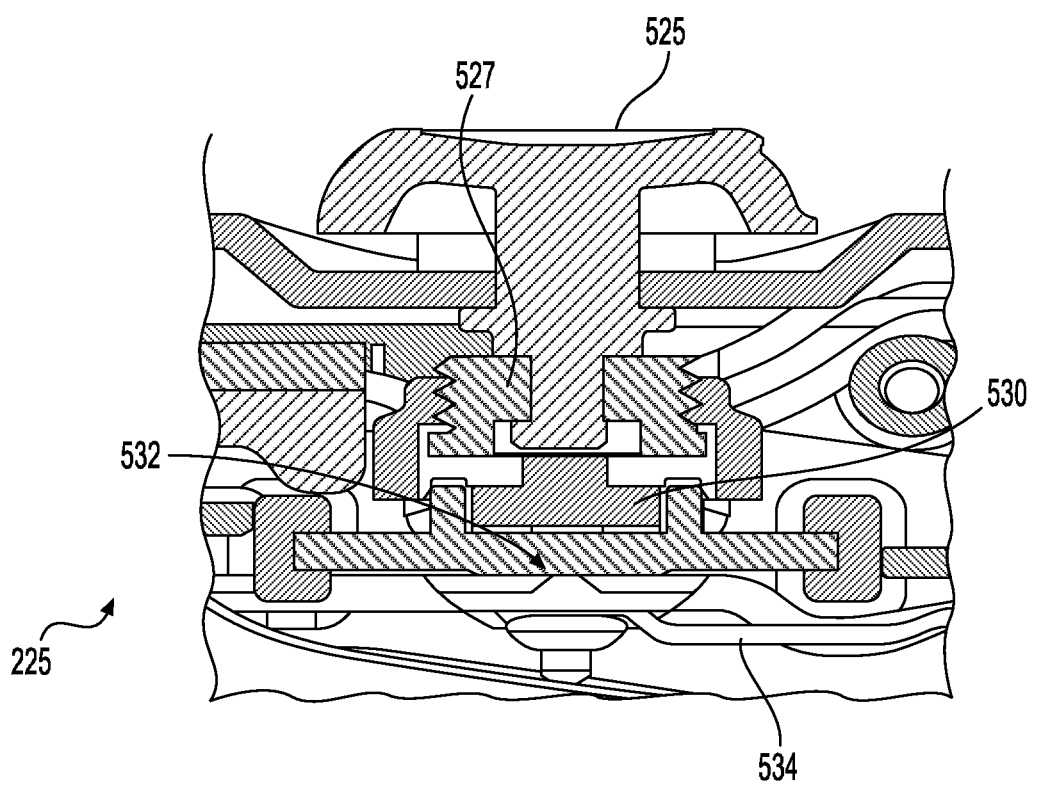
FIG. 28 illustrates an expanded cross-sectional view of one aspect of a metering valve of the electrosurgical device depicted in FIG. 1.

FIG. 28 illustrates a cross sectional view of an example of a metering valve 125 depicting some exemplary metering valve components 225. The valve components 225 may include a switch button 525 that may be activated by a user. The valve components 225 may also include an adjustable stop mechanism 527 that may adjust the position of a pinch valve 532 with respect to a portion of the source fluid path 315. The adjustable stop mechanism 527 may comprise a screw activated portion that may be adjusted by a rotation of the switch button 525. In this manner, a user may rotate the switch button 525 and adjust an amount of fluid flowing through the source fluid path 315 to exit from the distal fluid discharge port 150 based on an amount of compression applied to source fluid path 315 by a pinch valve. In some examples, the adjustable stop mechanism 527 may have two positions (an "open" position and a "closed" position). Alternatively, the adjustable stop mechanism 527 may be adjustable and permit the user to select any amount of fluid flow through the source fluid path 315.

Additionally, the metering valve 125 may include additional components 225 that may be used to control an electrical connection between the electrodes 145a,b and the energy source 120. For example, an RF switch 530 may used to form the electrical connections between the electrodes 145a,b and the energy source 120. In one example, the RF switch 530 may be a momentary contact switch that connects the electrodes 145a,b and the energy source 120 only when actively depressed by a user. Alternatively, the RF switch 530 may be a latching push button switch that may be sequentially activated (push-to-make) and deactivated (push-to-break) upon being depressed. A closure spring 534 may be included among the switch components 225 to return the switch button 525 to an undepressed state when a user is not actively depressing the switch button 525.

Figure 35:
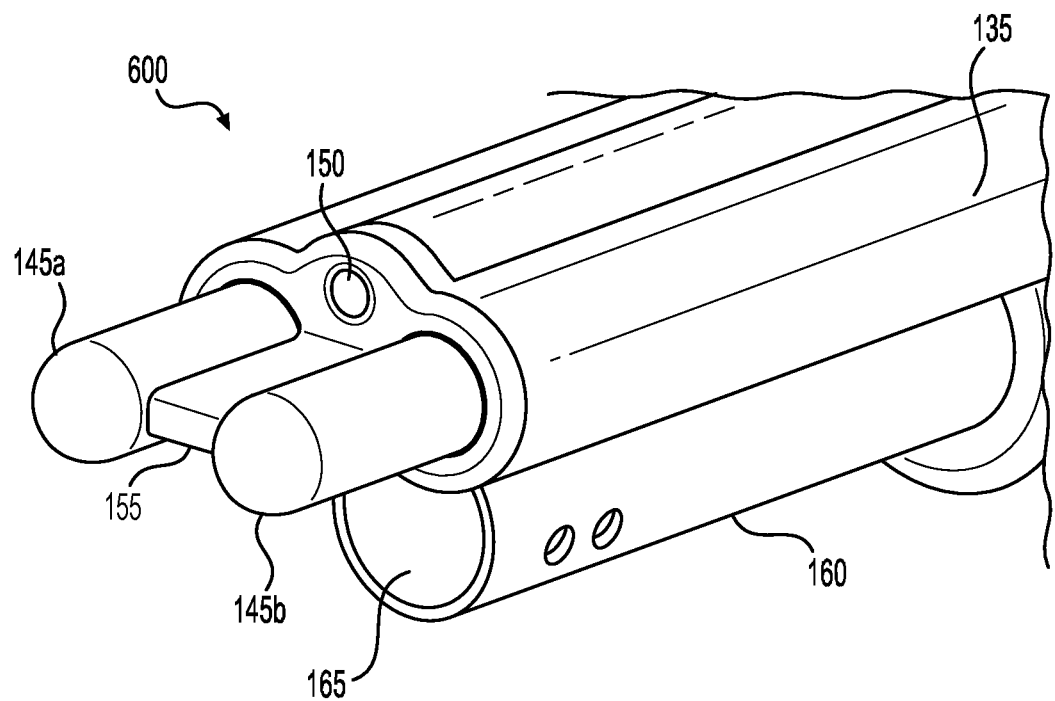
FIG. 35 illustrates a perspective view of one aspect of an end effector of the electrosurgical device depicted in FIG. 1.

FIG. 35 presents a perspective view of a general example of an end effector 600. As disclosed above, the end effector may be composed of a pair of electrodes 145a,b, extending from a shaft 135, a distal fluid discharge port 150, a diverter 155, and an aspiration port 165 that may be part of an aspiration tube 160. The diverter 155 may be placed between the pair of electrodes 145a,b in such a manner as to form a contact of a first edge of the diverter 155 with a surface of one electrode 145a, and a contact of a second edge of the diverter 155 with a surface on a second electrode 145b. In some examples, a proximal edge of the diverter 155 may form a mechanical communication with an end surface of the shaft 135. In this manner, fluid emitted by the distal fluid discharge port 150 may be retained on a first or top surface of the diverter 155. The fluid on the top surface of the diverter 155 may be retained on that surface for a sufficient time to maintain contact of the fluid with a surface of both electrodes 145a,b. If the fluid is an ionic fluid, current passing through the fluid between the electrodes 145a,b may heat the fluid sufficiently to form a steam capable of cauterizing tissue.

Figure 36:
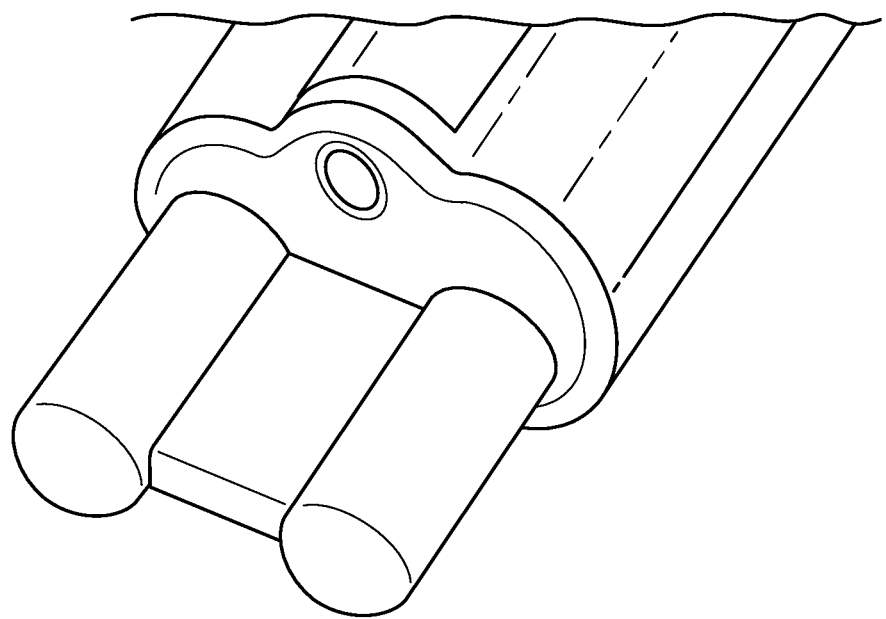
FIG. 36 illustrates a perspective view of a model of one aspect of an end effector of the electrosurgical device depicted in FIG. 1.

FIG. 36 depicts a perspective view of a fabricated model of the end effector 600 as depicted in FIG. 35.

FIGS. 37-44 depict a variety of examples of an end effector as generally disclosed as end effector 600 depicted in FIG. 35.

Figure 37:
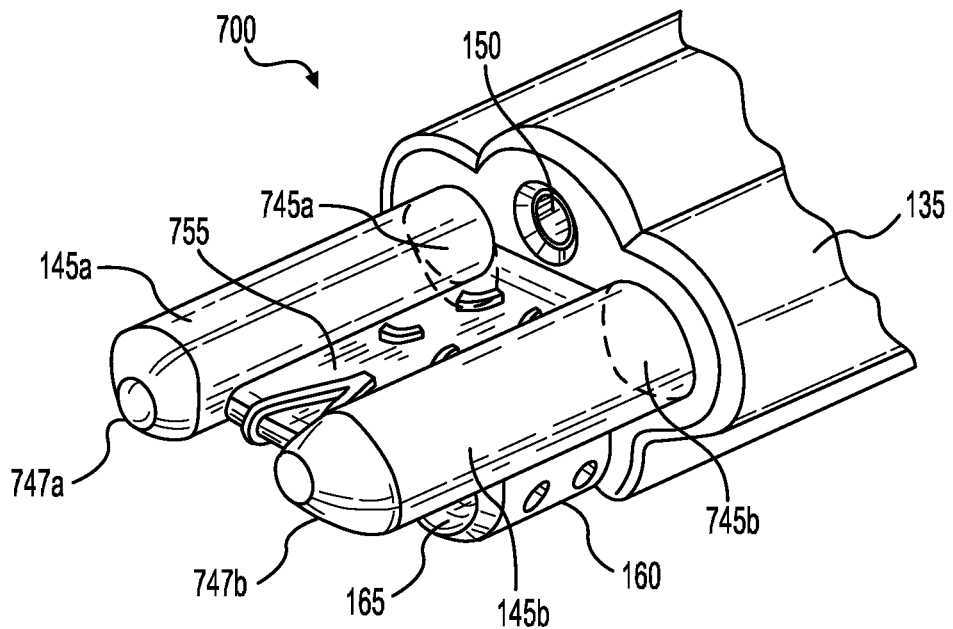
FIG. 37 illustrates a perspective view of a first aspect of a pair of electrodes and a diverter of an end effector of an electrosurgical device depicted in FIG. 1.
Figure 38:
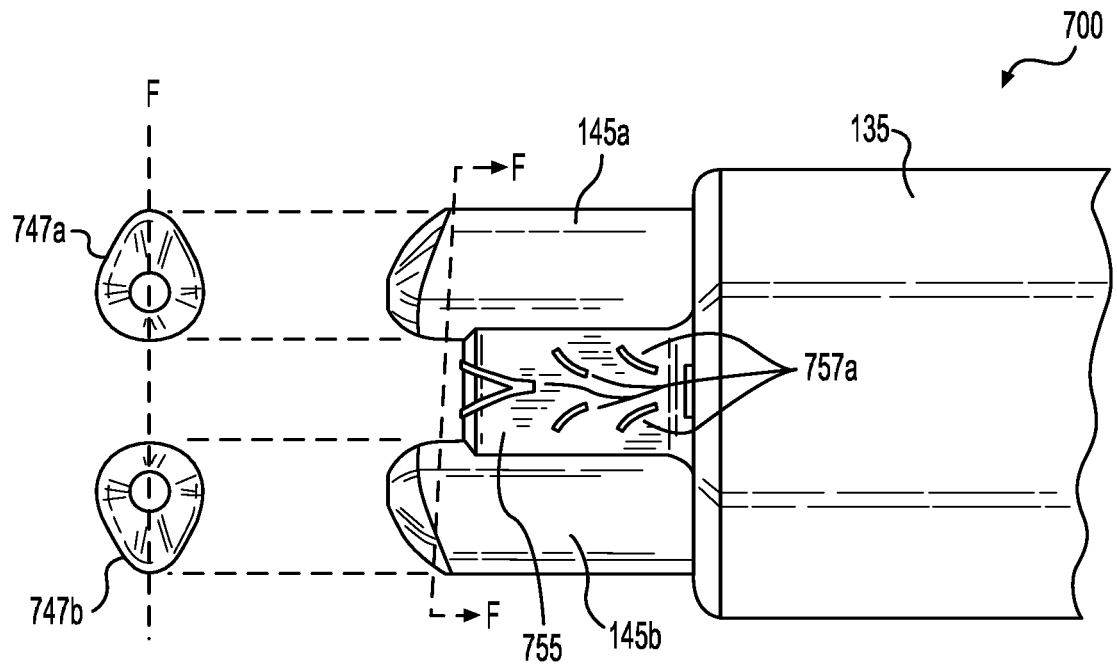
FIG. 38 illustrates a top plan view of the first aspect of a pair of electrodes and a diverter depicted in FIG. 37.

FIGS. 37 and 38 illustrate a perspective view and a top plan view, respectively, of one example of end effector 700. End effector 700 illustrates many of the components disclosed above with respect to end effector 600 of FIG. 36. These components include the shaft 135, the fluid discharge port 150, the aspirator port 165, the electrodes 145a,b, and aspirator tube 160. In addition to the aspirator port 165, the aspirator tube 160 may include additional ports along the length of the aspirator tube 160 to aspirate material from the surgical site. The diverter 755 of end effector 700 includes a number of features 757a configured to direct the flow of a fluid emitted by fluid discharge port 150 to the surface of electrodes 145a,b. Features 757a may include curved guide-ways protruding from the top surface of the diverter 755. Additionally, the top surface of the diverter 755 may include additional features at the distal end to further guide the fluid towards the electrodes 145*a,b*. The electrodes 145*a,b* may have a generally circular or elliptical cross section 745*a,b* at a portion near the distal end of the shaft 135. Further, the electrodes 145*a,b* may be chamfered at their distal ends 747*a,b* resulting in an oval or egg-shaped distal end 747*a,b*. Cross-sectional view F in FIG. 38 illustrates that the oval distal ends 747*a,b* of the electrodes 145*a,b* have their respective long axes directed to the outer portion of the end effector 700, away from the diverter 755.

Figure 39:
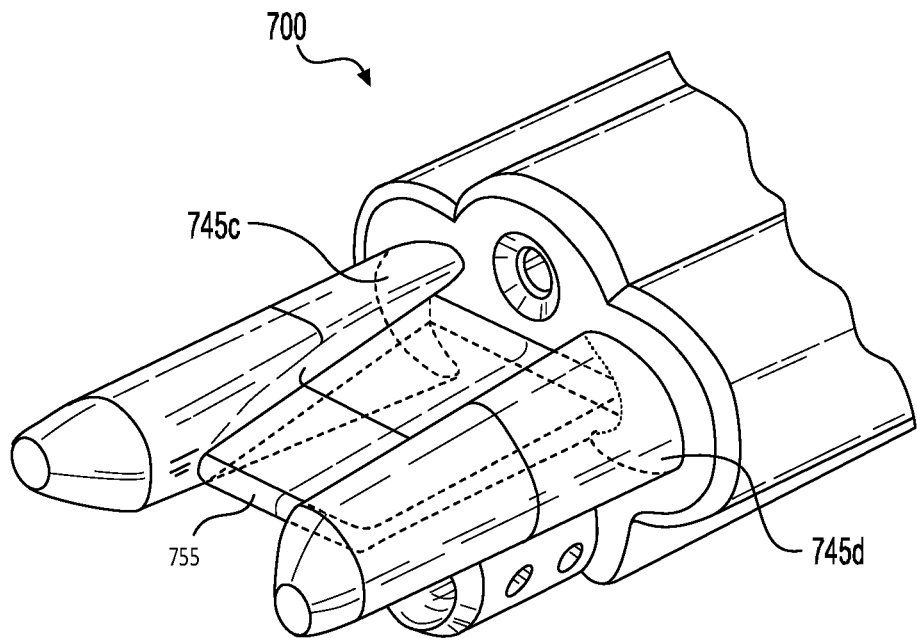
FIG. 39 illustrates a perspective view of a second aspect of a pair of electrodes and a diverter of an end effector of an electrosurgical device depicted in FIG. 1.
Figure 40:
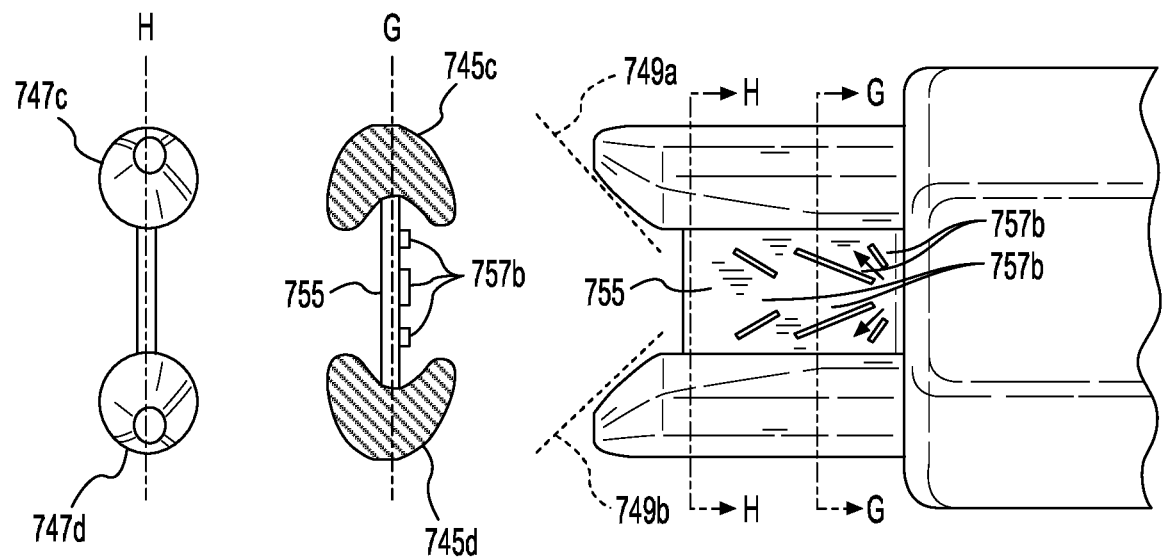
FIG. 40 illustrates a top plan view of the second aspect of a pair of electrodes and a diverter depicted in FIG. 39.

FIGS. 39 and 40 illustrate a perspective view and a top plan view, respectively, of another example of end effector 700. In FIGS. 39 and 40, the distal portion of the electrodes 145*a,b* may have a circular or oval cross section, but the electrodes 145*a,b* may have a fabiform or kidney-shaped cross section 745*c,d* closer (proximal) to the shaft 135. Such a fabiform cross section 745*c,d* may be useful during fabrication of the electrosurgical device to secure the diverter 755 between the inner surfaces of the electrodes 145*a,b*. Cross sectional view G of FIG. 40 illustrates how the diverter 755 may be secured against the inner surfaces of the fabiform cross section 745*c,d*. The example of end effector 700 depicted in FIGS. 39 and 40 also are distinguished from that depicted in FIGS. 37 and 38 in that the features 757*b* comprising the protruding fluid guide-ways comprise straight guide-ways to direct the fluid on the top surface of the diverter 755 to the electrodes 145*a,b*. Additionally, the electrodes 145*a,b* may be chamfered to result in oval distal ends 747*c,d* in which the respective long axes 749*a,b* are directed towards the inner portion of the end effector 700, and pointing towards the diverter 755. This geometry is depicted in FIG. 40, cross-sectional view H.

Figure 41:
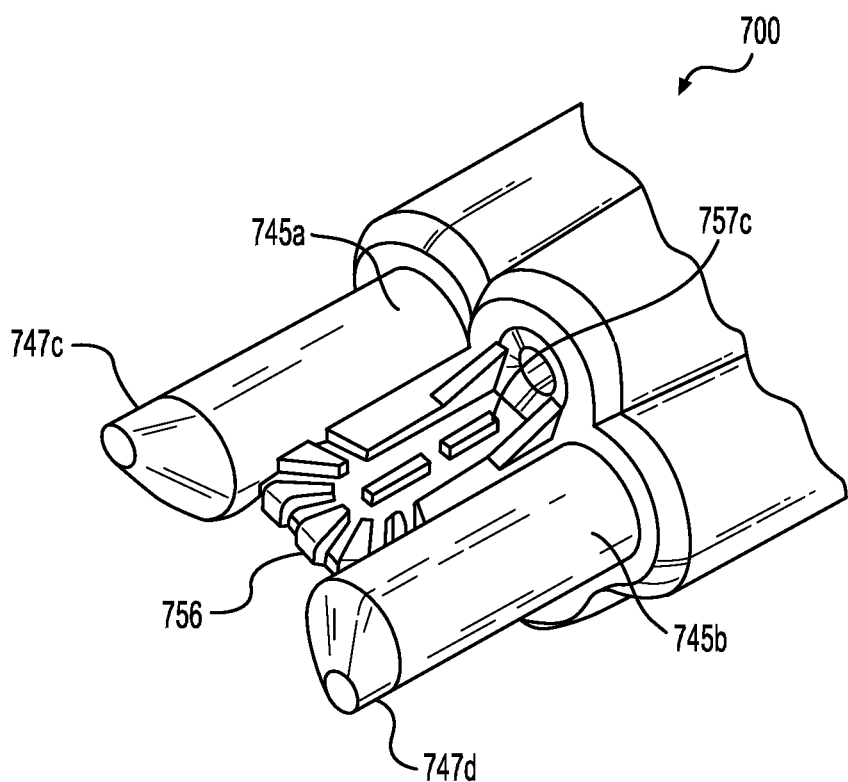
FIG. 41 illustrates a perspective view of a third aspect of a pair of electrodes and a diverter an end effector of an electrosurgical device depicted in FIG. 1.
Figure 42:
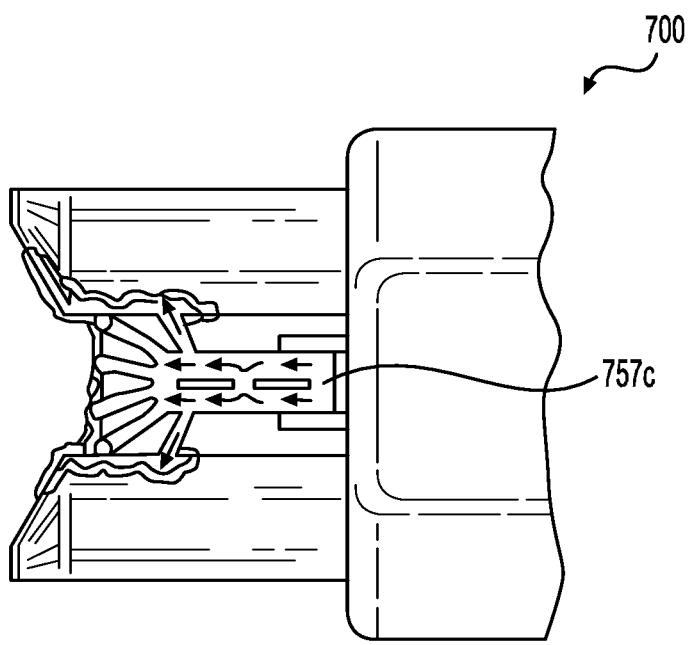
FIG. 42 illustrates a top plan view of the third aspect of a pair of electrodes and a diverter depicted in FIG. 41.

FIGS. 41 and 42 illustrate a perspective view and a top plan view, respectively, of yet another example of end effector 700. The end effector 700 depicted in FIGS. 41 and 42 shows common elements to those of examples illustrated in FIGS. 37-40. Thus, the electrodes 145*a,b* have a circular or elliptical cross section 745*a,b* as illustrated in FIGS. 37 and 38 but include the oval cross sections 747*c,d* at the distal ends of the electrodes 145*a,b* as depicted in FIGS. 39 and 40. The fluid flow features 757*c* illustrated in FIGS. 41 and 42 are fabricated as recesses in the surface of the diverter 756. Such recess features 757*c* may form channels that may be used to guide the flow of a fluid on the top surface of the diverter 756 as suggested by the arrows shown in FIG. 42. The recess figures 757*c* may also specifically guide a flow of the fluid against the inner surfaces of electrodes 145*a,b* as also illustrated in FIG. 42. The features 757*c* may also include a spill-way to direct the fluid emitted by the fluid discharge port 150 towards the channels in the surface of diverter 756 thereby preventing the fluid from flowing out of the recesses when the fluid initially leaves the fluid discharge port 150.

Figure 43:
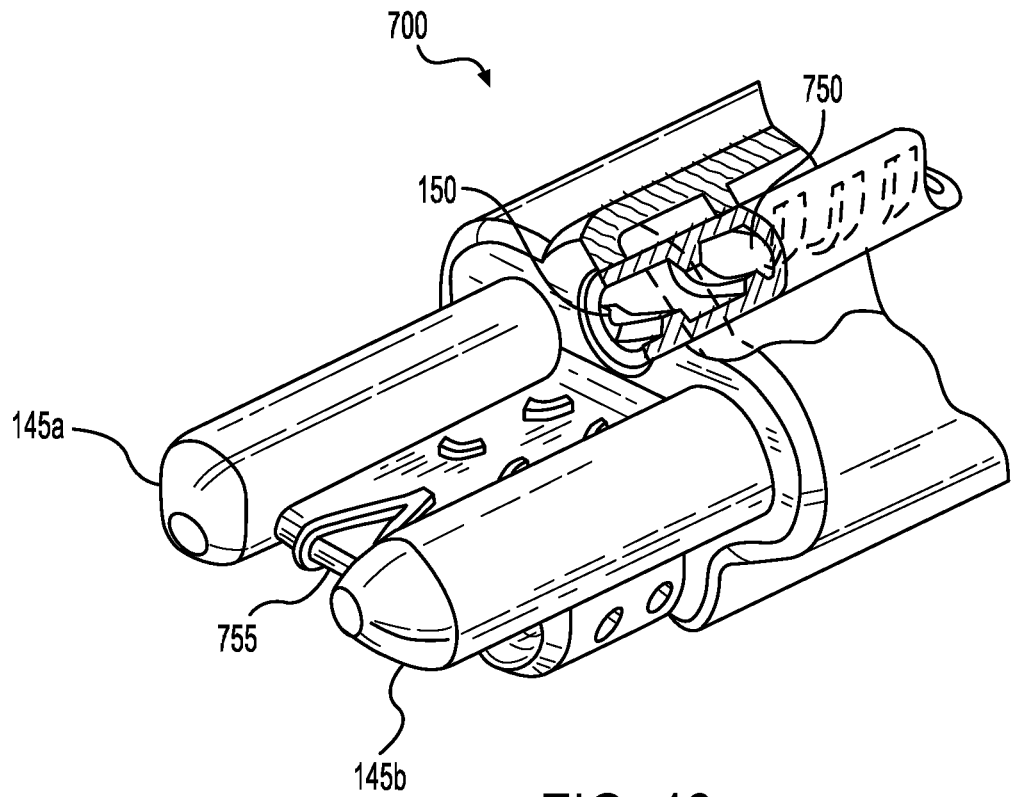
FIG. 43 illustrates a perspective view of an alternate aspect of the end effector of an electrosurgical device depicted in FIG. 37.
Figure 44:
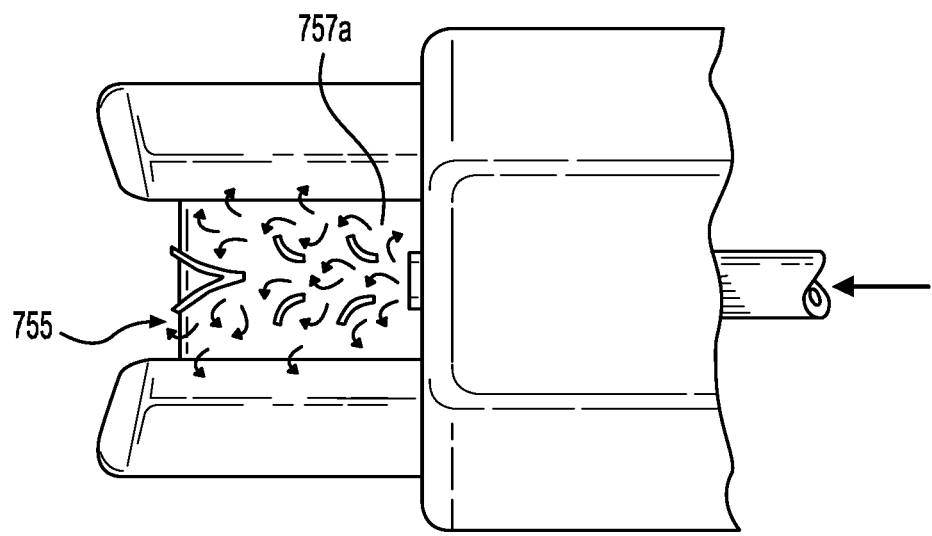
FIG. 44 illustrates a top plan view of the alternate aspect of the end effector of an electrosurgical device depicted in FIG. 43.

FIGS. 43 and 44 illustrate a perspective view and a top plan view, respectively, of still another example of end effector 700. The electrodes 145*a,b*, shaft 135, the fluid discharge port 150, the aspirator port 165, and aspirator tube 160 are all similar to the examples depicted in FIG. 37. Additionally, a portion of the source fluid path 315 proximal to the fluid discharge port 150 may include features such as rifling 750 on the inner surface of the source fluid path 315. Such rifling 750 may impart a turbulent flow to a fluid emitted by the fluid discharge port 150, especially if the fluid is sourced under pressure. Thus, a fluid entering the distal end of source fluid path 315 (arrow on right of FIG. 44) may exit at the fluid discharge port 150 having a turbulent flow that is more easily distributed by the features 757*a* on the top surface of diverter 755, as illustrated by the arrows superimposed on the top surface of diverter 755 in FIG. 44. As a result, the fluid on the top surface of diverter 755 may more readily flow to contact the electrodes 145*a,b*.

Figure 45:
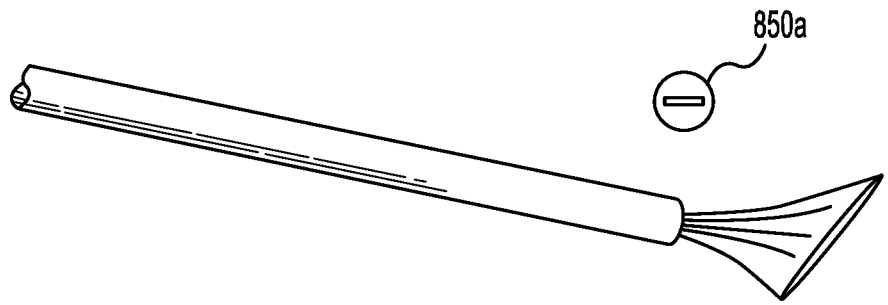
FIGS. 45, 46, and 47 illustrate aspects of a fluid supply path and discharge port of an end effector of an electrosurgical device depicted in FIG. 1.
Figure 46:
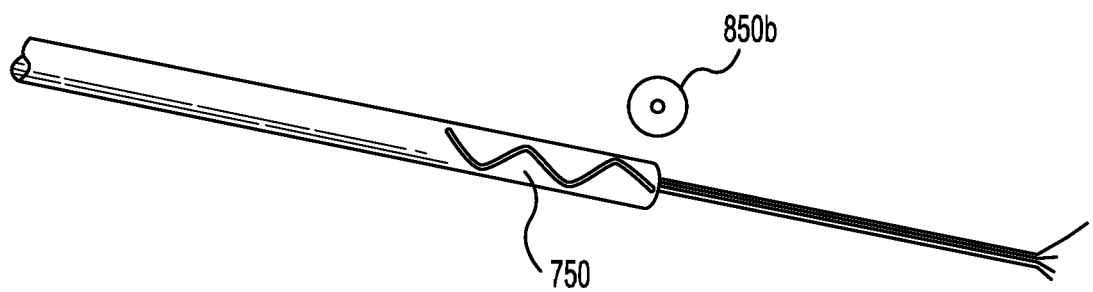
Figure 47:
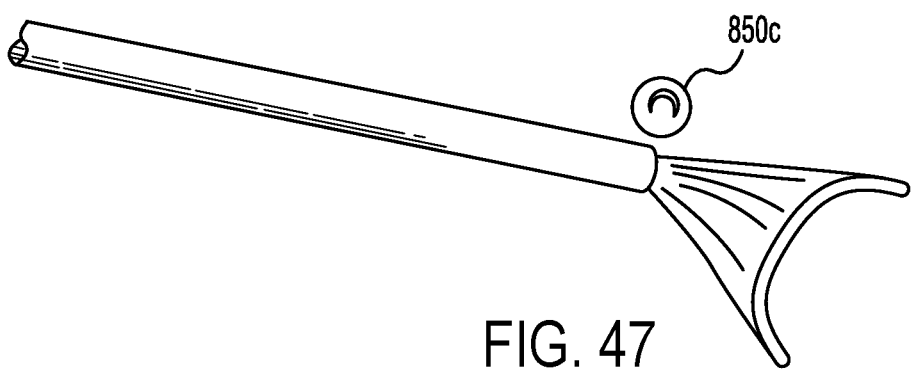

The flow of a fluid emitted by fluid discharge port 150 may also be varied by the incorporation of apertures at the distal end of the fluid discharge port 150. FIGS. 45, 46, and 47 illustrate, respectively, fluid flow through a slit aperture 850*a*, a circular or pinhole aperture 850*b*, and a semi-lunar aperture 850*c*. The rifling 750 may be added to a source fluid path 315 terminating in a fluid discharge port 150 having any of the apertures 850*a-c* as illustrated in FIGS. 45-47. FIG. 46, for example, depicts the rifling 750 used in addition to a circular or pinhole aperture 850*b*.

Figure 48:
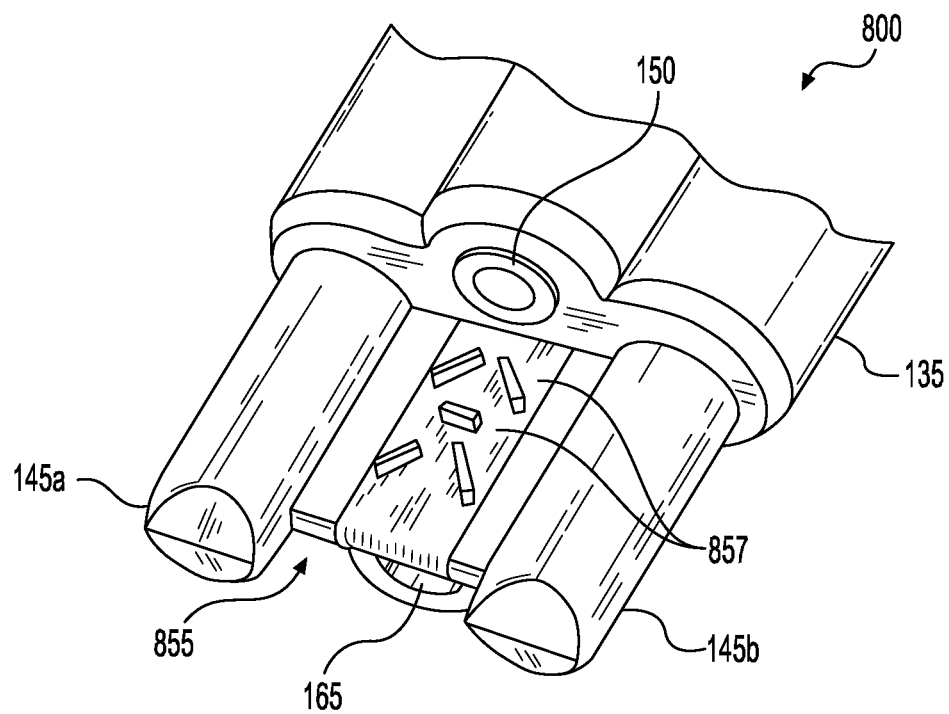
FIG. 48 illustrates a perspective view of an alternative aspect of an end effector of an electrosurgical device depicted in FIG. 1.
Figure 49:
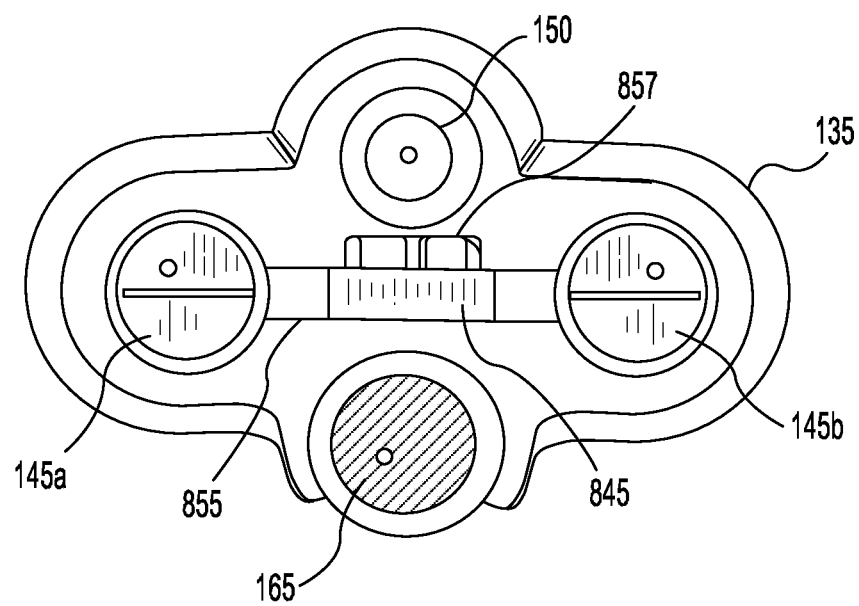
FIG. 49 illustrates a front (distal) plan view of the alternative aspect of the end effector depicted in FIG. 48.

FIGS. 48 and 49 illustrate a perspective view and a vertical cross sectional view, respectively, of an example of end effector 800 that comprises three electrodes. The end effector 800 depicted in FIGS. 48 and 49 includes, as disclosed in examples depicted in FIGS. 37-44, a distal end of a shaft 135, a fluid discharge port 150, and an aspirator port 165. Also depicted in FIGS. 48 and 49 are a pair of electrodes 145*a,b* that are disposed juxtaposed to each other and are separated by a diverter 855. The diverter 855 illustrated in FIGS. 48 and 49 may include a series of protruding feature 857 that may differ from those in examples depicted in FIGS. 37-40. In the example of end effector 800 illustrated by FIGS. 48 and 49, a third electrode 845 may be incorporated on the top surface of the diverter 855. In the examples of end effectors illustrated above, the two electrodes 145*a,b* are disposed juxtaposed to each having a spacing between them. As disclosed above, a first electrode 145*a* may receive electrical energy of a first polarity (such as a positive polarity) from the energy supply 120 and the second electrode 145*b* may receive electrical energy of a second and opposing polarity (such as a negative polarity) from the energy supply 120. Alternatively, the first electrode 145*a* may be connected to a ground terminal of the energy supply 120, and the second electrode 145*b* may be connected to a varying AC voltage terminal of the energy supply 120. The electrodes 145*a,b* illustrated in FIGS. 48 and 49 may receive electrical energy having the same polarity while additional electrode 845 may receive electrical energy having a second and opposing polarity. Alternatively, electrodes 145*a,b* may be connected to a varying AC voltage terminal of the energy supply 120 while the third electrode 845 may be connected to a ground terminal of the energy supply 120. In yet another alternative example, electrodes 145*a,b* may be connected to a ground terminal of the energy supply 120 while the third electrode 845 may be connected to a varying AC voltage terminal of the energy supply 120. It may be understood that an end effector may include any number of electrodes disposed in any appropriate geometry around or about a diverter placed therebetween or thereamong.

Figure 50:
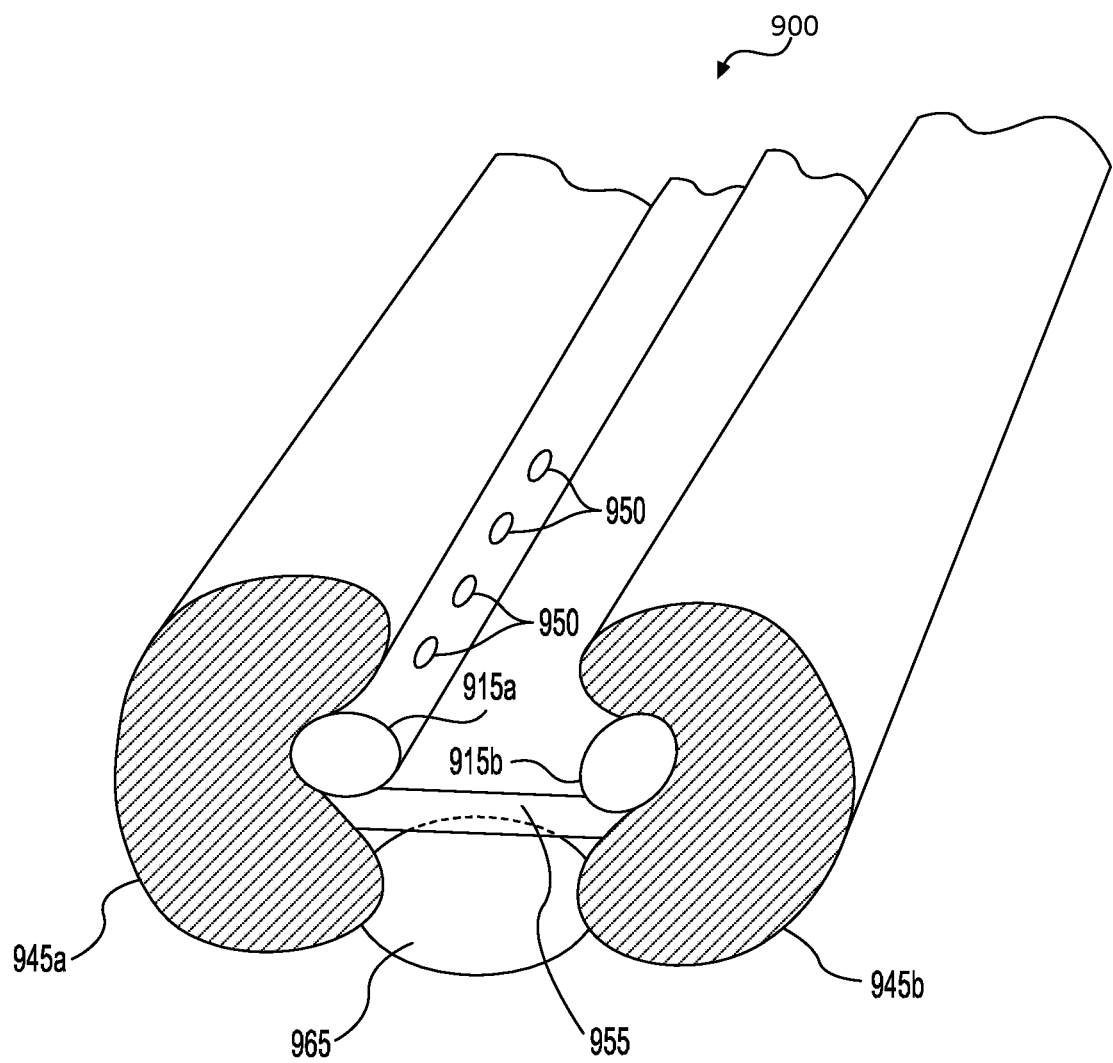
FIG. 50 illustrates another aspect of the end effector of an electrosurgical device depicted in FIG. 1

FIG. 50 illustrates an alternative example of an end effector 900. End effector 900 includes a pair of electrodes 945*a,b* that have a fabiform or kidney-shaped cross section. Diverter 955 is positioned between the concave inner surfaces of electrodes 945*a,b*, and an aspirator tube having a distal aspiration port 965 is positioned below the diverter 955. Unlike many of the end effectors disclosed above, the source fluid path 315 in end effector 900 does not terminate in a discharge port 150 at a distal end of the shaft 135. Instead, as illustrated in FIG. 50, the source fluid path 315 may continue along the length of one or more of the electrodes. For example, the source fluid path 315 may extend as one or more cannulae 915a,b that are positioned, for example, along the inner concave surface of the electrodes 945a,b. The cannulae 915a,b may be placed against or in proximity to the top surface of the diverter 955. The cannulae 915a,b may also include pores or weep-holes 950 that may permit a fluid flowing through the source fluid path 315 and the cannulae 915a,b, to flow onto the top surface of the diverter 955. The fluid may flow from the pores or weep-holes 950 onto the top surface of the diverter 955 due to capillary action and/or surface tension. Although two cannulae 915a,b, are illustrated in FIG. 50, it may be understood that a single cannula or multiple cannulae may be used to provide the fluid to flow onto the top surface of the diverter 955.

It will be appreciated that the terms "proximal" and "distal" are used throughout the specification with reference to a clinician manipulating one end of an instrument used to treat a patient. The term "proximal" refers to the portion of the instrument closest to the clinician and the term "distal" refers to the portion located furthest from the clinician. It will further be appreciated that for conciseness and clarity, spatial terms such as "vertical," "horizontal," "up," or "down" may be used herein with respect to the illustrated embodiments. However, surgical instruments may be used in many orientations and positions, and these terms are not intended to be limiting or absolute.

Various aspects of surgical instruments are described herein. It will be understood by those skilled in the art that the various aspects described herein may be used with the described surgical instruments. The descriptions are provided for example only, and those skilled in the art will understand that the disclosed examples are not limited to only the devices disclosed herein, but may be used with any compatible surgical instrument or robotic surgical system.

Reference throughout the specification to "various aspects," "some aspects," "one example," or "one aspect" means that a particular feature, structure, or characteristic described in connection with the aspect is included in at least one example. Thus, appearances of the phrases "in various aspects," "in some aspects," "in one example," or "in one aspect" in places throughout the specification are not necessarily all referring to the same aspect. Furthermore, the particular features, structures, or characteristics illustrated or described in connection with one example may be combined, in whole or in part, with features, structures, or characteristics of one or more other aspects without limitation.

While various aspects herein have been illustrated by description of several aspects and while the illustrative embodiments have been described in considerable detail, it is not the intention of the applicant to restrict or in any way limit the scope of the appended claims to such detail. Additional advantages and modifications may readily appear to those skilled in the art. For example, it is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to an instrument for use only in conjunction with an endoscopic tube (e.g., trocar). On the contrary, it is believed that the present invention may find use in any procedure where access is limited to a small incision, including but not limited to laparoscopic procedures, as well as open procedures.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several aspects have been described, it should be apparent, however, that various modifications, alterations and adaptations to those embodiments may occur to persons skilled in the art with the attainment of some or all of the advantages of the disclosure. For example, according to various aspects, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered examples:

Example 1

An electrosurgical device comprising: a proximal fluid source port and a first fluid path in fluid communication with the proximal fluid source port; a proximal fluid evacuation port and a second fluid path in fluid communication with the proximal fluid evacuation port; a first electrode and a second electrode; a housing configured to enclose a first portion of the first fluid path, a first portion of the second fluid path, a first portion of the first electrode, and a first portion of the second electrode; a shaft extending distally from the housing configured to enclose a second portion of the first fluid path, a second portion of the second fluid path, a second portion of the first electrode, and a second portion of the second electrode and an end effector, the end effector comprising: a distal fluid discharge port in fluid communication with the second portion of the first fluid path; a distal fluid aspiration port in fluid communication with the second portion of the second fluid path; a third portion of the first electrode and a third portion of the second electrode; and a diverter comprising a first surface, a first edge in mechanical communication with the third portion of the first electrode and a second edge in mechanical communication with the third portion of the second electrode.

Example 2

The electrosurgical device of Example 1, wherein the diverter is configured to maintain a contact between the fluid, a surface of the third portion of the first electrode, and a surface of the third portion of the second electrode.

Example 3

The electrosurgical device of Example 1, wherein the diverter comprises a plurality of features on the first surface.

Example 4

The electrosurgical device of Example 3, wherein the plurality of features are configured to direct a fluid flow of the fluid on the first surface of the diverter.

Example 5

The electrosurgical device of Example 3, wherein the plurality of features comprise a plurality of protrusions.

Example 6

The electrosurgical device of Example 3, wherein the plurality of features comprise a plurality of recesses.

Example 7

The electrosurgical device of Example 1, wherein the distal fluid discharge port comprises an aperture comprising a circular opening, a semi-lunar opening, or a slit opening.

Example 8

The electrosurgical device of Example 1, wherein the second portion of the first fluid path proximal to the distal fluid discharge port is configured to impart a turbulent flow to a fluid flowing therethrough.

Example 9

The electrosurgical device of Example 1, wherein the second portion of the first fluid path comprises a first cannula and a second cannula.

Example 10

The electrosurgical device of Example 9, wherein the first cannula is in mechanical communication with an inner surface of the third portion of the first electrode and the second cannula is in mechanical communication with an inner surface of the third portion of the second electrode.

Example 11

The electrosurgical device of Example 9, wherein the distal fluid discharge port comprises a plurality of pores in the first cannula and the second cannula.

Example 12

An end effector of an electrosurgical device, the end effector comprising: a distal fluid discharge port in fluid communication with a first fluid path; a distal fluid aspiration port in fluid communication with a second fluid path; a first electrode and a second electrode; and a diverter in mechanical communication with the first electrode and the second electrode, and disposed therebetween, wherein the diverter is configured to receive, on a first surface, a fluid emitted by the distal fluid discharge port, and to maintain a contact of the fluid thereon with a surface of the first electrode and a surface of the second electrode, and wherein the diverter is configured to prevent an aspiration by the distal fluid aspiration port of the fluid on the first surface thereof.

Example 13

The end effector of Example 12, wherein the diverter comprises an electrically insulating material.

Example 14

The end effector of Example 12, wherein the diverter comprises a heat resistant material.

Example 15

The end effector of Example 12, wherein the diverter comprises a plurality of features on the first surface.

Example 16

The end effector of Example 15, wherein the plurality of features are configured to direct a flow of the fluid on the first surface of the diverter towards the first electrode or the second electrode.

Example 17

The end effector of Example 15, wherein the plurality of features comprise a plurality of protrusions.

Example 18

The end effector of Example 15, wherein the plurality of features comprise a plurality of recesses.

Example 19

The end effector of Example 12, wherein the first fluid path comprises a first cannula and a second cannula.

Example 20

The end effector of Example 19, wherein the first cannula is in mechanical communication with an inner surface of the first electrode and the second cannula is in mechanical communication with an inner surface of the second electrode.

Example 21

The end effector of Example 19, wherein the distal fluid discharge port comprises a plurality of pores in the first cannula and the second cannula and wherein the plurality of pores are configured to source the fluid onto the first surface of the diverter.

Example 22

An end effector of an electrosurgical device, the end effector comprising: an outlet port in fluid communication with a first fluid path; an inlet port in fluid communication a second fluid path; a first electrode and a second electrode positioned in juxtaposed relationship; and a diverter comprising a first surface configured to receive fluid emitted by the outlet port, wherein the diverter is disposed between the first and second juxtaposed electrodes, and wherein the diverter is disposed between the outlet port and the inlet port to separate the outlet port and the inlet port.

Example 23

The electrosurgical device of Example 1, wherein the diverter is configured to receive, on the first surface, a fluid emitted by the distal fluid discharge port.

Example 24

The electrosurgical device of Example 1, wherein the distal fluid aspiration port is configured to remove a material from an area proximal to the diverter.

What is claimed is:

1. An electrosurgical device comprising:
   a proximal fluid source port and a first fluid path in fluid communication with the proximal fluid source port;
   a proximal fluid evacuation port and a second fluid path in fluid communication with the proximal fluid evacuation port;
   a first electrode configured to be in electrical communication with a first terminal of an energy supply having a first polarity and a second electrode configured to be in electrical communication with a second terminal of the energy supply having an opposing polarity to the first terminal;
   a housing;
   a shaft extending distally from the housing; and
   an end effector, disposed at a distal end of the shaft, the end effector comprising:
      a distal fluid discharge port in fluid communication with the first fluid path;
      a distal fluid aspiration port in fluid communication with the second fluid path;
      an exposed distal portion of the first electrode and an exposed distal portion of the second electrode; and
      a diverter comprising a first surface, a first terminal lateral side in mechanical communication with an inner surface of the exposed distal portion of the first electrode, and a second terminal lateral side in mechanical communication with an inner surface of the exposed distal portion of the second electrode,
      wherein the first surface comprises a plurality of features configured to direct a flow of the fluid on the first surface and wherein the plurality of features comprises a plurality of protrusions or recesses.

2. The electrosurgical device of claim 1, wherein the diverter is configured to maintain a contact between a fluid, a surface of the exposed distal portion of the first electrode, and a surface of the exposed distal portion of the second electrode.

3. The electrosurgical device of claim 1, wherein the distal fluid discharge port comprises an aperture comprising a circular opening, a semi-lunar opening, or a slit opening.

4. The electrosurgical device of claim 1, wherein a portion of the first fluid path disposed proximal to the distal fluid discharge port is configured to impart a turbulent flow to a fluid flowing therethrough.

5. The electrosurgical device of claim 1, wherein the distal fluid discharge port comprises a first cannula in mechanical communication with the inner surface of the exposed distal portion of the first electrode and a second cannula in mechanical communication with the inner surface of the exposed distal portion of the second electrode.

6. The electrosurgical device of claim 5, wherein the distal fluid discharge port comprises a plurality of pores in the first cannula and the second cannula.

7. The electrosurgical device of claim 1, wherein the distal fluid discharge port is disposed on a distal end of an aspiration tube.

8. The electrosurgical device of claim 7, wherein the aspiration tube is configured to be placed in a retracted configuration or in an extended configuration.

9. The electrosurgical device of claim 8, wherein the housing further comprises a slide switch configured to place the aspiration tube in the retracted configuration or in the extended configuration.

10. The electrosurgical device of claim 8, wherein the distal fluid discharge port is positioned under and proximal to a distal end of the diverter when the aspiration tube is placed in the retracted configuration.

11. The electrosurgical device of claim 8, wherein the distal fluid discharge port is positioned under and distal to a distal end of the diverter when the aspiration tube is placed in the extended configuration.

12. The electrosurgical device of claim 1, wherein the diverter further comprises a third electrode.

13. The electrosurgical device of claim 12, wherein a top surface of the third electrode comprises at least a portion of the first surface of the diverter.

14. The electrosurgical device of claim 13, wherein the plurality of features comprise a plurality of protrusions disposed on the top surface of the third electrode.

15. The electrosurgical device of claim 12, wherein the third electrode is disposed through at least a part of an entire thickness of the diverter.

16. The electrosurgical device of claim 1, wherein the exposed distal portion of the first electrode and the exposed distal portion of the second electrode each has a fabiform cross-section.

17. The electrosurgical device of claim 16, wherein the first terminal lateral side of the diverter is disposed against an inner surface of the fabiform cross-section of the exposed distal portion of the first electrode, and
   wherein the second terminal lateral side of the diverter is disposed against an inner surface of the fabiform cross-section of the exposed distal portion of the second electrode.

18. The electrosurgical device of claim 17, wherein the distal fluid discharge port comprises a first cannula in mechanical communication with the inner surface of the fabiform cross-section of the exposed distal portion of the first electrode and a second cannula in mechanical communication with the inner surface of the of the fabiform cross-section of the exposed distal portion of the second electrode.

* * * * *